(12) United States Patent
Benson

(10) Patent No.: US 7,989,165 B2
(45) Date of Patent: *Aug. 2, 2011

(54) TAPE STRIPPING METHODS FOR ANALYSIS OF SKIN DISEASE AND PATHOLOGICAL SKIN STATE

(75) Inventor: Nicholas R. Benson, San Diego, CA (US)

(73) Assignee: DermTech International, San Diego, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 11/710,661

(22) Filed: Feb. 23, 2007

(65) Prior Publication Data

US 2007/0202540 A1 Aug. 30, 2007

Related U.S. Application Data

(63) Continuation of application No. 10/816,457, filed on Mar. 31, 2004, now Pat. No. 7,183,057.

(51) Int. Cl.
*C12Q 1/68* (2006.01)
*G01N 33/53* (2006.01)
*C07K 14/00* (2006.01)
*C07H 21/02* (2006.01)
*C07H 21/04* (2006.01)

(52) U.S. Cl. ............ 435/6; 435/7.1; 530/350; 536/23.1; 536/24.3

(58) Field of Classification Search ............... 435/6, 7.1; 530/350
See application file for complete search history.

(56) References Cited

U.S. PATENT DOCUMENTS

| | | | | |
|---|---|---|---|---|
| 4,851,510 | A * | 7/1989 | Khan | 530/388.85 |
| 5,493,009 | A * | 2/1996 | Ferrone | 530/387.2 |
| 5,654,286 | A * | 8/1997 | Hostetler | 514/47 |
| 5,807,522 | A | 9/1998 | Brown et al. | 422/50 |
| 5,962,477 | A * | 10/1999 | Mak | 514/327 |
| 6,054,277 | A | 4/2000 | Furcht et al. | |
| 6,056,859 | A | 5/2000 | Ramsey et al. | |
| 6,312,909 | B1 * | 11/2001 | Shyjan | 435/6 |
| 6,355,439 | B1 | 3/2002 | Chung et al. | 435/6 |
| 6,410,019 | B1 | 6/2002 | De Simone et al. | 424/130.1 |
| 6,720,145 | B2 | 4/2004 | Rheins et al. | 435/6 |
| 6,949,338 | B2 | 9/2005 | Rheins et al. | 435/6 |
| 7,183,057 | B2 * | 2/2007 | Benson | 435/6 |
| 7,615,349 | B2 | 11/2009 | Riker et al. | |
| 2002/0037538 | A1 | 3/2002 | Trepicchio et al. | 435/7.21 |
| 2002/0086019 | A1 * | 7/2002 | Wolf et al. | 424/146.1 |
| 2002/0197604 | A1 * | 12/2002 | Rheins et al. | 435/6 |
| 2003/0032617 | A1 | 2/2003 | Harel et al. | 514/46 |
| 2003/0044406 | A1 | 3/2003 | Dingivan | 424/130.1 |
| 2003/0049256 | A1 | 3/2003 | Tobinick | 424/145.1 |
| 2003/0108896 | A1 | 6/2003 | Vogt | 435/6 |
| 2003/0113906 | A1 | 6/2003 | Sangha et al. | 435/287.2 |
| 2003/0133936 | A1 * | 7/2003 | Byrne et al. | 424/146.1 |
| 2003/0224422 | A1 | 12/2003 | Evans et al. | 506/7 |
| 2003/0224465 | A1 * | 12/2003 | Nevalainen et al. | 435/7.23 |
| 2004/0191782 | A1 * | 9/2004 | Wang | 435/6 |
| 2006/0182755 | A1 | 8/2006 | Bodary-Winter et al. | 424/185.1 |
| 2006/0294615 | A1 * | 12/2006 | Lin | 800/18 |
| 2007/0179198 | A1 * | 8/2007 | Iwai et al. | 514/789 |

FOREIGN PATENT DOCUMENTS

WO WO 00/10579 3/2000
WO WO 03/001985 A2 1/2003

OTHER PUBLICATIONS

Ghali et al., Epidermal and Hair Follicle Progenitor Cells Express Melanoma-Associated Chondroitin Sulfate Proteoglycan Core Protein. Journal of Investigative Dermatology 122 : 433-442 (2004).*
Thiele et al., Macromolecular carbonyls in human stratum corneum: a biomarker for environmental oxidant exposure? FEBS Letters 422 : 403-406 (1998).*
Thiele et al., Protein Oxidation in Human Stratum Corneum: Susceptibility of Keratins to Oxidation In Vitro and Presence of a Keratin Oxidation Gradient In Vivo. Journal of Investigative Dermatology 113: 335-339 (1999).*
Wang et al., MGSA/GRO-mediated melanocyte transformation involves induction of Ras expression. Oncogene 19 : 4647-4659 (2000).*
Waseem et al., Keratin 15 expression in stratified epithelia: downregulation in activated keratinocytes. Journal of Investigative Dermatology 113 : 362-369 (1999).*
Asadullah et al., Cytokines: inreleukin and interferon therapy in dermatology Clinical & Experimental Dermatology 27 : 578-584 (2002).*
Shattuck et al., MGSA/GRO transcription is differentially regulated in normal retinal pigment epithelial and melanoma cells. Molecular and Cellular Biology 14 (1) : 791-802 (1994).*
Dong et al., Chemokines and diseases. European Journal of Dermatology 13 : 224-230 (2003).*
Benson et al., "A comparison of keratin gene expression between inflamed and control skin obtained by tape harvest", *Journal of Investigative Dermatology*, 122(3):A48 (2004).
McLean et al., "Pharmacogenomic Analysis of Cytogenetic Response in Chronic Myeloid Leukemia Patients Treated with Imatinib", *Clinical Cancer Research*, 10:155-165 (2004).
Morhenn et al., "A noninvasive method for quantifying and distinguishing inflammatory skin reactions", *Journal of the American Academy of Dermatology*, 41(5 Pt 1):687-692 (1999).
Wong et al., "Use of RT-PCR and DNA Microarrays to Characterize RNA Recovered by Non-Invasive Tape Harvesting of Normal and Inflamed Skin", *Journal of Investigative Dermatology*, 123(1):159-167 (2004).

(Continued)

*Primary Examiner* — E C Whisenant
(74) *Attorney, Agent, or Firm* — DLA Piper LLP (US)

(57) ABSTRACT

The present invention provides non-invasive methods for detecting, monitoring, and diagnosing skin disease and pathological skin states such as irritated skin and psoriasis. The methods include using tape stripping to analyze expression in epidermal samples, of one or more skin markers. In illustrative examples, the tape stripping is performed using pliable tape that has a rubber adhesive. Furthermore, the present invention provides methods for predicting and monitoring response to therapy for a skin disease, such as psoriasis or dermatitis. Finally, the methods can include the use of a microarray.

5 Claims, 2 Drawing Sheets

OTHER PUBLICATIONS

Garofano et al., "PCR Based Analyses of Epidermal Cells Found on Adhesive Tape", *Advances in Forensic Haemogenetic*, 6:281-283 (1996).

Gibson et al., "A Novel Method for Real Time Quantitative RT-PCR", *Genome Research*, 6:995-1001 (1996).

Granstein R.D., "New Treatments for Psoriasis", *The New England Journal of Medicine*, 345(4):284-287 (2001).

Heid et al., "Real Time Quantitative PCR", *Genome Research*, 6:986-994 (1996).

Marttin et al., "A Critical Comparison of Methods to Quantify Stratum Corneum Removed by Tape Stripping", *Skin Pharmacol.*, 9:69-77 (1996).

Nickoloff et al., "Keratinocyte Interleukin-10 Expression is Upregulated in Tape-Stripped Skin, Poison Ivy Dermatitis, and Sezary Syndrome, but Not in Psoriatic Plaques", *Clinical Immunology and Immunopathology*, 73(1):63-68 (1994).

Paludan et al., "Use of the Polymerase Chain Reaction in Quantification of Interleukin 8 mRNA in Minute Epidermal Samples", *Journal of Investigative Dermatology*, 99:830-835 (1992).

van der Molen et al., "Tape Stripping of Human Stratum Corneum Yields Cell Layers that Originate from Various Depths Because of Furrows in the Skin", *Arch. Dermatol. Res.*, 289:514-518 (1997).

Asada et al., "Cytokine Gene Expression during the Eliciation Phase of Contact Sensitivity: Regulation by Endogenous IL-4," Journal of Investigative Dermatology. 108(4):406-411 (1997).

Benson et al., "An analysis of select pathogenic messages in lesional and non-lesional psoriatic skin using non-invasive tape harvesting," Journal of Investigative Dermatology, 126: 2234-2241 (2006).

Bittner et al., "Molecular classification of cutaneous malignant melanoma by gene expression profiling", *Nature*, 406:536-540 (2000).

Brand and Braathen, "Untersuchung menschlicher Hautlymphe: Unterscheiden sich irritative und allergische Kontaktdermatitiden bezüglich ihres Zytokinmusters?" Zeitschrift für Hautkrankheiten, 72:435-440.(1997).

Brand et al., "IL-1 beta Protein in Human Skin Lymph Does Not Discriminate Allergic from Irritant Contact Dermatitis," Contact Dermatitis, 35:152-156, (1996).

Cosini and Galli, "Cytokines and Irritant Contact Dermatitis," Toxicology Letters, 102-103:277-282, Elsevier (1998).

Cullander et al., "A quantitative minimally invasive assay for the detection of metals in the stratum corneum", J Pharm Biomed Anal., 22(2):265-79 (2000).

Database CAPLUS on STN, Graengsjoe et al., "Early differences in the epidermal elemental content and expression of cytokines after application of 2 different irritants," Contact Dermatitis, 1996, vol. 35, No. 6, pp. 355-360. See Abstract.

Database EMBASE on STN, AN 96134300, McKenzie et al. "Interleukin-1 receptor antagonist inhibits subcutaneous B16 melanoma growth in vivo," Anticancer Research, 1996, vol. 16, No. 1, pp. 437-441, see abstract.

Davy and Robinson, "Ephrin-A5 modulates, cell adhesion and morphology in an integrin-dependent manner," EMBO J. 19(20):5396-5403 (2000).

Dekker et al, :Characterization of interleukin-1 alpha-induced melanoma cell motility: inhabition by type I and type II receptor-blocking monoclonal antibodies, Melanoma Res. 7(3):223-230 (1997).

Dreher et al., "Colorimetric Method for Quantifying Human Stratum Corneum Removed by Adhesive-Tape-Stripping," Acta Derma Venereol (Stockholm), 78:186-189 (1998).

Easty et al., "Up-regulation of ephrin-A1 during melanoma progression," Int. J. Cancer, 84:494 (1999).

Farage et al., "Further Development of Noninvasive Method for Assessing Human Skin Irritation," Abstract # 1909, The Proctor & Gamble Company, (1998).

Freedberg et al., "Keratins and the Keratinocyte Activation Cycle," The Journal of Investigative Dermatology,The Society for Investigative Dermatology, Inc. 116(5):633-640 (2001).

Garofano et al., "Comparison of Powerplex® 16 System and Other Multiplex STR Typing Kits on Casework," (Reporto Carabinieri Investigazioni Scientifiche, Parma, Italia.), 2000. Reference available at: http ://www. promeea.com/eeneticidproc/ussvmp 11 proc/ default.htm.

Garofano et al., "PCR based analysis of epidermal cells found on adhesive tape," Advances in Forensic Haemogenetic, 6:281-283 (1996). (Istituto diAnatomia e Fisiologia Umana, Universita degli Studi ti Torino, Italy).

Gerritsen et al., "Repeated tape stripping of normal skin: a histological assessment and comparison with events seen in psoriasis", Arch Dermatol Res., 286(8):455-61 (1994).

Goldschmidt et al., "Desquamation of the Human Horny Layer," Archives of Dermatology 95:583-586 (1967).

Grangsjo et al., "Different Pathways in Irritant Contact Eczema? Early Differences in the Epidermal Elemental Content and Expression of Cytokines after Application of 2 Different Irritants," Contact Dermatitis, 35:355-360, (1996).

Gyorffy et al., "A Web-based data warehouse on gene expression in human malignant melanoma," The Journal of Investigative Dermatology, 127(2): 394-399 (2007).

Hamid et al., "In Vivo Expression of IL-12 and IL-13 in Atopic Dermatitis," Journal of Allergy and Clinical Immunology, 98(I):1-8, Mosby-Year Book, Inc. (1996).

Hirao et al., "Elevation of Interleukin 1 Receptor Antagonist in the Stratum Corneum of Sun-Exposed and Ultraviolet B-Irradiated Human Skin," The Journal of Investigative Dermatology, 106(5): 1102-1107 (1996).

Hoefakker et al., "In vivo Cytokine Profiles in Allergic and Irritant Contact Dermatitis," Contact Dermatitis, 33:258-266, Munksgaard, Denmark (1995).

Hojyo-Tomoka et al., "Does Cellophane Tape Stripping Remove the Horny Layer?" Archives of Dermatology 106(5):767-768 (1972).

Howie et al. "Epidermal keratinocyte production of interferon-gamma immunoreactive protein and mRNA is an early event in allergic contact dermatitis." Journal of Investigative Dermatology, 106(6):1218-1223 (1996).

Ijland et al. "Expression of Angiogenic and Immunosuppressive Factors by Uveal Melanoma Cell Lines," Melanoma Research, 9: 445-450 (1999).

Junghans et al., "Epidermal Cytokines IL-ip, TNF-a, and IL-12 in Patients with Atopic Dermatitis: Response to Application of House Dust Mite Antigens," The Journal of Investigative Dermatology, 111(6):1184-1188 (1998).

Katz et al., "Skin-Surface Touch Print for Diagnosing Fungal Infections," American Family Physician 31(4):189-194 (1985).

Klaschka et al., "Individual Transparency Patterns of Adhesive-tape strip series of the stratum corneum," International Journal of Dermatology, 16(10):836-841 (1997).

Klaschka et al., "New Measuring Device of Horny Layer Transparency," Archives of Dermatology 254:313-325 (1975).

Kondo et al., "Characterization of Epidermal Cytokine Profiles in Sensitization and Elicitation Phases of Allergic Contact Dermatitis as Well as Irritant Contact Dermatitis in Mouse Skin," Lymphokine and Cytokine Research, 13(6):367-375 (1994).

Koning et al. "T cell subsets and cytokines in allergic and non-allergic children. I. Analysis of IL-4, IFN-gamma and IL-13 mRNA expression and protein production," Cytokine, 9(6):416-426 (1997).

Lener et al., "Expression profiling of aging in the human skin," Experimental Gerontology, 41: 387-397 (2006).

Lu et al., "MicroRNA expression profiles classify human cancers", Nature, 435(7043):834-838 (2005).

Marionnet, Bernerd et al., "Modulation of gene expression induced in human epidermis by environmental stress in vivo", J Invest Dermatol., 121(6):1447-58 (2003).

Nickoloff, et al., "Perturbation of epidermal barrier function correlates with initiation of cytokine cascade in human skin, " Journal of the American Academy of Dermatology, 30(4):535-546 (1994).

Ohmen et al., "Overexpression of IL-10 in Atopic Dermatitis," The Journal of Immunology, 154:1956-1963(1995).

Onodera et al. "Macrophage migration inhibition factor up-regulates expression of matrix metalloproteinases in synovial fibroblasts of rheumatoid arthritis," J. Biol. Chem, 275:444-450 (2000).

Perkins et al., "A Noninvasive Method to Assess Skin Irritation and Compromised Skin Conditions Using Simple Tape Adsorption of Molecular Markers of Inflammation," Skin Res. Technol., 7(4):227-237 (2001).

Perkins et al., "Development of a Noninvasive Method for Assessing Human Skin Irritation," The Toxicologist, 36(1):365 (1997).

Pistoor et al., "Novel Predictive Assay for Contact Allergens Using Human Skin Explant Cultures," American Journal of Pathology 149(1):337-343 (1996).

Potts, R.O., et al., "Physical Methods for Studying Stratum Corneum Lipids," Seminars in Dermatology, 11(2):129-138 (1992).

Rougier et al., "The measurement of the stratum corneum reservoir. A predictive method for in vivo percutaneous absorption studies: influence of application time," J Invest Dermatol, 84(1):66-8 (1985).

Rougier et al., "In vivo correlation between stratum corneum reservoir function and percutaneous absorption," J Invest Dermatol., 81(3):275-8 (1983).

Rougier et al., "Regional variation in percutaneous absorption in man: measurement by the stripping method," Arch Dermatol Res., 278(6): 465-9 (1986).

Rowe et al., "Interleukin-4 and the interleukin-4 receptor in allergic contact dermatitis," Contact Dermatitis, 38(1):36-39 (1998).

Ryan and Gerberick, "Cytokine mRNA Expression in Human Epidermis after Patch Treatment with Rhus and Sodium Lauryl Sulfate," American Journal of Contact Dermatitis, 10(3):127-135 (1999).

Soufir et al. "Association between endothelin receptor B nonsynonymous variants and melanoma risk," J Natl Cancer inst 97(17):1297-301 (2005).

Torre and Gino, "Epidermal Cells on Stubs Used for Detection of GSR with SEM-EDX: Analysis of DNA Polymorphisms," Journal of Forensic Sciences, JFSCA, 41(4):658-659 (1996).

van der Valk et al., "A functional study of the skin barrier to evaporative water loss by means of repeated cellophane-tape stripping," Clinical and Experimental Dermatology, 15(3):180-182 (1990).

van Hoogdalem et al., "Assay of Erythromycin in Tape Strips of Human Stratum corneum and Some Preliminary Results in Man," Skin Pharmacol 5:124-128 (1992).

Weigand et al., "Removal of stratum corneum in vivo: an improvement on the cellophane tape stripping technique," The Journal of Investigative Dermatology, 60(2):84-87(1973).

Werfel et al., "High IL-4 secretion from skin-derived nickel specific T-lymphocytes is associated with atopy and acute eczema are associated with in allergic contact dermatitis," Journal of Allergy and Clinical Immunology, 101(1):Part 2 (1998).

Werfel et al., "Zytokines as mediators of allergic tissue response" Allergologie, Dustri Velag, Muenchen-Deisenhofen, DE, 20(11): 546-550 (1997).

Yawalkar and Pichler, "Pathogenesis of Drug-Induced Exanthema," Int. Arch. Allergy Immunol., 124:336-338 (2001).

Yi et al., "Morphogenesis in skin is governed by discrete sets of differentially expressed microRNAs", Nature Genetics, 38(3):356-62 (2006).

Nurmi et al., High-performance real-time quantitative RT-PCR using lanthanide probes and a dual-temperature hybridization assay, Analytical Chemistry, 74(14) 3525-3532 (2002).

* cited by examiner

TAPE STRIPPING METHODS FOR ANALYSIS OF SKIN DISEASE AND PATHOLOGICAL SKIN STATE

CROSS-REFERENCE TO RELATED APPLICATION

Under 35 USC §120, this application is a continuation application of U.S. application Ser. No. 10/816,457 filed Mar. 31, 2004, now issued as U.S. Pat. No. 7,183,057. The disclosure of the prior application is considered part of and is incorporated by reference in the disclosure of this application.

BACKGROUND OF THE INVENTION

1. Field of the Invention

The invention relates generally to non-invasive diagnostics methods and more specifically to methods for isolating and analyzing nucleic acids from skin samples.

2. Background Information

Skin diseases represent major health care challenges today. For example, over five million Americans and over one hundred million people worldwide suffer from psoriasis. Detection, diagnosis, and staging of a skin disease is an important aspect of its management. Current diagnostic methods rely mainly on visible observation and biopsies. However, detection methods for skin diseases that rely on visible observation are not effective for diagnosing many skin diseases, and do not detect diseases until after clinical manifestation. Invasive methods such as biopsies, not only are traumatic for a subject being tested, they also increase the risk of infection. Furthermore, invasive methods do not provide an enriched sample of cells on the surface of skin, which are the cells involved in a surface reaction.

Detection and diagnosis of skin disease are important not only for patient management, but also to assess the safety and efficacy of new skin disease therapeutic agents and new skin care products. New therapeutic agents are required for many skin diseases where present therapeutic agents are not fully effective. Furthermore, diagnostic methods provide important information regarding the specific genetic changes underlying a subject's skin disease. Identifying these genetic changes identifies potential drug targets and may be critical in determining whether a person will respond to a particular therapeutic agent.

In addition to assessing new therapeutic agents, detection and diagnosis methods are also important to assess the safety of new skin care products. Skin care products, including cosmetics, are an important part of most people's daily grooming habits. The average adult uses at least seven different skin care products each day. Currently, all commercial skin care products are required to undergo safety testing. These tests take the form of Clinical Acute Primary Irritation and 14-day Cumulative Irritation Protocols followed by Human Repeat Insult Patch Testing (HRIPT) to detect sensitization (contact allergy). Visual analysis is used to determine the test results as described in Richard Berger and James Bowman, A reappraisal of the 21-day cumulative irritancy test in man, J. Toxicol-Cut and Ocular Toxicol 1(2), 101-107 (1982). Therefore, allergic reactions are not detected until they have manifested themselves in a visible reaction.

In addition to issues related to relatively late stages of detection, visible analysis cannot distinguish subtle skin reactions that are difficult to classify as irritant or allergic reactions. This classification distinction is very important because it can be used as the basis for deciding whether to continue to develop a new skin care product. Issues of irritation can be dealt with by reformulation, whereas issues of sensitization (i.e. an allergic reaction) can require more drastic product altering actions due to safety and liability concerns. Therefore, misdiagnosis of irritant dermatitis as allergic dermatitis can block a safe and efficacious skin care product from being available to people who could benefit from it.

SUMMARY OF THE INVENTION

The present invention is based on a non-invasive approach for recovering nucleic acids such as DNA or messenger RNA from the surface of skin via a simple tape stripping procedure that permits a direct quantitative and qualitative assessment of biomarkers. The method provides valuable genetic information, not obtainable using a visible detection method. Furthermore, although tape-harvested RNA is shown to be comparable in quality and utility to RNA recovered by biopsy, the method provides information regarding cells of the outermost layers of the skin that is not obtained using biopsy samples. Finally, the method is far less traumatic than a biopsy.

The method was applied to the analysis of gene expression during irritant contact dermatitis. Using SLS irritation as a model system, the utility of assaying changes in IL-1θ and IL-8 mRNA was tested as an indication of irritant skin reactions. It is show that both sampling methods allow the recovery of RNA, the analysis of which reveals cutaneous irritation. Data is presented that biopsy and tape-harvested RNA are likely derived from different cell populations and that tape harvesting is an efficient method for sampling the epidermis and identifying select differentially regulated epidermal biomarkers. Furthermore, the Examples provided herein illustrate the successful amplification of tape-harvested RNA for hybridization to DNA microarrays. These experiments show no significant gene expression level differences between replicate sites on a subject and minimal differences between a male and female subject. The array generated RNA profiles between normal and 24-hour 1% SLS-occluded skin were compared, and it was observed that SLS treatment resulted in statistically significant changes in the expression levels of more than 1,700 genes. These data illustrate that tape harvesting as a non-invasive method for capturing RNA from human skin for microarray analysis.

Accordingly, provided herein is a method for characterizing skin of a subject, including applying an adhesive tape to a target area of skin in a manner sufficient to isolate an epidermal sample adhering to the adhesive tape, wherein the epidermal sample includes nucleic acid molecules. At least one nucleic acid molecule whose expression is informative of a skin disease or pathological skin state is detected in the epidermal sample. The method of characterizing skin using tape stripping has a number of applications, such as the following: (i) disease classification/subclassification; (ii) monitoring disease severity and progression; (iii) monitoring treatment efficacy; and (iv) prediction of the most beneficial treatment regimen. All of these applications, which themselves represent embodiments disclosed herein, rely on the concept of noninvasive sampling to recover information that is otherwise difficult or impractical to recover (i.e. through the use of biopsies). This information is contained in the RNA of skin cells close to the surface of the skin. In one example, expression of one or more of the genes listed in Table VII, or a combination thereof, is detected in the epidermal sample to characterize the skin. This exemplary method is particularly useful for obtaining information related to an irritated state of the skin.

Certain embodiments of the invention are based in part on the discovery that in subjects afflicted with psoriasis, nucleic acid samples, for example RNA samples, readily obtained from the epidermis of skin areas that contain psoriatic lesions provide information regarding the disease. Accordingly, the present invention provides a non-invasive method for isolating or detecting a nucleic acid molecule from an epidermal sample of a psoriatic lesion of a human subject. The method includes applying an adhesive tape to the psoriatic lesion of the subject in a manner sufficient to isolate an epidermal sample adhering to the adhesive tape. The epidermal sample includes a nucleic acid molecule that is then isolated and/or detected directly. The method of tape stripping psoriatic lesions can be used, for example, to monitor the responsiveness of a psoriasis patient to treatment. Furthermore, the method can be used to identify genes that are predictive of response to therapy.

Other embodiments are based in part on the discovery that for tape stripping of the skin, non-polar, pliable, adhesive tapes, especially pliable tapes with rubber adhesive, are more effective than other types of adhesive tapes. Using pliable tapes with rubber adhesives, as few as 10 or less tape strippings and in certain examples as few as 4 or even 1 tape stripping can be used to isolate and/or detect nucleic acid molecules from the epidermal layer of the skin.

Accordingly, provided herein is a method for isolating and/or detecting a nucleic acid molecule from an epidermal sample from skin, including applying an adhesive tape to a target area of the skin in a manner sufficient to isolate an epidermal sample adhering to the adhesive tape, wherein the epidermal sample comprises nucleic acid molecules, and wherein the tape includes a rubber-based adhesive and is pliable.

In another embodiment, the present invention provides a method for quantitatively assessing gene expression of an amplified nucleic acid in a skin sample that overcomes prior difficulties in such a method. Accordingly, provided herein is a method for detecting a change in gene expression, including applying an adhesive tape to a target area of skin and to an unaffected area of the skin, in a manner sufficient to isolate an epidermal sample adhering to the adhesive tape, wherein the epidermal samples comprise nucleic acid molecules; and for each of the target area sample and the normal area sample, amplifying a target nucleic acid molecule and a control nucleic acid molecule in the same experiment using similar sample volumes and similar probes, wherein a change in the relative amplified levels of the target nucleic acid molecule to the control nucleic acid molecule at the target area versus the normal area is indicative of a change in gene expression of the target nucleic acid molecule at the target area.

In addition, provided herein is a method for detecting a response of a subject to treatment for psoriasis, including applying an adhesive tape to the skin of the subject being treated for psoriasis, in a manner sufficient to isolate an epidermal sample, wherein the epidermal sample includes nucleic acid molecules; and detecting a target nucleic acid molecule in the sample comprising nucleic acid molecules. Expression of the target nucleic acid molecule is informative regarding psoriasis.

In another embodiment the invention provides a kit for isolation and detection of a nucleic acid from an epidermal sample, such as an epidermal sample from a psoriatic lesion or a target area of skin suspected of being inflamed. The kit includes an adhesive tape for performing methods provided herein. Accordingly, in one embodiment, provided herein is a kit that contains a pliable adhesive tape made up at least in part, of a non-polar polymer. In certain aspects, the tape is a rubber-based tape.

DETAILED DESCRIPTION OF THE INVENTION

Figure 1:
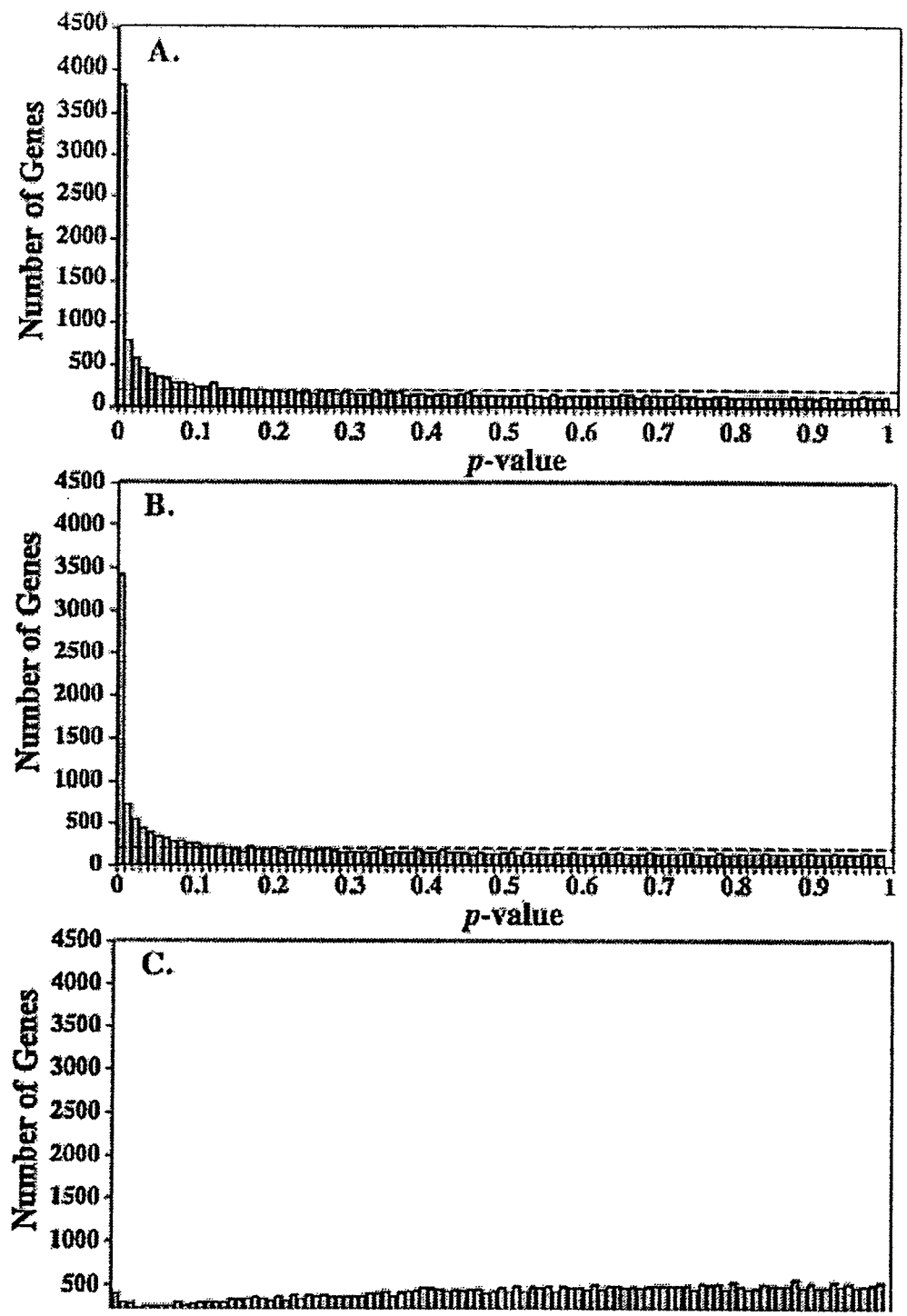
FIG. 1 diagrammatically illustrates the experimental design of the SLS irritation protocol disclosed in further detail in Example 2.

The specification hereby incorporates by reference in their entirety, the files contained on the compact discs filed herewith. Two copies of the compact disc are filed herewith. The compact disc includes a file called "DERM1120.1 Tables.txt" created Feb. 20, 2007, which is 1.54 megabytes in size. Columns 1 and 2 of that spreadsheet file are identical to the Table included in the Appendix.

LENGTHY TABLES

The patent contains a lengthy table section. A copy of the table is available in electronic form from the USPTO web site (http://seqdata.uspto.gov/?pageRequest=docDetail&DocID=US07989165B2). An electronic copy of the table will also be available from the USPTO upon request and payment of the fee set forth in 37 CFR 1.19(b)(3).

The present invention is based on a non-invasive approach for recovering or analyzing nucleic acids such as DNA or RNA, from the surface of skin via a simple tape stripping procedure that permits a direct quantitative and qualitative assessment of pathologic and physiologic biomarkers. Tape-harvested RNA is shown to be comparable in quality and utility to RNA recovered by biopsy. The present method causes little or no discomfort to the patient. Therefore, it can be performed routinely in a physician's office, for example, for point of care testing. Accordingly, provided herein are methods and markers for non-invasive isolation and/or detection of nucleic acids from epidermal samples using tape stripping.

The methods are effective for analysis of skin that is diseased or in a pathological state, such as psoriatic skin or irritated skin. It is shown herein, that the methods can be used to characterize molecular differences in affected skin that visibly appears similar. Furthermore, it is shown herein that the method can be used to monitor response of skin to treatment.

The methods can utilize a $-C_t$ value, which provides useful information regarding gene expression, especially in situations where it is difficult to obtain a "normal" nucleic acid sample, such as in tape stripping methods. Before the present disclosure it was taught that the $-C_t$ value was not being appropriate for gene expression analysis.

Methods of the present invention include a rapid, non-invasive skin-sampling method for obtaining polynucleotides, including DNA and RNA. For example, mRNA is typically isolated in methods wherein gene expression is analyzed. It is illustrated herein that improved isolation of nucleic acid molecules is obtained using pliable tape with a rubber adhesive.

Accordingly, in methods provided herein, an epidermal sample is obtained by tape stripping the skin, which involves applying an adhesive tape to the skin in a manner sufficient to isolate an epidermal sample adhering to the tape that includes nucleic acid molecules. Tape stripping methods provided herein, for example a single application of 4 individual tapes, do not result in glistening of uninvolved skin, and thus do not bare the viable epidermis. In contrast, a shave biopsy is expected to include not only cells of the epidermis (primarily keratinocytes and melanocytes and immune cells) but fibroblasts from the upper dermis as well.

A "biomolecule" is a specific binding pair member found in nature, or derived from a molecule found in nature. As used herein, the term "specific binding pair member" refers to a molecule that specifically binds or selectively hybridizes to, or interacts with, another member of a specific binding pair. Specific binding pair members include, for example, analytes and biomolecules.

"Nucleic acid" means DNA, RNA, single-stranded, double-stranded or triple stranded and any chemical modifications thereof. Virtually any modification of the nucleic acid is contemplated. A "nucleic acid" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

The term "polypeptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A polypeptide of the invention contains at least about six amino acids, usually contains about ten amino acids, and can contain fifteen or more amino acids, particularly twenty or more amino acids. It should be recognized that the term "polypeptide" is not used herein to suggest a particular size or number of amino acids comprising the molecule, and that a peptide of the invention can contain up to several amino acid residues or more. A protein is a polypeptide that includes other chemical moieties other than amino acids, such as phosphate groups or carbohydrate moiety.

A "skin lesion" is a wound on the skin or injury to the skin. A "plaque" is a flattish, raised patch on the skin. "Scales" are thin flakes on the skin surface.

Throughout this application, the term "proliferative skin disorder" refers to a disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "sample" refers to any preparation derived from skin of a subject. For example, a sample of cells obtained using the non-invasive method described above can be used to isolate polynucleotides, polypeptides, or lipids, preferably polynucleotides and polypeptides, most preferably nucleic acid molecules, such as polynucleotides, for the methods of the present invention. Samples for the present invention, typically are taken from a skin lesion, that is suspected of being the result of a disease or a pathological state, such as psoriasis or dermatitis. The samples are taken of the skin surface of the suspicious lesion using non-invasive skin sampling methods discussed herein.

The term "skin" refers to the outer protective covering of the body, consisting of the corium and the epidermis, and is understood to include sweat and sebaceous glands, as well as hair follicle structures. Throughout the present application, the adjective "cutaneous" can be used, and should be understood to refer generally to attributes of the skin, as appropriate to the context in which they are used. In a preferred embodiment, the skin is mammalian skin. In an illustrative embodiment the skin is human skin.

The tape stripping methods provided herein typically involve applying an adhesive tape to the skin of a subject and removing the adhesive tape from the skin of the subject one or more times. In certain examples, the adhesive tape is applied to the skin and removed from the skin about one to ten times. Alternatively, about ten adhesive tapes can be applied to the skin and removed from the skin. These adhesive tapes are then combined for further analysis. Accordingly, an adhesive tape can be applied to and removed from a target site 10, 9, 8, 7, 6, 5, 4, 3, 2, or 1 time, and/or 10, 9, 8, 7, 6, 5, 4, 3, 2, or 1 adhesive tape can be applied to and removed from the target site. In one illustrative example, the adhesive tape is applied to the skin between about one and eight times, in another example, between one and five times, and in another illustrative example the tape is applied and removed from the skin four times.

For the tape strippings, the same strip of tape can be repeatedly applied to, and removed from, a target site, such as a psoriatic lesion. However, in illustrative embodiments a fresh piece of adhesive tape is sequentially applied to a target site of the skin. The individual tape strips used to sample a site can then be combined into one extraction vessel for further processing such as nucleic acid extraction. In one illustrative example, the adhesive tape is applied to the skin between about one and eight times, in another example, between one and five times, and in another illustrative example the tape is applied and removed from the skin four times.

Factors such as the flexibility, softness, and composition of the adhesive tape used, the time the tape is allowed to adhere to the skin before it is removed, the force applied to the tape as it is applied to the skin, the prevalence of a gene product being analyzed, the disease status of the skin, and patient/patient variability are typically taken into account in deciding on a protocol useful for a particular tape stripping method in order to assure that sufficient nucleic acids are present in the epidermal sample. A tape stripped sample includes, but may not be limited to, tissues that are restricted to the surface of skin and preferentially recovers vellus hair follicles and cells lining sebaceous, eccrine, and sweat ducts (i.e. the adnexal structures associated with the stratum corneum and epidermis), as well as corneocytes. Tape stripping is stopped before viable epidermis is exposed by ceasing tape stripping before the tissue glistens. Therefore, the tape stripping method is considered a "noninvasive" method. Tape stripping sufficient to isolate an epidermal sample is tape stripping that is performed on the skin sufficient times to obtain an RNA sample, wherein the tape stripping is stopped before the tissue glistens (i.e. becomes shiny, appears "moistened" or reflective).

Certain aspects of the invention, which themselves are embodiments of the invention, are based in part on the discovery that non-polar, pliable adhesive tapes, especially plastic-based adhesive tapes, are more effective for obtaining nucleic acid samples from the skin than other types of adhesive tapes. Using non-polar, pliable adhesive tapes as few as 10 or less tape strippings and in certain examples as few as 4 or even 1 tape stripping can be used to obtain a nucleic acids that can be analyzed. The method can be used as part of various embodiments provided herein, to isolate an RNA sample from the epidermis of skin, for gene expression analysis.

Accordingly, provided herein is a method of detecting expression of genes in the skin, including applying an adhesive tape to a target area of the skin in a manner sufficient to isolate an epidermal sample adhering to the adhesive tape, wherein the epidermal sample comprises nucleic acid molecules, wherein the tape comprises a rubber adhesive, and wherein the tape is pliable. The nucleic acid molecules in the epidermal sample are then detected. The nucleic acid molecules, in certain examples, are applied to a microarray to detect the nucleic acid molecules.

In another embodiment, provided herein is a method for isolating a nucleic acid molecule from an epidermal sample from skin, including applying an adhesive tape to a target area of the skin in a manner sufficient to isolate an epidermal sample adhering to the adhesive tape, wherein the epidermal sample includes nucleic acid molecules, wherein the tape includes a non-polar polymer adhesive, and wherein the tape is pliable. A nucleic acid molecule is then isolated from the epidermal sample. In illustrative examples, the non-polar polymer adhesive is a rubber-based adhesive.

The rubber based adhesive can be, for example, a synthetic rubber-based adhesive. The rubber based adhesive in illustrative examples, has high peel, high shear, and high tack. For example, the rubber based adhesive can have a peak force tack that is at least 25%, 50%, or 100% greater than the peak force tack of an acrylic-based tape such as D-squame™. D-squame™ has been found to have a peak force of 2 Newtons, wherein peak force of the rubber based adhesive used for methods provided herein, can be 4 Newtons or greater. Furthermore, the rubber based adhesive can have adhesion that is greater than 2 times, 5 times, or 10 times that of acrylic based tape. For example, D-squame™ has been found to have adhesion of 0.0006 Newton meters, whereas the rubber based tape provided herein can have an adhesion of about 0.01 Newton meters using a texture analyzer. Furthermore, in certain illustrative examples, the adhesive used in the methods provided herein has higher peel, shear and tack than other rubber adhesives, especially those used for medical application and Duct tape.

In addition to having higher peel, shear, and tack, the rubber-based adhesive is more hydrophobic than acrylic adhesives. Furthermore, the rubber based adhesive in illustrative examples is inert to biomolecules and to chemicals used to isolate biomolecules, especially nucleic acids such as DNA and RNA. Finally, the adhesive can be relatively soft compared to other tapes such as D-squame™.

The rubber-based adhesive is on a support, typically a film, that makes the tape pliable and flexible. In certain aspects, the tape can be soft and pliable. "Pliable" tape is tape that is easily bent or shaped. "Soft and pliable" tape is tape that is easily bent or shaped and yields readily to pressure or weight. The film can be made of any of many possible polymers, provided that the tape is pliable and can be used with a rubber adhesive. The thickness can be varied provided that the tape remains pliable. For example, the tape can be 0.5 mil to 10 mil in thickness, 1.0 to 5.0 mil in thickness. In one example, the tape contains a rubber adhesive on a 3.0 mil polyurethane film. For example the film can be a polyurethane film such as skin harvesting tape (Product No. 90068) available from Adhesives Research, Inc (Glen Rock, Pa.).

The Examples illustrate tape stripping methods provided herein. Generally, before contacting a skin site with adhesive tape, a skin site to be stripped is cleaned, for example using an antiseptic cleanser such as alcohol. Next, tape is applied to a skin site with pressure. Pressure can be applied for a fraction of a second, but can be applied for between 1 second and 5 minutes, typically between 10 seconds and 45 seconds. In certain illustrative examples, tape is applied for 30 seconds for each tape stripping. It will be understood that the amount of pressure applied to a skin site and the length of time for stripping can be varied to identify ideal pressures and times for a particular application. Generally, pressure is applied by manually pressing down the adhesive tape on the skin, however, objects, such as blunt, flat objects can be used to assist in applying the tape to the skin, especially for areas of the skin from which it is more difficult to obtain nucleic acid samples from skin, such as uninvolved skin of a subject afflicted with psoriasis.

Virtually any size and/or shape of adhesive tape and target skin site size and shape can be used and analyzed, respectively, by the methods of the present invention. For example, adhesive tape can be fabricated into circular discs of diameter between 10 millimeters and 100 millimeters, for example between 15 and 25 millimeters in diameter. The adhesive tape can have a surface area of between about 50 mm$^2$ and 1000 mm$^2$, between about 100 mm$^2$ to 500 mm$^2$ or about 250 mm$^2$.

As illustrated in the Examples provided herein, biopsy and tape stripping may not be equivalent sampling methods and therefore should not be expected to yield identical results. Not intended to be limited by theory, tape stripping, also referred to as "tape harvesting," is restricted to the skin surface and therefore may preferentially recover vellus hair follicles and cells lining sebaceous, eccrine and sweat ducts as well as corneocytes (not predicted to contain RNA). Tape stripping methods provided herein, which typically utilize 10 or less tape strippings, for example a single application of 4 individual tapes, do not result in glistening of uninvolved skin and thus do not bare the viable epidermis. Thus, tape stripping methods provided herein, provide an epidermal sample. In contrast, a shave biopsy, in which a scalpel blade is use to slice a thin piece of skin from the surface (and which typically results in bleeding but does not require suturing), is expected to include not only cells of the epidermis (primarily keratinocytes and melanocytes and immune cells) but fibroblasts from the upper dermis. The potential enrichment of surface epidermis conveyed by tape stripping compared to a shave biopsy can be appreciated by considering that the surface area of a tape is 284 mm$^2$, while the surface area of a 2×2 mm shave biopsy is 4 mm$^2$. Thus, tape-harvested cells represent an enrichment of a sub-population of cells found in a shave biopsy. The data presented in Tables I and IV support the hypothesis that tape and biopsy-harvested RNA are derived from different cell populations.

The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

The skin sample obtained using the tape stripping method includes, epidermal cells including cells comprising adnexal structures. In certain illustrative examples, the sample includes predominantly epidermal cells, or even exclusively epidermal cells. The epidermis consists predominantly of keratinocytes (>90%), which differentiate from the basal layer, moving outward through various layers having decreasing levels of cellular organization, to become the cornified cells of the stratum corneum layer. Renewal of the epidermis occurs every 20-30 days in uninvolved skin. Other cell types present in the epidermis include melanocytes, Langerhans cells, and Merkel cells. As illustrated in the Examples herein, the tape stripping method of the present invention, is particularly effective at isolating epidermal samples.

Nucleic acids can be isolated from the lysed cells and cellular material by any number of means well known to those skilled in the art. For example, a number of commercial products available for isolating polynucleotides, including but not limited to, RNeasy™ (Qiagen, Valencia, Calif.) and TriReagent™ (Molecular Research Center, Inc, Cincinnati, Ohio) can be used. The isolated polynucleotides can then be tested or assayed for particular nucleic acid sequences, including a polynucleotide encoding a cytokine. Methods of detecting a target nucleic acid within a nucleic acid sample are well known in the art, and can include microarray analysis, as discussed in more detail herein.

In another embodiment, provided herein is a non-invasive method for identifying a predictive skin marker for response to treatment for a disease or pathological state, including: applying an adhesive tape to the skin of a subject afflicted with the disease or pathological state at a first time point, in a manner sufficient to isolate an epidermal sample including nucleic acid molecules and treating the subject for the disease or pathological state. It is then determined whether the disease or pathological state has responded to the treatment, and if so, whether expression of a nucleic acid molecule in the epidermal sample is predictive of response to treatment.

Expression of a nucleic acid molecule in the epidermal sample is predictive of response to treatment if expression of the nucleic acid molecule at the first time point is different in subjects that respond to treatment compared to subjects that do not respond to treatment. It will be understood that a variety of statistical analysis can be performed to identify a statistically significant association between expression of the nucleic acid molecule and response of the subject to the treatment. For example, expression of the nucleic acid in certain examples is elevated, in subjects that will not respond to treatment. Furthermore, expression of the nucleic acid can predict a level of response to treatment, for example partial or temporary response to treatment versus a full response.

In another embodiment, provided herein is a non-invasive method for predicting response to treatment for a disease or pathological state, including applying an adhesive tape to the skin of a subject afflicted with the disease or pathological state in a manner sufficient to isolate an epidermal sample that includes nucleic acid molecules. A target nucleic acid molecule is detected in the epidermal sample, whose expression is indicative of a response to treatment, thereby predicting response to treatment for the disease or pathological state.

The disease for embodiments directed at identifying a predictive skin marker, or predicting response to treatment by detecting a predictive skin marker, also referred to in these embodiments as a target nucleic acid molecule, can be virtually any skin disease. For example, the skin disease can be psoriasis or dermatitis, such as irritant contact dermatitis or allergic contact dermatitis. In aspects where the disease is psoriasis, the treatment can be, for example, a topical treatment, phototherapy, a systemic medication, or a biologic. Specific treatments are provided in Table VIII.

Samples from a tissue can be isolated by any number of means well known in the art. Invasive methods for isolating a sample include the use of needles, for example during blood sampling, as well as biopsies of various tissues. Due to the invasive nature of these techniques there is an increased risk of mortality and morbidity. The methods and kits of the present invention use a non-invasive sampling method to obtain a skin sample. In certain examples, these methods are used along with conventional methods, such as a skin biopsy, to provide additional information.

As mentioned above, tape-harvested cells appear to represent an enrichment of a sub-population of cells found in a shave biopsy. Accordingly, in certain aspects, in addition to a tape stripping method provided herein, a biopsy can be taken at the site of tape stripping, such as a psoriatic lesion site, or at another skin site. Nucleic acid molecules from the biopsy can be isolated and analyzed. Analysis of the biopsy data can be combined with analysis of data from a tape stripping method to provide additional information regarding the psoriatic lesion.

In certain aspects a nucleic acid molecule from uninvolved epidermal tissue is obtained by applying an adhesive tape to skin of the subject in a manner sufficient to isolate an epidermal sample adhering to the adhesive tape, wherein the epidermal sample includes nucleic acid molecules and wherein the skin is unaffected by a disease to be tested. Then a nucleic acid molecule is isolated and detected from the epidermal sample of the unaffected skin.

In certain aspects, the uninvolved skin can be from the upper arm or the upper back. These sites appear to provide relatively plentiful quantities of nucleic acid molecules using tape strippings. For example, tape stripping can be performed on uninvolved skin over the deltoid or upper back over the scapular spine and the periauricular region. Tape stripping generally involves the skin surface and therefore may preferentially recover vellus hair follicles and cells lining sebaceous, eccrine and sweat ducts (i.e. adnexal structures) as well as corneocytes (not predicted to contain RNA).

Certain embodiments provided herein, are based in part on the discovery that the expression of certain genes can be used to monitor response to therapy. Accordingly, in another embodiment, provided herein is a method for monitoring a response of a human subject to treatment for a disease or pathological state, including applying an adhesive tape to the skin of the subject being treated for the disease or pathological state at a first time point and at least a second time point, in a manner sufficient to isolate an epidermal sample adhering to the adhesive tape at the first time point and at the second time point. The epidermal sample includes a nucleic acid molecule, wherein a change in expression of the nucleic acid molecule between the first time point and the second time point is indicative of a change in the disease or pathological state.

In a related embodiment, provided herein is a method for detecting a response of a subject to treatment for a disease or pathological state, comprising: treating the subject for a skin disease or pathological skin state; applying an adhesive tape to the skin of the subject in a manner sufficient to isolate an epidermal sample, wherein the epidermal sample includes nucleic acid molecules; and detecting a target nucleic acid molecule in the sample comprising nucleic acid molecules. Expression of the target nucleic acid molecule is informative regarding the disease or pathological state. Therefore, the method identifies a response of the subject to treatment for the disease or pathological state.

The detection can be a qualitative detection of whether the target gene is expressed, but is typically a quantitative expression level determination. The method can be performed both prior to treatment and after treatment. In one aspect, the method is performed after treatment, but before a change in disease or pathological state is observed visually.

Time points for the monitoring and response-to-treatment methods provided herein, can include any interval of time, but are typically at least 2 weeks, and more typically at least 1 month apart. For certain embodiments, time points are 2 months, 3 months, 6 months, 1 year, or 2 years apart. Samples can be taken at any number of time points, including 2, 3, 4, 5, etc. time points. Comparison of expression analysis data from different time points can be performed using any of the known statistical methods for comparing data points to assess differences in the data, including time-based statistical methods such as control charting. The disease or pathological state can be identified in the time series, for example, by comparing expression levels to a cut-off value, or by comparing changes in expression levels to determine whether they exceed a cut-off change value, such as a percent change cut-off value. In certain aspects, the first time point is prior to treatment, for example, prior to administration of a therapeutic agent, and the second time point is after treatment.

The disease or pathological state can be virtually any skin disorder. For example, the skin disorder can be psoriasis, dermatitis, or a skin infection, an allergic reaction, hives, seborrhea, irritant contact dermatitis, allergic contact dermatitis, hidradenitis suppurative, allergic purpura. Pityriasis rosea, Dermatitis herpetiformis, erythema nodosum, erythema multiforme, lupus erythematosus, a bruise, actinic keratoses, keloid, lipoma, a sebaceous cyst, a skin tag, xanthelasma, basal cell carcinoma, squamous cell carcinoma, or Kaposi's sarcoma. In certain aspects, the disease or pathological state is other than melanoma.

The change in expression levels of at least one nucleic acid molecule can be an increase or decrease in expression. Furthermore, depending on the particular nucleic acid and the particular disease or pathological state, an increase or decrease can indicate a response to treatment, or a lack of response. For example, the nucleic acid can encode a protein such as CD2, TNFI, or IFN$\gamma$, and a decrease in expression at the second time point as compared to the first time point is indicative of positive response to treatment for psoriasis. As another example, the method can detect a decrease in expression of TNFI, IFN$\gamma$, IL-12B, NPF, or IL-23B, wherein a decrease in expression is indicative of response to treatment for psoriasis. As another example, the method detects expression of a keratin 10, keratin 16, or keratin 17 gene product, wherein an increase in expression is indicative of response to treatment for dermatitis, such as irritant dermatitis.

In other aspects of this method, a population of genes are detected. For these aspects, the method can be performed using a microarray.

In another embodiment, provided herein is a method for characterizing skin of an animal subject, including applying an adhesive tape to a target area of skin in a manner sufficient to isolate an epidermal sample adhering to the adhesive tape, wherein the epidermal sample includes nucleic acid molecules. A nucleic acid molecule whose expression is informative of a skin disease or pathological skin state is then detected in the epidermal sample. For example, expression of a gene listed in Table VII on the compact disk filed herewith can be detected in the epidermal sample to characterize the skin for an irritated state. The Appendix included herewith, includes the list of genes found on Table VII.

The method of characterizing skin has a number of applications, such as the following: (i) disease classification/sub-classification; (ii) monitoring of disease severity and progression; (iii) monitoring of treatment efficacy; and (iv) prediction of most beneficial treatment regime. All of these applications, which themselves represent embodiments disclosed herein, rely on the concept of noninvasive sampling to recover information that is otherwise difficult or impractical to recover (i.e. through the use of biopsies). This information is contained in the RNA of skin cells close to the surface of the skin.

In one aspect of the method for characterizing skin, a test agent is applied to the target area before the adhesive tape is applied. Accordingly, in one embodiment, provided herein is a method for determining the effect of an agent, such as a test agent, on skin, including: contacting a target area of the skin with the agent and applying an adhesive tape to the target area of the skin in a manner sufficient to isolate an epidermal sample adhering to the adhesive tape, wherein the epidermal sample includes nucleic acid molecules. Nucleic acid molecules are optionally isolated from the epidermal sample to determine an expression profile for the target site of the skin. The expression profile is indicative of a state of the skin, thereby providing a determination of the effect of the agent on the skin. The expression profile can be obtained using a microarray, as discussed in more detail herein.

A number of embodiments and aspects provided herein are directed at testing the effects of an agent, such as a test agent, on the skin. In these embodiments and aspects the agent can be applied until or before any visual symptoms become evident. For example, the agent can be applied for between 1 second to 12 hours to a skin site, more specifically the test agent can be applied between about 0.5 and 2 hours before it is removed and tape stripping is performed on the skin site contacted with the agent.

In certain aspects, after exposure to a test agent, a test site is interrogated by tape stripping and a molecular profile generated to classify an agent. For example, the agent can be classified as highly irritating or corrosive without damage to the skin. Furthermore, the agent can be classified as a specific type of irritant, for example a detergent or a dye.

The tape stripping according to these aspects of the invention is performed to obtain an epidermal as disclosed in more detail herein. For example, to obtain the epidermal sample, an adhesive tape can be applied and removed from the skin about one to ten times, as discussed in more detail herein.

Methods performed herein for determining the effects of a test agent on skin can be performed as part of a process testing the safety and/or efficacy of the test agent. For example, the testing can be part of testing performed as part of the approval process for marketing the test agent. As part of methods that analyze the effects of an agent, the agent is typically applied on the skin (i.e. topically). The agent can be formulated as a paste, an ointment, a lotion, or a shake lotion, for example. In certain aspects, the agent is a placebo.

In another aspect the invention provides a method of screening for agents or identifying agents that may cause skin disease or a pathological skin state, or which may be used to treat skin disease or a pathological skin state. In this aspect, for example, cells of the skin, such as epidermal cells, including keratinocytes and melanocytes, or dermal cells, such as fibroblasts, are contacted with a test agent. The expression of markers of the skin disease or pathological skin state is then detected.

The conditions under which contact is made are variable and will depend upon the type of agent, the type and amount of cells in the skin to be tested, the concentration of the agent in the sample to be tested, as well as the time of exposure to the agent. It will be understood that routine experimentation can be used to optimize conditions for contacting skin with the agent.

An "agent" as used herein is used broadly herein to mean any molecule to which skin is exposed. The term "test agent" or "test molecule" is used broadly herein to mean any agent that is being examined for an effect on skin in a method of the invention. For example, the agent can be a biomolecule or a small organic molecule. In illustrative examples, the agent is a peptide, polypeptide, or protein, a peptidomimetic, an oligosaccharide, a lipoprotein, a glycoprotein or glycolipid, a chemical, including, for example, a small organic molecule, which can be formulated as a drug or other pharmaceutical agent, or a nucleic acid, such as a polynucleotide.

In certain aspects, the agent is a skin care product. Skin care products are products designed to maintain healthy skin. They include astringents, moisturizers, and sunscreens. Skin care products as used herein, include personal care products, which are products that help keep skin and hair clean and fresh smelling include skin cleansers, shampoos, conditioners, and deodorants/antiperspirants. Furthermore, skin care products include cosmetics, which are skin care products designed to color and adorn a surface of the body, such as the skin. Therefore, skin care products, as used herein, includes, for example, fragrances, astringents, moisturizers, sunscreens, skin cleansers, hair care items, deodorants/antiperspirants, colored cosmetics, hair cosmetics, and nail cosmetics. Cosmeceuticals are skin care products designed to go beyond strictly coloring and adorning the skin. These products actually improve the functioning of the skin and may be helpful in preventing premature aging. Examples of these substances are alpha hydroxy acids, such as glycolic acid, beta hydroxy acid, and salicylic acid. These hydroxy acids increase skin exfoliation making aging skin appear smoother and feel softer. Some vitamins, such as vitamin A (retinal), improve the appearance of aging skin by making the skin function better.

Skin care products can cause dermatitis in some individuals. It is important to distinguish dermatitis that is the result of irritated skin from dermatitis that is caused by an allergy, because allergic contact dermatitis is a more severe condition. Presently, methods are not available for distinguishing allergic contact dermatitis from irritant contact dermatitis.

The Examples provided herein demonstrate using SLS irritation as a model system, the utility of assaying changes in IL-1+ and IL-8 mRNA has been tested as an indication of irritant skin reactions. The array generated RNA profiles between normal and 24-hour 1% SLS-occluded skin were compared, and it was observed that SLS treatment resulted in statistically significant changes in the expression levels of more than 1,700 genes. These data not only identify markers of irritated skin, but also illustrate that tape harvesting as a non-invasive method for capturing RNA from human skin for microarray analysis.

Accordingly, provided herein is a method for characterizing skin of an animal subject, including: applying an adhesive tape to a target area of skin suspected of including irritated skin in a manner sufficient to isolate an epidermal sample adhering to the adhesive tape, wherein the epidermal sample includes nucleic acid molecules. A nucleic acid molecule expressed from a gene listed in Table VII, which are identical to the genes listed in the second column of the Table of the Appendix, or a combination thereof, is then detected in the epidermal sample, wherein expression of the nucleic acid molecule is altered in irritated skin, thereby characterizing skin of the subject.

In another embodiment, provided herein is a method for diagnosing a skin rash as an infection by tape stripping the rash using methods disclosed herein. Nucleic acids isolated from the site of the rash can be analyzed for the presence of nucleic acids of a microbe, wherein the presence of nucleic acids of the microbe is indicative of an infection by the microbe. The microbe can be, for example, a fungus, *staphylococcus*, or *streptococcus*.

In another embodiment, provided herein is a method for distinguishing an irritant contact dermatitis (ICD) from an allergic contact dermatitis (ACD) in a subject, including: —applying an adhesive tape to an area of skin afflicted with dermatitis in a manner sufficient to isolate an epidermal sample adhering to the adhesive tape, wherein the epidermal sample comprises nucleic acid molecules. Then, determining expression levels of a gene associated with ICD or ACD, thereby distinguishing ICD with ACD. Before expression levels are determined ribonucleic acid RNA molecules can be optionally isolated from the epidermal sample.

In certain aspects, expression of more than one nucleic acid molecule can be detected to characterize the skin, for example to distinguish ICD from ACD. As illustrated in the examples, expression of about 1700 genes is altered in irritated versus uninvolved skin. Therefore, changes of skin state from normal to an irritated state, are accompanied by changes in at least 1700 genes. Therefore, in certain examples, methods provided herein characterize skin by analyzing expression of 2 or more, 5 or more, 10 or more, 25 or more, 50 or more, 100 or more, 500 or more, 1000 or more, 1500 or more, or all of the genes listed in Tables VII (Provided on the compact disk provided herewith as file 6392999.xls) or the Table provided in the Appendix, which includes an identical list of genes as Table VII. In certain examples, expression is detected for a gene listed in Table VI, which lists 100 genes identified in the studies disclosed herein, with the most dramatic expression changes in irritated skin. For example, a detected nucleic acid can be an expression product of the IL-8 gene. In another example, the nucleic acid detected is the keratin 10, 16 and/or 17 gene, in illustrative examples the keratin 16 and/or 17 gene, wherein a down-regulation of the nucleic acid in a tape stripped skin is indicative of irritated skin.

The Examples provided herein illustrate the successful amplification of tape-harvested nucleic acids for hybridization to nucleic acid microarrays. These experiments show no significant gene expression level differences between replicate sites on a subject and minimal differences between a male and female subject.

Accordingly, in another embodiment, the present invention provides a method for identifying an expression profile indicative of a disease or pathological state of a human subject, including applying an adhesive tape to an area of skin afflicted with the disease or pathological state in a manner sufficient to isolate an epidermal sample adhering to the adhesive tape, wherein the epidermal sample includes nucleic acid molecules, and applying the nucleic acid molecules to a microarray. Nucleic acid molecules can optionally be isolated from the epidermal sample before being applied to the microarray. Expression levels of at least 10 genes is then determined using the microarray; wherein an altered expression level for at least 2, 3, 4, 5, 6, 7, 8, 9, or each of the at least 10 genes as compared with expression in an epidermal sample from a normal sample identifies skin afflicted with the disease or pathological state, thereby identifying the expression profile indicative of the disease or pathological state.

In another embodiment, provided herein is a method for identifying an expression profile indicative of a disease or pathological state of a human subject. The method includes applying an adhesive tape to an area of skin afflicted with the disease or pathological state in a manner sufficient to isolate an epidermal sample adhering to the adhesive tape; and applying RNA molecules from the sample to a microarray to determine an expression pattern for the disease or pathological skin state sample and the unaffected sample. A difference in the expression profile is indicative of an expression profile of a disease or pathological state skin. The RNA molecules can optionally be isolated from the epidermal sample before being applied to the microarray.

In certain aspects, the disease or pathological state is dermatitis. In other aspects, the disease or pathological state is psoriasis.

In embodiments where expression of more than 1 gene is analyzed, the detection can be performed using a microarray. For example, the microarray can include an array of probes, for example, directed to 2 or more, 10 or more, 25 or more, 50 or more, 100 or more, 500 or more, 1000 or more, 1500 or more, 1700 or more, or all of the genes listed in Table VII, or the subset of genes listed in Table VI. The microarrays form another embodiment of the invention. Accordingly, in another embodiment, provided herein is a microarray that includes an array of probes, for example, directed to 2 or more, or more, 25 or more, 50 or more, 100 or more, 500 or more, 1000 or more, 1500 or more, 1700 or more, or all of the genes listed in Table VII, or the subset of genes listed in Table VI.

For microarray expression analysis, approximately 0.1 to 1 milligram, typically 1 to 10 nanograms of RNA are isolated from an epidermal sample, for example obtained using a tape stripping method disclosed herein. Isolated RNA is then amplified and used for hybridization to probes on a biochip. Amplification typically results in a total of at least 1 microgram, and more typically at least 20 micrograms of amplified nucleic acid. For example, amplification can be performed using a MessageAmp™ aRNA kit (Ambion Inc.). Isolated RNA can be biotin labeled before contacting the biochip such that binding to the target array can be detected using streptavidin. The probes bind specifically to one or more of the genes listed in Tables VII and VIII, or a complement thereof.

Hybridization of amplified nucleic acids to probes on a microarray is typically performed under stringent hybridization conditions. Conditions for hybridization reactions are well known in the art and are available from microarray suppliers. For example, hybridization of a nucleic acid molecule with probes found on a microarray can be performed under moderately stringent or highly stringent physiological conditions, as are known in the art. For example, as illustrated in the Example section herein, hybridizations on a microarray can be carried out according to manufacturer's (Affymetrix) instructions. For example, hybridization can be carried out for 16 hours at 45° C. in a hybridization buffer composed of 100 mM MES, 1 M [Na+], 20 mM EDTA, 0.01% Tween 20. Washes can be carried out, for example, in a low stringency buffer ((6×SSPE, 0.01% Tween 20) at 25° C. followed by a high stringency buffer (100 mM MES, 0.1M [Na+], 0.01% Tween 20) at 50° C. Another example of progressively higher stringency conditions that can be used in the methods disclosed herein are as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

As illustrated in the Examples provided herein, the manufacture and use of biochips such as those involving microarrays, also known as bioarrays, are known in the art. (For reviews of Biochips and microarrays see, e.g., Kallioniemi O. P., "Biochip technologies in cancer research," *Ann Med, March;* 33(2):142-7 (2001); and Rudert F., "Genomics and proteomics tools for the clinic," Curr Opin. Mol. Ther., December; 2(6):633-42 (2000)) Furthermore, a number of biochips for expression analysis are commercially available (See e.g., microarrays available from Sigma-Genosys (The Woodlands, Tex.); Affymetrix (Santa Clara, Calif.), and Full Moon Biosystems (Sunnyvale, Calif.)).

Such microarrays can be analyzed using blotting techniques similar to those discussed below for conventional techniques of detecting polynucleotides and polypeptides, as illustrated in the Examples provided herein. Detailed protocols for hybridization conditions are available through manufacturers of microarrays. Other microfluidic devices and methods for analyzing gene expression, especially those in which more than one gene can be analyzed simultaneously and those involving high-throughput technologies, can be used for the methods of the present invention. A microarray can provide for the detection and analysis of at least 10, 20, 25, 50, 100, 200, 250, 500, 750, 1000, 2500, 5000, 7500, 10,000, 12,500, 25,000, 50,0000, or 100,000 genes.

Quantitative measurement of expression levels using bioarrays is also known in the art, and typically involve a modified version of a traditional method for measuring expression as described herein. For example, such quantitation can be performed by measuring a phosphor image of a radioactive-labeled probe binding to a spot of a microarray, using a phosphohor imager and imaging software.

Currently, primary irritation protocols are designed to detect highly irritating and corrosive materials through limited patch testing. However, some of clinical sequelae associated with these protocols can take days or weeks to manifest themselves. A testing protocol would be far superior if a substance could be applied for a shorter period of time, for example 0.5-2 hours, and removed before any visual symptoms become evident. If a test site could be interrogated by tape stripping and a molecular profile generated that could classify an agent as highly irritating or corrosive without damage to the skin, this would be an extremely useful and valuable test. Accordingly, presented herein is a method for predicting subclinical irritant skin reactions, and the rapid prediction of irritant skin reactions before the manifestation of clinical symptoms. These methods are useful to test the effects of an agent, such as a test agent on the skin.

Methods provided herein can be used to characterize the outer surface of virtually any animal. In certain aspects, the methods are used to characterize and/or otherwise analyze the outer surface of a body of a mammalian subject. For example, the methods can be used to tape strip rodents, such as mice, as well as, rabbits, or pigs. In illustrative examples, the methods are used to analyze human skin.

Certain embodiments of the invention relate specifically to psoriasis and are based in part on the discovery that nucleic acid samples, for example RNA samples, from the epidermis of the skin can be obtained from psoriatic lesions using tape stripping in psoriasis patients. Psoriasis is a chronic, genetic, noncontagious skin disorder that appears in many different forms and can affect any part of the body, including the nails and scalp. Psoriasis is categorized as mild, moderate, or severe, depending on the percentage of body surface involved and the impact on the patient's quality of life (QoL). Psoriasis may be one of several types: plaque psoriasis, pustular psoriasis, erythrodermic psoriasis, guttate psoriasis or inverse psoriasis. As indicated herein, methods for staging provided herein, assist in determining the severity and type of psoriasis.

Although psoriasis may affect any area of the body, it is most commonly found on the scalp, elbows, knees, hands, feet, and genitals. Plaque psoriasis, the most common type of the disease, is characterized by raised, thickened patches of red skin covered with silvery-white scales. Other types of psoriasis are characterized by different signs and symptoms. For example, pustular psoriasis is characterized by pus-like blisters, erythrodermic psoriasis is characterized by intense redness and swelling of a large part of the skin surface, guttate psoriasis is characterized by small, drop-like lesions, and inverse psoriasis is characterized by smooth red lesions in the folds of the skin. Method provided herein help to distinguish between the various types of psoriasis.

Although psoriasis may be almost unnoticeable in its early stages, subjects often report an itching and/or burning sensation as the disease progresses. In particular, plaque psoriasis usually begins with small red bumps on the skin that progress to bigger, scaly patches that may become itchy and uncomfortable. As the scales accumulate, pink to deep red plaques with a white crust of silvery scales appear on the skin surface.

The lesion suspected of being a psoriatic lesion can be the result of Koebner's phenomenon. In this phenomenon psoriatic lesions appear at the site of injury, infection or other skin problem. The lesion may mark the initial onset of psoriasis, or may be a new lesion in an existing case of psoriasis. In certain examples, the site of tape stripping can be on the fingernails or toenails, which are known sites of psoriasis that can be involved in psoriatic arthritis.

A "psoriasis skin marker" is a gene whose expression level is different between skin samples at the site of a psoriatic lesion and skin samples of uninvolved skin. Therefore, expression of a psoriasis skin marker is related to, or indicative of, psoriasis. As discussed herein, all of the psoriasis skin markers illustrated herein exhibit increased expression in psoriatic lesion versus non-psoriatic skin cell. Methods provided herein, for examples methods using microarrays to perform gene expression analysis using samples obtained from tape stripped skin, can be used to identify additional psoriasis markers. The expression of these psoriasis makers can increase or decrease in psoriatic lesions.

Many statistical techniques are known in the art, which can be used to determine whether a statistically significant difference in expression is observed at a 90% or preferably a 95% confidence level. In certain examples, a greater than 4 fold increase or decrease can be used as a cut-off value for identifying a psoriasis skin marker. The Examples provided herein illustrate the identification of psoriasis skin markers. In certain examples, there is at least a four-fold difference in levels between a skin sample from a psoriatic lesion and non-lesional skin. Psoriasis skin markers identified herein include CD2, interferon K (IFNK), and tumor necrosis factor I (TNFI).

Accordingly, the present invention provides a non-invasive method for isolating or detecting a nucleic acid molecule from an epidermal sample of a psoriatic lesion of a human subject, including applying an adhesive tape to the psoriatic lesion of the subject in a manner sufficient to isolate an epidermal sample adhering to the adhesive tape. The epidermal sample includes a nucleic acid molecule that is then isolated and/or detected.

The nucleic acid for example can encode a protein such as CD2, TNFI. or IFNγ. Expression of these genes can be analyzed in psoriatic lesions. These embodiments, are useful for monitoring response to treatment for psoriasis; for determining a treatment that is likely most effective, for genetically characterizing psoriasis; for diagnosing psoriasis; and for identifying and analyzing nucleic acids that are predictive for response to a treatment for psoriasis. Changes in expression of these genes is shown in the Examples provided herein to be associated with psoriasis. For example, expression of TNFI and CD2 are elevated in most patients with psoriasis. Furthermore, in certain patients TNFI, CD2, and IFNγ are elevated. Accordingly, in certain aspects, expression of TNFI and CD2 is analyzed. In other aspects, expression of TNFI, CD2, and IFNγ are analyzed.

Methods of the present invention which isolate and detect a nucleic acid sample from an epidermal sample of a psoriatic lesion have utility not only in detecting and staging a psoriatic lesion, but also in diagnosing, and prognosing psoriasis as well as monitoring response of a psoriatic lesion to treatment. These methods can also be used to identify a predictive skin marker to identify a lesion and/or a patient, that will respond to treatment for psoriasis.

A biologic is a molecule derived from a living organism. Biologics used to treat psoriasis typically target precise immune responses involved with psoriasis. Published data from studies suggests that pinpointing specific immune responses produces less-toxic side effects because the entire immune system is not affected and neither are organs, such as the liver and kidneys. Some biologics work by either interfering with the abnormal T cells or blocking TNF-α. Typically, biologics must be injected or infused to work.

The biologic can be, for example, alefacept or efalizumab, typically used for the treatment of adults who have moderate to severe chronic plaque psoriasis. Alefacept, which is typically given by intramuscular injection once a week for 12 weeks, targets and kills a select group of T cells that drive psoriasis.

Efalizumab, like alefacept, prevents T cells from becoming activated; and inhibits T cell trafficking. This prevents the T cells from entering the skin and causing inflammation. Efalizumab, which typically involves weekly shots, unlike other systemic medications used to treat psoriasis, provides continuous therapy and is meant for long-term use.

Etanercept™, infliximab™ and adalimumab™ are biologic agents that block TNF-α. In psoriasis, TNF-α is a chemical believed to be used by the immune system that signals the skin to reproduce and mature too quickly (Gribetz, C. et al. "Clearing Psoriasis: A New Era of Optimism." Contemporary Dermatology 2003: Vol. 1, No. 1: 1-8.). In certain illustrative examples, expression of a target gene believed to be involved in psoriasis is detected in a psoriatic lesion using a tape stripping method provided herein. If expression or elevated expression is detected, a treatment can be administered to the subject that blocks a function of the target gene. For example, expression of TNFI can be detected using the methods provided herein, and used to predict response to biologics which target TNFI, such as etanercept™, infliximab™ and adalimumab™. For example, elevated levels of TNFI in an epidermal sample in skin can predict that a biologic that targets TNFI will be at least temporarily effective at treating psoriasis of the subject.

As illustrated herein, at least some psoriatic lesions express increased levels of TNFα. Therefore, methods herein to characterize a psoriatic lesion can be used to confirm that psoriatic lesions are expression TNFα before a subject is treated with a biologic such as Etanercept™, infliximab™ and adalimumab that block TNFα. Furthermore, as illustrated herein, IFNK is not overexpressed in the psoriatic lesions of some patients. Accordingly, in certain methods provided herein are used to characterize a psoriatic lesion for expression of IFNK in order to determine whether the subject is likely to respond to treatment with a biologic that targets abnormal T-cells. It is known that IFNK is expressed in T-cells.

Certain embodiments of the present invention are based in part on the discovery that tape stripping psoriatic lesions can be used to monitor response of a subject to treatment for a skin disorder. For example, tape stripping can be used to monitor the response of one or more psoriatic lesions, to treatment. The tape stripping methods can be used to obtain a skin sample at a time point that is before a clinical change in a psoriatic lesion is observed or before a change in the severity of psoriasis is observable. Therefore, the tape stripping methods can be used to obtain information regarding whether a psoriasis patient is responding to treatment before current methods can detect a response to treatment, or lack thereof.

The type and severity of psoriasis are usually measured visually. For example the severity of psoriasis can be measured using the National Psoriasis Grading Score (NPGS), which uses a variety of observable factors, including redness, type of lesions, and amount of skin are affected by redness. Methods provided herein provide an indication of severity and the type of psoriasis based on expression levels of genes associated with psoriasis. These methods can be used to detect a change in psoriasis severity before these changes are observed visually, such as using the NPGS. In certain aspects, the methods of the present invention are used in combination with a visual method, to determine response to treatment.

In another embodiment, provided herein is a method for characterizing psoriasis in a subject including: analyzing expression of one or more nucleic acid molecules from an epidermal sample of a psoriatic lesion of a subject. For this embodiment, typically the subject is a human subject In certain aspects, at least one of the nucleic acid molecules ana-

TABLE VIII

AAD Consensus Statement on Psoriasis Therapy (Callen, JP et. al. AAD Consensus statement on psoriasis therapies. J Amer Acad Dermatol 2003: 49: 897-899)

|  | Topicals | Phototherapy | Systemic |
|---|---|---|---|
| Plaque Psoriasis | Corticosteroids (many types/strengths) Tazarotene Calcipotriene Anthralin Tar preparations Keratolytic agents (salicylic acid, lactic acid, urea) Lubrication products (Therapies may be combined or used in sequence shown.) | UVB (with or w/o topicals and with or w/o oral retinoids) Photochemotherapy (with or w/o oral retinoids) | Methotrexate Cyclosporin Retinoids (acitretin, tazarotene*) Etanercept* Alefacept Efalizumab Infliximab* (Therapies may be combined or used with topicals.) |
| Pustular |  | Phototherapy | Retinoids: (acitretin, isotretinoin*) Methotrexate Cyclosporine Immunobio-logics (sometimes called "biologics") (Therapies may be combined.) |
| Guttae | Topical therapies | Phototherapy (with or w/o tar) Photochemotherapy | Systemic therapies as needed |
| Erythrodermic |  |  | Cyclosporine Methotrexate Retinoids (with or w/o phototherapy or photochemotherapy (Therapies may be combined.) |

*Not yet approved by the U.S. Food and Drug Administration (FDA) for psoriasis.

lyzed is a nucleic acid whose level of expression can effect choice of treatment, such as TNFI, CD2 and/or IFNK. Furthermore, it is illustrated herein that the tape stripping method can be successfully employed in expression analysis using microarrays. Accordingly, microarray analysis can be used to identify additional genes whose expression level is different in psoriatic lesions of different patients, and whose expression level provides useful information regarding the type of psoriatic lesion, treatment choices, disease progression before clinical signs of change in disease, or the likelihood to respond to a therapy.

In another embodiment, the present invention provides a method for diagnosing psoriasis in a human subject, including: applying an adhesive tape to a lesion suspected of being a psoriatic lesion on the skin of the subject in a manner sufficient to isolate an epidermal sample adhering to the adhesive tape, wherein the epidermal sample includes a target nucleic acid molecule. The target nucleic acid molecule is the detected, wherein an altered expression of the target nucleic acid molecule as compared with expression in an epidermal sample from a sample not having psoriasis is indicative of psoriasis. In certain aspects, two or more target nucleic acid molecules are detected.

In certain aspects, two or more target nucleic acid molecules that encode two or more proteins selected from CD2, TNFI, IFNγ; GAPDH, θ-actin, IL-12B, IL-23A, Krt-16, Krt-17 are detected. In certain aspects, GAPDH and θ-actin are used as controls, for example in $-C_t$ calculations. In certain aspects a biopsy is taken at the site of the skin, and a nucleic acid sample is obtained from the biopsy. For example, in the biopsied sample expression of a target nucleic acid molecule encoding a protein selected from TNFI, CD2, IFNγ, IL-12B, IL-23A, Krt-16, or Krt-17, is detected. Expression of all of these genes is known to be elevated in biopsied samples.

In the methods provided herein, tape stripping can be performed in a clinical setting by a first party that can send the tape strips to a second party for nucleic acid detection. Nucleic acid isolation can be performed by either the first party or the second party. For example, tape stripping can be performed in a physicians office by a nurse who sends the tape strips to a second party, such as an outside company who performs nucleic acid isolation and detection. Alternatively, nucleic acid isolation can be performed in the physicians office, who can send the isolated nucleic acid sample to a second party, such as an outside service provided, to perform nucleic acid detection and expression analysis.

Where two parties are involved in performing methods discussed herein, or where the methods disclosed herein are performed within the same entity, revenue could be generated for performing the methods disclosed herein. For example, revenue can be generated for a service that performs a portion of the methods by accepting revenue in exchange for nucleic acid detection and expression analysis from tape strips. Furthermore, the service could generate an RNA profile and/or a classification of the sample as ACD versus ICD or potentially corrosive. A corrosive substance can cause severe damage to the skin (e.g. sodium hydroxide, 10% acetic acid). Therefore, provided herein is a method of generating revenue by obtaining revenue for isolating and detecting a nucleic acid in an epidermal sample obtained using tape stripping. Furthermore, revenue can be generated by selling kits, disclosed herein, that include adhesive tape for tape stripping skin, such as rubber-based, pliable adhesive tape. The kits could include RNA isolation reagents and optionally primers and probes for genes whose expression is correlated with a skin disease or pathological skin state. Furthermore the kit could include primers and probes for control genes, such as housekeeping genes. The primers and probes for control genes can be used, for example, in $-C_t$ calculations. The kits could also include instructions for performing tape strippings as well as for analyzing gene expression using $-C_t$ calculations.

In another embodiment, provided herein is a method wherein tape stripping is used to tape harvest skin sites in need of classification. Samples could be mailed to a laboratory of a service provider for development of an RNA profile which would indicate a classification (i.e. ACD versus ICD or corrosive potential) with greater than 95% confidence. The RNA profile could be available over an intranet or internet for viewing by a customer of the service provider. In certain embodiments, a database is provided, of RNA profiles generated from epidermal samples.

Skin samples obtained on adhesive films can be frozen before being analyzed using the methods of the present invention. Typically, this is performed by snap-freezing a sample, as illustrated in the Examples herein, using liquid nitrogen or dry ice.

One or more of the nucleic acid molecules in a sample provided herein, such as a as an epidermal sample, can be amplified before or after they are isolated and/or detected. The term "amplified" refers to the process of making multiple copies of the nucleic acid from a single nucleic acid molecule. The amplification of nucleic acid molecules can be carried out in vitro by biochemical processes known to those of skill in the art. The amplification agent can be any compound or system that will function to accomplish the synthesis of primer extension products, including enzymes. It will be recognized that various amplification methodologies can be utilized to increase the copy number of a target nucleic acid in the nucleic acid samples obtained using the methods provided herein, before and after detection. Suitable enzymes for this purpose include, for example, *E. coli* DNA polymerase I, Taq polymerase, Klenow fragment of *E. coli* DNA polymerase I, T4 DNA polymerase, other available DNA polymerases, T4 or T7 RNA polymerase, polymerase muteins, reverse transcriptase, ligase, and other enzymes, including heat-stable enzymes (i.e., those enzymes that perform primer extension after being subjected to temperatures sufficiently elevated to cause denaturation or those using an RNA polymerase promoter to make aRNA from a DNA template, i.e. linearly amplified aRNA).

Suitable enzymes will facilitate incorporation of nucleotides in the proper manner to form the primer extension products that are complementary to each nucleotide strand. Generally, the synthesis will be initiated at the 3'-end of each primer and proceed in the 5'-direction along the template strand, until synthesis terminates, producing molecules of different lengths. There can be amplification agents, however, that initiate synthesis at the 5'-end and proceed in the other direction, using the same process as described above. In any event, the method of the invention is not to be limited to the amplification methods described herein since it will be understood that virtually any amplification method can be used.

One method of in vitro amplification, which can be used according to this invention, is the polymerase chain reaction (PCR) described in U.S. Pat. Nos. 4,683,202 and 4,683,195. It will be understood that optimal conditions for a PCR reaction can be identified using known techniques. In one illustrative example, RNA is amplified using the MessageAmp™ aRNA kit (as disclosed in the Examples herein).

The primers for use in amplifying the polynucleotides of the invention can be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of nucleotide sequence to be amplified. The term "complementary" means that the primers must hybridize with their respective strands under conditions, which allow the agent for polymerization to function. In other words, the primers that are complementary to the flanking sequences hybridize with the flanking sequences and permit amplification of the nucleotide sequence. The 3' terminus of the primer that is extended can have perfect base paired complementarity with the complementary flanking strand, or can hybridize to the flanking sequences under high stringency conditions.

Upon isolation and optional amplification, expression of one or more genes is analyzed. Analyzing expression includes any qualitative or quantitative method for detecting expression of a gene, many of which are known in the art. Non-limiting methods for analyzing polynucleotides and polypeptides are discussed below. The methods of analyzing expression of the present invention can utilize a biochip, or other miniature high-throughput technology, for detecting expression of two or more genes.

The method of the present invention typically involve isolation of RNA, including messenger RNA (mRNA), from a skin sample. The RNA may be single stranded or double stranded. Enzymes and conditions optimal for reverse transcribing the template to DNA well known in the art can be used. Alternatively, the RNA can be amplified to form amplified RNA. The RNA can be subjected to RNAse protection assays. A DNA-RNA hybrid that contains one strand of each can also be used. A mixture of polynucleotides can also be employed, or the polynucleotides produced in a previous amplification reaction, using the same or different primers can be so used. In certain examples, a nucleic acid to be analyzed is amplified after it is isolated. It is not necessary that the sequence to be amplified be present initially in a pure form; it may be a minor fraction of a complex mixture.

In addition, RNAse protection assays can be used if RNA is the polynucleotide to be detected in the method. In this procedure, a labeled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a ribonucleotide capable of hybridizing to RNA in a sample of interest. Those skilled in the art will be able to identify and modify the RNAse protection assay specific to the polynucleotide to be measured, for example, probe specificity can be altered, hybridization temperatures, quantity of nucleic acid etc. Additionally, a number of commercial kits are available, for example, RiboQuant™ Multi-Probe RNAse Protection Assay System (Pharmingen, Inc., San Diego, Calif.).

In another embodiment, a nucleic acid in the sample may be analyzed by a blotting procedure, typically a Northern blot procedure. For blotting procedures polynucleotides are separated on a gel and then probed with a complementary polynucleotide to the sequence of interest. For example, RNA is separated on a gel transferred to nitrocellulose and probed with complementary DNA to one of the genes disclosed herein. The complementary probe may be labeled radioactively, chemically etc.

Detection of a nucleic acid can include size fractionating the nucleic acid. Methods of size fractionating nucleic acids are well known to those of skill in the art, such as by gel electrophoresis, including polyacrylamide gel electrophoresis (PAGE). For example, the gel may be a denaturing 7 M or 8 M urea-polyacrylamide-formamide gel. Size fractionating the nucleic acid may also be accomplished by chromatographic methods known to those of skill in the art.

The detection of nucleic acids can optionally be performed by using radioactively labeled probes. Any radioactive label can be employed which provides an adequate signal. Other labels include ligands, colored dyes, and fluorescent molecules, which can serve as a specific binding pair member for a labeled ligand, and the like. The labeled preparations are used to probe for a nucleic acid by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see *Genetic Engineering*, 1 ed. Robert Williamson, Academic Press (1981), pp. 72-81). The particular hybridization technique is not essential to the invention. Hybridization techniques are well known or easily ascertained by one of ordinary skill in the art. As improvements are made in hybridization techniques, they can readily be applied in the method of the invention.

Probes according to the present invention and used in a method of the present invention selectively hybridize to a target gene. In preferred embodiments, the probes are spotted on a bioarray using methods known in the art. As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in detecting expression of a skin marker. It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule.

Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)). An example of progressively higher stringency conditions is as follows: 2×SSC/ 0.1% SDS at about room temperature (hybridization conditions); 0.2×SSC/0.1% SDS at about room temperature (low stringency conditions); 0.2×SSC/0.1% SDS at about 42EC (moderate stringency conditions); and 0.1×SSC at about 68EC (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

A method for detecting one or more genes can alternatively employ the detection of a polypeptide product of one of these genes. For example, polypeptide products of one of the genes disclosed herein as associated with psoriasis or irritated skin, can be analyzed. The levels of such gene products are indicative of psoriasis or a skin irritation when compared to a normal or standard polypeptide profiles in a similar tissue. Thus, the expression pattern of a gene disclosed herein as associated with psoriasis or irritant dermatitis, will vary depending upon the presence and stage of psoriasis or irritant dermatitis respectively.

In this regard, the sample, as described herein, can be used as a source to isolate polypeptides. For example, following skin stripping, using the methods described above, cells isolated from the stratum corneum can be lysed by any number of means, and polypeptides obtained from the cells. These polypeptides can then be quantified using methods known to those of skill in the art, for example by protein microarrays, or ELISA analysis.

In another embodiment, the present invention provides a method for obtaining gene expression data from amplified nucleic acids that compensates for variability in amplification reactions. In this method, relative expression of a target nucleic acid molecule and a control nucleic acid molecule is compared to obtain relevant expression data. Accordingly, in certain embodiments provided herein, a –Ct value is determined in order to identify gene expression changes. This value and method, although illustrated herein with respect to tape stripped skin samples, can be used to identify differential gene expression in any tissue. It is especially useful, where it is relatively difficult to obtain sufficient RNA from a control sample.

The $C_t$ values is the experimentally determined number of amplification (e.g. PCR) cycles required to achieve a threshold signal level (statistically significant increase in signal level (e.g. fluorescence) over background) for $mRNA_x$ and a control mRNA (Gibson, Heid et al. 1996; Heid, Stevens et al. 1996). The $C_t$ values are typically determined using a target nucleic acid (e.g. $mRNAx$) primer and probe set, and a control mRNA primer and probe set. A $-C_t$ value is calculated by calculating a difference in the number of amplification cycles required to reach a threshold signal level between the target nucleic acid molecule and the control nucleic acid molecule. A difference in the –Ct value at a target area versus another area of a subject's skin, such as a normal area, or an unaffected area, is indicative of a change in gene expression of the target nucleic acid molecule at the target area.

Using this value, altered expression is detected by comparing expression of the target nucleic acid molecule with expression of a control nucleic acid molecule. The Examples provided herein, illustrate that the $\Delta C_t$ value, which is normally used to calculate a $\Delta\Delta C_t$ value (and thus a calibrated fold-change), is itself useful for characterizing the physiologic state of the epidermis without reference to a calibration site. Example 2 provides the formula and related disclosure for calculating a $\Delta C_t$ value. It is illustrated herein, that although the art teaches using a $\Delta\Delta C_t$ value and not a $\Delta C_t$ value for analyzing expression data, a $\Delta C_t$ value is useful for this purpose, and provides the advantage that it is not necessary to obtain a nucleic acid sample from a control site, where it may be difficult to obtain sufficient nucleic acid molecules.

The potential utility of $\Delta C_t$ values is illustrated in Example 2, by the $\Delta C_{t, IL-8}$ for subject 4's SLS-treated skin (tape-harvested sample; Table IV). The $\Delta C_t$ is –1.28, however it cannot be used to calculate a $\Delta\Delta C_t$ value (and therefore a fold-change) because insufficient RNA was recovered from the unaffected and water-occluded control sites. However, comparison of this $\Delta C_t$ value to the remaining subjects' average SLS $\Delta C_{t, IL-8}$ value of –0.89 and average values from tape-harvested water-occluded and uninvolved skin sites (>2.49 for normal or 1.54 for tape) is highly suggestive that the AC, value of –1.28 is in fact indicative of irritated skin. For example, the value of –1.28 implies that, compared to the average value for the 10 subjects, subject 4's SLS-site IL-8/ β-actin mRNA ratio is at least $2^{-(-0.28-2.49)}$ or 13.6-fold higher than the average value for uninvolved skin. A similar calculation using the average $\Delta C_{t, IL-8}$ for water-occluded samples as the calibrator suggests that the IL-8/actin mRNA ratio is $2^{-(-0.28-1.54)}$ or 7.1-fold elevated. These data lead to the hypothesis that establishment of a database of $\Delta C_t$ values for different mRNA biomarkers might be useful to identify a physiologic skin state without reference to an intrasubject control site. This utility of $\Delta C_t$ values is predicated upon the consistency of the PCR reaction conditions and the use of identical probes between samples. Given these prerequisites, data in the Examples herein, support the potential for $\Delta C_t$ values being diagnostic indicators.

Accordingly, provided herein is a method for detecting a change in gene expression, including: applying a first adhesive tape to a target area of skin and a second adhesive tape to an unaffected area of the skin, in a manner sufficient to isolate an epidermal sample adhering to the first adhesive tape and the second adhesive tape, wherein the epidermal samples comprise nucleic acid molecules; and for each of the target area sample and the normal area sample, amplifying a target nucleic acid molecule and a control nucleic acid molecule. For each of the target area sample and the normal area sample, a target nucleic acid molecule and a control nucleic acid molecule are amplified and identifying, and a –Ct value by calculated by calculating a difference in the number of amplification cycles required to reach a threshold signal level between the target nucleic acid molecule and a control nucleic acid molecule, wherein a difference in the –Ct value at the target area versus the normal area is indicative of a change in gene expression of the target nucleic acid molecule at the target area. The Ct values are typically determined in the same amplification experiment (e.g. using separate reaction wells on the same multi-well reaction plate) using similar reaction conditions to other reactions.

The method for detecting a change in gene expression can be used along with the other embodiments provided herein to identify changes in gene expression. For example, the method can be used to diagnose a skin disease or pathological skin state. In certain aspects, the method can be used to detect a change in expression for any of the genes listed in Table VII, to assist in a characterization of a skin area as involving irritant contact dermatitis.

Accordingly to the tape stripping method provided herein, a first population of adhesive tapes can be applied to the target region, and a second population of adhesive tapes can be applied to a normal area of skin or an unaffected area of skin. For example, four separate tape strips can be applied to the target area of the skin and nucleic acids on the tape strips can be amplified together in a first reaction vessel. A different four separate tape strips can be applied to a normal area of the skin and nucleic acids on these tape strips can be amplified together in a second reaction vessel. In the first vessel and the second vessel, both the control nucleic acid and the target nucleic acid can be amplified.

The target area for this embodiment, is typically an area of skin suspected containing diseased skin or skin in a pathological state. For example, the target area can include a psoriatic lesion or a region of skin with the characteristics of dermatitis.

In certain examples, the control nucleic acid molecule is expressed from a housekeeping gene. For example, the control nucleic aid molecule can encode β-actin, GAPDH, 18S rRNA, 28S rRNA, or tubulin. The adhesive tape is typically applied one to ten times, or between one and ten identical adhesive tapes are applied, as discussed herein related to the tape stripping method provided herein. Furthermore, a method according to this embodiment can utilize a microarray to detect a population of target nucleic acid molecules.

In another embodiment, the present invention provides a method for sampling an epidermal layer other than skin, using the tape stripping method provided herein. For example, the tape stripping method can be used to obtain a nucleic acid sample from an epidermal layer of the mouth, throat, or nose, or of an organ such as the liver, pancreas, kidney, intestines, stomach, bladder, brain, heart, or lungs, etc. by introducing a tape strip into a subject and applying it to a surface of the organ. The organ can be sampled within a body of the subject or after the organ is removed from the subject. Furthermore, the tape stripping method can be used to sample cells grown in vitro or organs reconstructed in vitro, for example for organ transplantation.

In another embodiment the invention provides a kit for isolation and detection of a nucleic acid from an epidermal sample, such as an epidermal sample from a psoriatic lesion or a target area of skin suspected of being inflamed. The kit can include an adhesive tape for performing methods provided herein. Accordingly, in one embodiment, provided herein is a kit, including a pliable adhesive tape made up at least in part, of a non-polar polymer. In certain aspects, the tape includes a rubber adhesive. In an illustrative example, the tape can be skin harvesting tape available (Product No. 90068) from Adhesives Research, Inc (Glen Rock, Pa.).

In addition to adhesive tape, the kit typically includes one or more detection reagents, for example probes and/or primers for amplification of, or hybridization to, a target nucleic acid sequence whose expression is related to a skin disease or pathological state. The probes or primers can be labeled with an enzymatic, florescent, or radionuclide label. For example, the probe can bind to a target nucleic acid molecule encoding a protein selected from CD2, TNFI. IFNγ; GAPDH, or Krt-16. Alternatively, the probe can be, for example, an antibody that binds the encoded protein. The probes can be spotted on a microarray which is provided in the kit.

The term "detectably labeled deoxyribonucleotide" refers to a deoxyribonucleotide that is associated with a detectable label for detecting the deoxyribonucleotide. For example, the detectable label may be a radiolabeled nucleotide or a small molecule covalently bound to the nucleotide where the small molecule is recognized by a well-characterized large molecule. Examples of these small molecules are biotin, which is bound by avidin, and thyroxin, which is bound by anti-thyroxin antibody. Other labels are known to those of ordinary skill in the art, including enzymatic, fluorescent compounds, chemiluminescent compounds, phosphorescent compounds, and bioluminescent compounds.

The kit can include one or more primer pairs, including a forward primer that selectively binds upstream of a gene whose expression is associated with psoriasis or irritant dermatitis, for example, on one strand, and a reverse primer, that selectively binds upstream of a gene involved in psoriasis or irritant dermatitis on a complementary strand. Primer pairs according to this aspect of the invention are typically useful for amplifying a polynucleotide that corresponds to a skin marker gene associated with psoriasis or contact dermatitis using amplification methods described herein.

A kit provided herein can also include a carrier means being compartmentalized to receive in close confinement one or more containers such as vials, tubes, and the like, each of the containers comprising one of the separate elements to be used in a method provided herein. If present, a second container may include, for example, a lysis buffer. The kit can alternatively include a computer-type chip on which the lysis of the cell will be achieved by means of an electric current.

Accordingly, kits provided herein can include an adhesive tape for tape stripping skin, such as rubber-based, pliable adhesive tape. The kits could include RNA isolation reagents and optionally primers and probes for genes whose expression is correlated with a skin disease or pathological skin state. Furthermore the kit could include primers and probes for control genes, such as housekeeping genes. The primers and probes for control genes can be used, for example, in $-C_t$ calculations. The kits could also include instructions for performing tape strippings as well as for analyzing gene expression using $-C_t$ calculations.

The present invention is not to be limited in scope by the specific examples provided for below, which are intended as single illustrations of individual aspects of the invention and functionally equivalent methods and components are within the scope of the invention.

EXAMPLE 1

Identification of Superior Tape Characteristics for Isolating Nucleic Acid Acids from Skin Samples The objective of this experiment was to compare adhesive films of differing rigidity for the ability to remove epidermis and associated total RNA from of surface of the skin.

The experimental protocol described here is designed to test the hypothesis that rigid tapes will remove more epidermis (and hence recover more RNA) than an equivalent adhesive on a less rigid support.

TABLE 5

Product codes for adhesive tape test samples.

| Product Code | Description | Property Measured |
|---|---|---|
| 413-201-1 | 3.0 mil clear PET (polyester film)/413-166-A (approx. 2.9 mil/2.0 mil ARMS) Adhesive identical to sample 413-92-1 | Stiff backing |
| 413-92-1 | 3.0 mil PU (polyurethane film)/413-92-A (approx. 2.9 mil/2.0 mil ARMS release liner) | Flexible backing |

Procedure: Two main sites on the upper back with minimal hair were chosen for the tape stripping. Each site was about 40 mm×40 mm in size so as to allow three non-overlapping areas or "sub-sites" within the main site to be tape stripped. The main sites were in a similar anatomical location for all subjects. The main sites were cleansed with an alcohol pad and allowed to air dry 5 minutes. A test tape (obtained from Adhesive Research, Glen Rock, Pa.) was applied with pressure to one sub-site and removed. This procedure was repeated 3 additional times (4 total tape strips), each time with a fresh tape, to the same sub-site. A total of three sub-sites were tape-stripped. On each subject, one main site was tape stripped at the 3 sub-sites with tape 413-201-1; the other main site was tape stripped at the 3 sub-sites with tape 413-92-1. RNA was extracted from the tapes as described in Example 2 using a Qiagen RNeasy™ kit and quantified by quantitative RT-PCR using the standard curve method with total human spleen RNA as the standard.

Results and discussion: Table 6 shows the average mass of RNA recovered per site for each subject. The data in Table 6 clearly shows that the adhesive with the flexible (i.e. pliable) backing (92-1) is superior in the average amount of RNA recovered per site. Tape 92-1 collected on the average 6.1-fold more RNA than did tape 201-1.

TABLE 6

The average mass of total RNA recovered per site per subject using one adhesive formulation on two different backings.

| Subject | Average mass recovered per site[1] | | Mass ratio |
| --- | --- | --- | --- |
| | Tape 201-1 | Tape 92-1 | 92-1/201-1 |
| 1 | 0.86 | 6.09 | 7.09 |
| 2 | 1.23 | 4.48 | 3.64 |
| 3 | 0.37 | 2.95 | 7.97 |
| 4 | 0.50 | 4.64 | 9.31 |
| 5 | 2.02 | 48.30 | 23.85 |
| 6 | 8.52 | 16.00 | 1.88 |
| Average per site across subjects (±SEM) | 2.25 (±1.27) | 13.74 (±7.17) | 6.11 |

[1]The average mass of total RNA in nanograms recovered per sub-site for each tape, in 6 subjects. RNA was quantitated using quantitative RT-PCR by the standard curve method.

From the data in Table 6 it is concluded that the synthetic rubber adhesive on a pliable polyurethane film is superior for the purposes of RNA recovery than the same adhesive on a stiff polyethylene film backing.

Next, a synthetic rubber adhesive formulation was compared to an acrylic adhesive formulation for the ability to retrieve RNA from epidermal cells recovered from the surface of uninvolved skin and water-occluded skin by tape stripping.

TABLE 7

Descriptions of adhesive tape films used in this protocol.

| Adhesive ID | Description |
| --- | --- |
| 413-92-1 | 3.0 mil polyurethane film; 413-92-A (approx. 2.9 mil/2.0 mil ARMS release liner); rubber-based adhesive (Product 90068) |
| 413-92-3 | 3.0 mil polyurethane film; 413-92-C (approx. 2.8 mil/2.0 mil ARMS release liner); acrylic-based adhesive |

Site selection and harvesting procedure: The back was chosen as the site for this protocol. Sites were cleansed with alcohol and allowed to air dry before applying the water soaked patch. The water patches contained 0.25 ml of distilled, sterile water. Patches remained attached for 24-hours.

Subjects returned to the clinic 24-hours later for patch removal. Once the patches were removed, the patched sites were not cleansed, but simply allowed to air dry for 15 minutes; the uninvolved skin site was cleansed with an alcohol patch and allowed to air dry for 5 minutes. After air-drying, and visual grading, 3 water and 3 adjacent uninvolved skin sites were tape-stripped with tape 413-92-1 four times each (4 new tapes per site). The remaining 3 water and 3 uninvolved skin sites were similarly harvested with tape 413-92-3.

Results and discussion: In this experiment two different adhesive formulations were tested for the ability to recover RNA by tape harvesting the surface of the skin.

TABLE 8

Average mass of total RNA recovered per site from normal and water treated skin in 7 subjects.

| | Average RNA Yield by Tape and Skin Treatment | | | |
| --- | --- | --- | --- | --- |
| | Tape 92-1 (rubber) | | Tape 92-3 (acrylic) | |
| Subject | Uninvolved skin[1] | Water Occluded[1] | Uninvolved skin[1] | Water Occluded[1] |
| 1 | 3.6 | 0.77 | 0.076 | 0.16 |
| 2 | 62 | 14.9 | ND | ND |
| 3 | 6.3 | 3.2 | 0.069 | ND |
| 4 | 0.54 | 0.14 | ND | ND |
| 5 | 12.1 | 8.5 | 0.026* | 0.78* |
| 6 | 5.9 | 10 | 0.50* | ND |
| 7 | 1.2 | 2.1 | 1.06 | 1.11 |
| Subject average ± SEM | 13.1 ± 8.3 | 5.7 ± 2.1 | 0.35 ± 0.2 | 0.68 ± 0.28 |

[1]The average mass of total RNA recovered per site is shown in nanograms; unless otherwise noted, each value is the average of 3 sub-sites;
ND indicates that no RNA was detected;
*indicates that the value is an average of less than 3 sites because RNA was not detected at all sites Table 8 clearly reveals that tape 92-1 is superior at recovering RNA from normal and water-occluded skin. In conclusion, a prototype rubber adhesive film (Product 90068) (Adhesive Research, Inc., Glen Rock, Pa.) was tested against an acrylic adhesive for the ability to recover RNA from the surface of the skin. The results conclusively demonstrate that the prototype rubber-based film is better than the acrylic film at recovering RNA from normal and water-occluded skin sites.

EXAMPLE 2

The Use of RT-PCR and DNA Microarrays to Characterize RNA Recovered by Non-Invasive Tape-Harvesting of Normal and Inflamed Skin This example illustrates a non-invasive approach for recovering messenger RNA from the surface of skin via a simple tape stripping procedure that permits a direct quantitative and qualitative assessment of pathologic and physiologic biomarkers. Tape-harvested RNA is shown to be comparable in quality and utility to RNA recovered by biopsy. Using SLS irritation as a model system, the utility of assaying changes in IL-1β and IL-8 mRNA has been tested as an indication of irritant skin reactions and show that both sampling methods allow the recovery of RNA, the analysis of which reveals cutaneous irritation. Data is presented that biopsy and tape-harvested RNA are likely derived from different cell populations and that tape harvesting is an efficient method for sampling the epidermis and identifying select differentially regulated epidermal biomarkers. The successful amplification of tape-harvested RNA is reported, for hybridization to DNA microarrays. These experiments showed no significant gene expression level differences between replicate sites on a subject and minimal differences between a male and female subject. The array generated RNA profiles was also compared between normal and 24-hour 1% SLS-occluded skin and observed that SLS treatment resulted in statistically significant changes in the expression levels of more than 1,700 genes. These data establish the utility of tape harvesting as a non-invasive method for capturing RNA from human skin.

Contact dermatitis, a common skin reaction, involves several signaling pathways. Irritant contact dermatitis (ICD) predominantly involves keratinocyte activation (Freedberg, Tomic-Canic et al. 2001), whereas Langerhans cell presentation of antigen to T-cells in draining lymph nodes and recognition of the offending allergen in skin by memory T-cells control the initiation and expression of allergic contact dermatitis (ACD; (Feghali and Wright 1997)) Clinically, both contact dermatitides are characterized by pruritus, erythema and edema. This commonality of the clinical signs and symptoms makes distinguishing between ICD and ACD difficult at the clinical level, particularly when symptoms are subtle. By contrast, at the molecular level, ICD and ACD are believed to be characterized by unique mRNA patterns, although the published literature is conflicting (Hoefakker, Caubo et al. 1995; Flier, Boorsma et al. 1999; Morhenn, Chang et al. 1999; Ryan and Gerberick 1999; Ulfgren, Klareskog et al. 2000; Cumberbatch, Dearman et al. 2002). Documentation of simple and complex mRNA profiles is possible using reverse transcriptase polymerase chain reaction (RT-PCR) and DNA microarray technologies. Using the technique of tape stripping, RNA can be harvested from both normal and inflamed skin and by combining tape stripping and RNA profiling, it may be possible to non-invasively establish a diagnosis of ICD or ACD.

The study disclosed in this Example demonstrates that sufficient RNA can be recovered using sequential application of as few as 4 small tapes to a skin site. In order to document the use of tape harvesting as an accurate and reliable sampling method we performed a clinical trial in which occlusive patches containing either 1% SLS (irritant) or water (vehicle control) were applied to the mid-back of ten subjects for 24 hours. The sites were then clinically assessed and, along with normal control skin, surface cells were harvested with four applications of individual tapes and by shave biopsy. RNA was extracted from the tapes and biopsies and assayed semi-quantitatively for Il-1β, IL-8, GAPDH and β-actin mRNA using fluorescent, quantitative RT-PCR. The results showed consistent increases in IL-1β and IL-8 mRNA in inflamed skin relative to untreated skin. Furthermore, experiments disclosed in this Example illustrate the successful use of tape-harvested RNA to profile normal and experimentally inflamed skin using DNA microarrays. This profile of SLS-irritated skin is an important step in the definition of RNA profiles designed to differentiate irritant from allergic skin reactions.

Materials and Methods

Clinical protocols: The study protocols were reviewed and approved by an independent IRB (BioMed IRB, San Diego) and all subjects signed informed consent. Ten healthy women, ages 21-55 were enrolled in the study. Regions of unblemished, normal appearing skin on the mid back were chosen for the application of 2 occlusive patches in the form of bandages approximately 4 cm×6.5 cm. The bandages were made using a clear, non-porous plastic hypoallergenic adhesive tape. In the center of this tape was a Webril (non-woven cotton) patch measuring approximately 2 cm×4.5 cm. One Webril patch contained 0.6 ml of 1% aqueous sodium lauryl sulfate and the other contained 0.6 ml of sterile water as the vehicle control. Patches were arranged such that the SLS patch was superior and directly adjacent to the water patch; the area of normal control skin was inferior to and adjacent to the water patch. At 24 hours post application, the SLS and water patches were removed and the skin allowed to air dry for 15 minutes before scoring. The sites were scored by a trained technician using the scale provided below. Patched sites were large enough that two areas could be tape harvested without overlap and room left for a shave biopsy (~2×2 mm). Skin sites were tape stripped with 4 tapes each and then a shave biopsy taken under local anesthetic (lidocaine HCl 1% and epinephrine 1:100,000; Abbott Laboratories). The tapes were applied to the skin using 20 seconds of firm pressure with a circular motion The tape used for tape stripping was a synthetic rubber-based adhesive on a polyurethane film (Product No. 90068, Adhesive Research, Glen Rock, Pa.). An area of uninvolved skin was tape harvested and shave biopsied in an identical manner. Tapes were stored in individual eppendorf tubes at −80 until extraction; biopsy samples were placed in buffer RLT and stored at −80 until extraction. Skin responses to each patch application were examined and graded under light supplied by a 100-watt incandescent blue bulb. The following grading scale was used: 0, no visible reaction; 1, slight, pink, patchy erythema; 2, mild confluent, pink erythema; 3, moderate erythema (definite redness) with edema; 4, strong erythema (very intense redness) with edema. In a second study, 3 subjects had 3 patches containing 1% SLS and 3 water patches applied to the mid back for 24 hours: Patches were removed, scored and tape stripped as above. In a third study, two individuals were tape stripped on uninvolved skin on the upper back at three adjacent sites as above. RNA harvested in these last two studies was used in the DNA microarray experiments described below.

Materials and reagents: Adhesive tape was purchased from Adhesives Research, Inc. (Product No. 90068) (Glen Rock, Pa.) in bulk rolls. These rolls were custom fabricated into small circular discs, 17 millimeters in diameter, by Diagnostic Laminations Engineering (Oceanside, Calif.). Total spleen RNA was purchased from Ambion. "RNeasy" RNA extraction kit and Sensiscript Reverse Transcriptase kit were purchased from Qiagen (Valencia, Calif.). PCR primers and probes (TaqMan™ Pre-Developed Assay Reagents) and Taq-Man Universal Master Mix, which included all buffers and enzymes necessary for the amplification and fluorescent detection of specific cDNAs, were purchased from Applied Biosystems (Foster City, Calif.). Total mRNA was amplified using the MessageAmp aRNA kit purchased from Ambion Inc. (Austin, Tex.). Human Genome U133A DNA chips were purchased from Affymetrix Inc. (Santa Clara, Calif.).

Isolation of RNA: The RNA within skin cells adherent to the 4 tapes used to harvest a site was pooled by simultaneously extracting the tapes in a volume of buffer RLT (supplied with RNeasy kit). Extraction was performed using the manufacturer's directions and included a Proteinase K digestion, sonication of tapes and "on-column" DNase I digestion. RNA was eluted in 100 microliters of sterile, RNase free water. Extraction of biopsies was performed with the same kit according to the manufacturer's instructions.

Quantitative RT-PCR: 10 µl of RNA was reverse transcribed (RT) into cDNA with the Sensiscript Reverse Transcriptase kit and random hexamers in a final volume of 2011 according to the manufacturer's directions. The reaction was diluted 5-fold with sterile, nuclease-free water (Ambion) for use in the subsequent amplification/detection reaction. For each specific mRNA detection, 3 replicate RT+ reactions and one RT− (no reverse transcriptase; negative control) reaction were performed. Two amplification/detection reactions were done on each RT+ reaction to yield a total of 6 independent determinations of the threshold value ($C_t$; discussed below). All RT-reactions were amplified using 2 replicates and were negative (data not shown).

Quantitation of RNA mass recovered with adhesive tape and biopsy: The amount of RNA recovered by tape is too small (in most samples) to detect by UV. We have also found that contaminants in the adhesive co-purify with the RNA and interfere with UV and fluorometric detection. We therefore estimated the RNA mass recovered from tapes by using quantitative RT-PCR with reference to a standard curve ($C_{t, actin}$ vs. log [RNA]; (Applied Biosystems 2001)) created from commercially purchased human spleen total RNA. Spleen RNA was treated with DNase I and purified with the Qiagen RNeasy kit following the manufacturer's instructions. Purified standard RNA was quantified spectroscopically using O.D. 260. The standard curve was constructed using 4 concentrations of RNA from 0.01 to 1 μgm/ml. Each RNA standard was reverse transcribed in triplicate and each RT reaction amplified once to yield 3 replicates per standard concentration. Amplification and detection of unknowns was accomplished as described below using β-actin mRNA as the quantified marker. Experimental samples were reverse transcribed in triplicate and each RT reaction amplified in duplicate to yield a total of 6 replicates. The average of these 6 replicates was used to calculate the concentration of RNA in the unknown with reference to the standard curve. Total RNA yields for all samples are reported in Table I. The accuracy of this method relies on the relative amount of β-actin mRNA to total RNA in the epidermis being similar to that in human spleen. If the relative amount of β-actin mRNA to total RNA is different between the two tissues then our mass data will be similarly affected. Therefore, we describe all tape-harvested RNA mass calculations as estimates to reflect this uncertainty. RNA recovered from biopsies was quantified fluorometrically with the RiboGreen RNA Quantitation Reagent (Molecular Probes, Eugene, Oreg.).

Amplification and detection of specific mRNA: Specific mRNAs were converted to cDNA as described above. Specific cDNAs were semi-quantified using gene specific primer/probes (5'-nuclease assay) and fluorescence detection. Amplification and detection assays were performed using TaqMan Pre-Developed Assay Reagents (PDAR; Applied Biosystems) on an Applied Biosystems 7000 Sequence Detection System. β-actin, IL-1β and IL-8 mRNA assays were performed in the same tube (multiplex assay); these multiplex results were confirmed in repeat assays in single tube format (separate tube determination of β-actin and the mRNA of interest; data not shown) using 6 replicates; GAPDH mRNA assays were done in singleplex format. Thermal cycling conditions were: prior to cycling, two minutes at 50° C., then ten minutes at 95° C.; then 40 cycles at 95° C. for 15 seconds and 60° C. for 60 seconds. Threshold detection was set at 0.2 for all assays.

Semi-quantitation of mRNA using the $\Delta\Delta C_t$ method: In this Example the comparative or $\Delta\Delta C_t$ method of calculating relative gene expression levels between two samples, was used. In the $\Delta\Delta C_t$ method the levels of IL-1β, IL-8 and GAPDH mRNAs are assayed semi-quantitatively by normalization to β-actin mRNA to create a ratio of $(mRNA_x)/(\beta$-actin) mRNA for each RNA sample. This ratio is then further normalized to a control sample (a process called "calibration"; (Applied Biosystems 2001)). When comparing the ratio of $mRNA_x$ to β-actin mRNA between two different samples, it is implicitly assumed that the level of β-actin mRNA to total RNA is constant between the two samples (i.e. it is an unchanging housekeeping gene). In the comparative method, the relative fold-increase of the mRNA of interest ("$mRNA_x$") between 2 samples is given by the equation:

$$(mRNA_x/mRNA_{actin})_{Exp} / (mRNA_x/mRNA_{actin})_{Cal} = 2^{-\Delta\Delta C_t}$$

where "Exp" indicates the experimental sample (in this case SLS or water samples); "Cal" indicates the calibrator sample (uninvolved skin); and $\Delta\Delta C_{t,x} = [\Delta C_{t, Exp} - \Delta C_{t, Cal}]_x$; where $\Delta C_{t, Exp}$ and $\Delta C_{t, Cal}$ are calculated as (mean $C_{t, RNAx}$)−(mean $C_{t, actin}$) for the respective samples. The $C_t$ values are the experimentally determined number of PCR cycles required to achieve a threshold fluorescence (statistically significant increase in fluorescence over background) for $mRNA_x$ and β-actin mRNA (Gibson, Heid et al. 1996; Heid, Stevens et al. 1996).

Calculation of fold-increase and data analysis: Key to the method used to measure mRNA is the fact that the quantity of specific mRNA directly correlates with the number of cycles needed to reach threshold fluorescence, thus the fewer the number of cycles (the lower the $C_t$), the more mRNA is initially present. As described above, experimental data is reported as the number of cycles ($C_t$) required to reach a threshold fluorescence. Each reported $C_t$ is the mean of 6 replicate measurements. Calibrated fold-change calculations are made using the equations above. A $mRNA_x/\beta$-actin mRNA ratio was considered to have a significant (with >95% confidence interval) fold-increase relative to its calibrator if the range of fold-change given by $2^{-(\Delta\Delta Ct \pm 2\ SEM)}$ did not include the value of 1, which is the defined value of the calibrator because the $\Delta\Delta C_t$ for the calibrator is equal to 0. The significance of $\Delta C_t$ values (Tables I and IV) was determined by applying a two-sided, paired t-test.

It is our experience that the practical limit of detection for real time PCR is 37 cycles. When the threshold number of PCR cycles ($C_t$) extends beyond 37, these values become highly variable or fluorescence does not achieve a threshold value. To interpret combinations of replicate measurements of undetectable and >37 we applied the rule that if 3 or more of the 6 replicates have any combination of $C_t$ values equal to or greater than 37 (edge of detection) or are undetectable (no $C_t$ value recorded), that mRNA is defined as undetectable and assigned a $C_t$=37. This assignment of a threshold equal to 37 typically occurs when total RNA is low or when a message is not present (for instance IL-1β and IL-8 mRNA in uninvolved skin). The assignment of $C_t$=37 to mRNAs that are undetectable is useful because it allows a calculation of the minimum fold-change of a $mRNA_x$/actin mRNA ratio between two samples.

T7 linear RNA amplification: mRNA was amplified and biotin labeled using a MessageAmp™ aRNA kit purchased from Ambion Inc. according to the manufacturer's instructions. Typical yields of aRNA obtained from two rounds of amplification ranged from 30-80 μg.

Hybridization of biotinylated mRNA targets to Affymetrix GeneChips, staining, data acquisition and data analysis: Hybridization and staining were performed according to the manufacturer's instructions. Data Acquisition: Gene expression values from Affymetrix GeneChips are based on the average difference (AD) between hybridization signals of perfect match (PM) and mismatch (MM) oligonucleotide probe sets for each gene as described in the expression analysis technical manual from Affymetrix. The AD value of each probe set is calculated as AD=Σ(PM−MM)/# probe pairs. In initial iterations, Affymetrix software removed probe pairs that were out of a given range when calculating AD values for each probe set. In this process, the mean and standard deviation were calculated for intensity differences (PM-MM) across the entire probe set (excluding the highest and lowest values), and values within a set number of standard deviations (3 as default) were not included in the calculation. The advantage was that this process minimized the variance introduced by experimental or biological error by removing the outliers present in each probe set. The disadvantage was that this process didn't always remove the same probe pairs for the calculation of the AD values among GeneChips. This led to the misinterpretation of the gene expression profiles obtained from GeneChip experiments. To alleviate this problem, a model-based method incorporated into a program called dChip was developed by Li & Wong (Li and Wong 2001). This method maintains constant probe pair set identities across all GeneChips while excluding outliers due to cross hybridization, contamination during hybridization, or manufacturing defects that affect probe set measurements. For all of the GeneChip experiments reported here, each probe pair set from the *.cel files were modeled by the dChip software prior to statistical analysis. The dChip-modeled expression measurement of each gene was normalized to the total signal of each chip. For any given measurement, a value greater than zero (indicating an expression level) or a zero (indicating an expression level lower than background) was obtained. Only those genes exhibiting an expression level greater than zero in all experiments were used for statistical analysis. Data Analysis: Many experimental designs and applications of gene expression profiling experiments are possible. However, no matter what the purpose of an experiment, each experiment must be replicated a sufficient number of times for statistical analysis of the data. This is basically because each gene expression profiling experiment results in the measurement of the expression levels of thousands of genes. In such a high dimension experiment, the chance for erroneous measurements for any individual gene expression level is high. Thus, in the absence of high replication many genes will show large changes in expression levels between two experimental conditions purely by chance alone, even when the experimental conditions are the same. A simple t-test evaluates the distance between the means of two groups normalized in terms of the within-group standard deviations. The result is that large differences between genotypes for any given gene will be declared non-significant if the expression level of that gene is unreplicable within experimental treatments. Conversely, small differences in expression will be determined to be statistically significant for a given gene if expression levels for that gene are replicable within treatments. In short, the t-test statistic is constructed by scaling the difference in gene expression levels between genotypes relative to the observed variances within genotypes. p-values based on the t-test statistic range from 1.0 for gene expression levels with identical values associated with the null hypothesis to very small p-values for differential gene expression levels that are highly significant. It must be noted, however, that the simple t-test does not perform well with a small number of replicates. With a limited number of replicate measurements, often in the range of two to five for DNA microarray experiments, poor estimates of means, standard deviations, and p-values are obtained.

We have shown that the confidence in the interpretation of DNA microarray data with a low number of replicates can be improved by using a Bayesian statistical approach that incorporates information of within treatment measurements (Baldi and Long 2001; Long, Mangalam et al. 2001). This results in a more consistent set of differentially expressed genes identified with fewer replicates. The Bayesian approach is based on the observation that genes of similar expression levels exhibit similar variance (Hatfield, Hung et al. 2003). Thus, more robust estimates of the variance of a gene can be derived by pooling neighboring genes with comparable expression levels. For the analysis of the data reported here we ranked the mean gene expression levels of each replicate experiment in ascending order, used a sliding window of 101 genes, and assigned the average standard deviation of the 50 genes ranked below and above each gene as the background standard deviation for that gene. The variance of any gene within any given treatment was estimated by the weighted average of the treatment-specific background variance and the treatment-specific empirical variance across experimental replicates. In the Bayesian approach employed in this study, the weight given to the within experiment gene variance estimate is a function of the number of experimental replicates. This leads to the desirable property that the Bayesian approach employing such a regularized t-test converges on the same set of differentially expressed genes as the simple t-test but with fewer replicates (Long, Mangalam et al. 2001).

While the Bayesian method provides more robust p-values, it must be kept in mind that these p-values represent the local confidence that can be placed in an individual gene measurement. They say nothing about the global probability that an individual gene is differentially expressed. This can only be evaluated if an estimate of the global false positive level of each experiment can be determined. In other words, to interpret the results of a high dimensional DNA array experiment it is necessary to determine the global false positive and negative levels inherent in the data set being analyzed. For this purpose we have implemented a mixture-model based method described by Allison et al. (Allison, Gadbury et al. 2002) for the computation of the global false positive and negative levels inherent in a DNA microarray experiment. The basic idea is to consider the p-values based on the regularized t-test described above as a new data set, and to build a probabilistic model for these new data. When control data sets are compared to one another (i.e. no differential gene expression) it is easy to see that the p-values will exhibit a uniform distribution between zero and one. In contrast, when data sets from different genotypes or treatment conditions are compared to one another (differential gene expression), a non-uniform distribution will be observed in which p-values will tend to cluster more closely to zero than one; that is, there will be a subset of differentially expressed genes with "significant" p-values. The computational method of Allison (Allison, Gadbury et al. 2002) is used to model this mixture of uniform and non-uniform distributions to determine the probability, PPDE(p) ranging from 0 to 1, that any gene at any given p-value is differentially expressed; that is, that it is a member of the uniform (not differentially expressed) or the non-uniform (differentially expressed) distribution. With this method, we can estimate the rates of false positives and false negatives as well as true positives and true negatives at any given p-value threshold, PPDE(<p). In other words, we can obtain a posterior probability of differential expression PPDE (p) value for each gene measurement and a PPDE(<p) value at any given p-value threshold based on the experiment-wide global false positive level and the p-value exhibited by that gene. It should also be emphasized that this information allows us to infer the genome-wide number of genes that are differentially expressed; that is, the fraction of genes in the non-uniform distribution (differentially expressed) and the fraction of genes in the uniform distribution (not differentially expressed).

Commonly used software packages for microarray data analysis do not possess algorithms for implementing Bayesian statistical methods. However, our statistical program, Cyber-T (www.igb.uci.edu) does accommodate this approach as well as the PPDE analysis described above. For the experiments reported here, we used these statistical tools incorporated into Cyber-T.

Results

Total RNA Yields

RNA was recovered from 27 of 30 skin sites using 4 tapes as described above. The amount of total RNA recovered was variable from site to site and subject to subject (data not shown). The average mass of RNA recovered from uninvolved skin sites was 0.92 nanograms (±0.35) with a range of 0 (2 samples) to 3.2 ng. The average mass of RNA recovered from water-occluded skin was 0.69 ng (±0.27) with a range of 0 (1 sample) to 2.7 ng. SLS inflamed skin produced the greatest average yield of RNA with an average of 185 ng (±76) and a range of 0.067 to 747 ng.

Relative Levels of Housekeeping Genes in Tape Strip Samples and Biopsies

Markers of the inflammatory process IL-1β and IL-8 mRNAs were chosen. Differential recovery of total RNA mass in a sample was accounted for by normalizing these mRNAs to an internal control, the β-actin transcript. We then calibrated the mRNA$_x$/actin ratio in SLS and water samples to that ratio in untreated skin samples. In this study, IL-1β and IL-8 mRNA are predicted to increase relative to β-actin in response to SLS treatment, while the level of housekeeping mRNAs, such as β-actin and GAPDH are predicted to remain constant. We have tested this assumption by measuring the relative ratio of two housekeeping mRNAs, GAPDH and β-actin, to determine if their ratio is indeed a constant in different skin samples.

The measure of the relative abundance of two mRNAs in a sample is given by the $\Delta C_t$ value, which is the difference between the experimentally determined threshold values. To investigate the possibility that $\Delta C_{t,\ GAPDH}$ ($C_{t,\ GAPDH}$–$C_{t,\ actin}$) may have unique values for differently treated skin samples, we determined these values for all samples. Data in Table I show that biopsy-harvested RNA samples from water and SLS-treated sites have significantly different $\Delta C_{t,\ GAPDH}$ values (2-sided, paired t-test; p<0.005) than biopsy-harvested uninvolved skin.

The data in Table I also demonstrate that tape-harvested RNA samples from SLS-treated sites have significantly different $\Delta C_{t,\ GAPDH}$ values than tape-harvested samples from water treated sites (p<0.005). A comparison of tape-harvested samples from SLS treated and uninvolved skin sites nears significance (p=0.087). Tape-harvested RNA samples from water-occluded sites do not have significantly different $\Delta C_{t,\ GAPDH}$ values than uninvolved skin (p=0.61).

Table I further compares the $\Delta C_{t,\ GAPDH}$ values between tape and biopsy harvested samples of identically treated skin sites. The data show that each sampling method produces an RNA sample with a different $\Delta C_{t,\ GAPDH}$, and that this difference is highly significant (p<0.005) for SLS-treated skin samples and uninvolved skin samples (p=0.014). Because biopsy and tape-harvested RNA samples have differing $\Delta C_{t,\ GAPDH}$ values (and therefore different GAPDH/β-actin mRNA ratios), we hypothesize that the sampling methods are recovering different cell populations.

The data in Table I can be used to calculate the fold-change in GAPDH/actin mRNA ratios relative to uninvolved skin (see Materials and Methods). The results of such calculations, shown in Table II, reveal that while there is some variation in the GAPDH/actin mRNA ratios for different samples, the average variation amongst subjects for a particular treatment is less than 2-fold. While some individual changes are greater than 2-fold, these differences are insufficient to explain the much larger fold-changes we observe for IL-1β and IL-8/actin mRNA ratios. Thus, while there are statistically significant changes in GAPDH/actin mRNA ratios due to water and SLS treatment of the skin, these differences do not explain the changes in IL-1β and IL-8/actin ratios discussed later.

IL-1β/β-Actin mRNA Ratios in SLS-Irritated and Control Skin

Table III reveals the fold change of IL-1β/β-actin mRNA in water-occluded and SLS-occluded skin relative to (calibrated to) uninvolved skin, in tape and biopsy harvested RNA samples. In 9 of 10 biopsy samples of SLS-occluded skin, the IL-1β/β-actin mRNA ratio was significantly elevated. In 7 of 10 uninvolved skin biopsy samples, IL-1β mRNA was undetectable, while in the remaining 3 samples it was present at very low levels (within 3 $C_t$ units of our detection limit; data not shown). In biopsy samples of water-occluded skin, IL-1 mRNA was not detectable in 2 samples and was significantly elevated in 3 samples (Table III). Thus SLS-occlusion produced the most consistent elevation of the IL-1β/actin mRNA ratio but water-occlusion could effect a similar albeit smaller response. When the effect of water-occlusion is taken into effect by calibration of the SLS sample to the water-treated site, we find that 7 SLS-treated samples have significant increases in the IL-1β/actin mRNA ratio (data from Table III; calculation not shown).

Data in Table III reveal the fold change of IL-1β/β-actin mRNA in tape-harvested samples of water-occluded and SLS-occluded skin relative to uninvolved skin. Tape-harvested samples of SLS-occluded sites showed significant increases in 5 of 10 samples. These 5 samples with IL-1β increases are in qualitative agreement with the biopsy data. Analysis of the remaining 5 samples was indeterminate due to low RNA recovery. Similar to biopsy samples, tape samples of uninvolved skin did not have detectable amounts of IL-1β with one exception. Tape-harvested samples of water-occluded skin also showed undetectable amounts of IL-1β mRNA in 9 of 10 samples, while one sample with detectable IL-1 displayed a significant increase in IL-1β/actin mRNA relative to uninvolved skin.

IL-8/β-Actin mRNA Ratios in SLS-Irritated and Control Skin

Table III reveals the fold increase of the IL-8/β-actin mRNA ratio in water-occluded and SLS-occluded skin compared to uninvolved skin. The data demonstrate that 8 of 10 biopsy samples of SLS-occluded skin revealed significant increases in IL-8/actin mRNA ratios. Biopsy samples from 9 of 10 untreated skin sites had undetectable IL-8 mRNA levels. The one uninvolved skin biopsy sample with detectable IL-8 mRNA was close to the level of detection. Thus IL-8 mRNA was generally not detectable in a biopsy of uninvolved skin. Similarly 5 of 10 samples from biopsies of water-occluded sites also had undetectable IL-8 mRNA. In the remaining 5 water-treated samples, 2 had significantly increased IL-8/actin mRNA ratios although these increases were small in comparison to the respective SLS-occluded sites. Thus water-occlusion did not appreciably stimulate IL-8 mRNA appearance in the epidermis of most subjects.

Table III further reveals that 8 of 10 tape-harvested samples from SLS-occluded sites displayed significantly increased IL-8/β-actin mRNA ratios. Of the 2 samples without significant increases, one did not have detectable IL-8 mRNA (the sample was low in RNA and the result is inconclusive) while the second sample (Subject 4) likely had increased IL-8 message (see Discussion) but this could not be confirmed because the control tape sample failed to recover RNA. Data in Table III show that tape-harvested samples of water-treated sites reveal significant increases in IL-8/actin mRNA ratios in 3 subjects. In the remaining subjects, IL-8 could not be detected at significantly elevated levels. Thus, the tape data is in good qualitative agreement with the biopsy data with a majority of inflamed sites revealing increases in IL-8 mRNA.

Table IV reveals $\Delta C_{t,\ IL-8}$ values for all samples. This data supports and extends the previous observation that biopsy and tape harvested samples of equivalently treated sites may produce significantly different $\Delta C_t$ values. Table IV reveals that the average $\Delta C_{t,\ IL-8}$ value from tape-harvested, SLS-treated sites was −0.89 while the average value from biopsy harvested SLS sites was 4.13. A paired t-test between the individual $\Delta C_t$ values has a p<0.005. A similar comparison of $\Delta_{C,\ IL\text{-}8}$ values between biopsy and tape harvested RNA samples from the water-occluded sites also shows a highly significant difference (p<0.005). These observations extend to uninvolved skin as well. Table IV shows that 4 samples of tape-harvested uninvolved skin had $\Delta C_{t,\ IL\text{-}8}$ values with a range of 1.51 to 4.15 while the analogous biopsy samples had a range of 8.22 to >9.7, a clear difference. The ability to consistently detect higher amounts of IL-8 mRNA in normal, water and SLS treated skin samples recovered by tape reinforces the hypothesis that tape harvesting preferentially recovers a subset of cells (probably close to the surface) poorly represented in biopsies.

DNA Microarray Analysis of RNA Extracted from Uninvolved Skin Using Tape

The success in the above analysis of tape-harvested RNA from different skin sites suggested that this RNA might be amenable to amplification and hybridization to DNA microarrays. In order to assess the reproducibility and consistency of tape-harvested RNA samples for gene expression profiling experiments, three samples were collected from the upper back of each of two healthy individuals, one male (sample C1, C2, and C3) and one female (sample A5, A6, and A9). Approximately one nanogram of total RNA was isolated and the mRNA was amplified and biotin labeled using a MessageAmp aRNA kit as described in Materials and Methods. The resulting biotin-labeled aRNA from each sample was used for hybridization to an Affymetrix HG-U133A GeneChip.

The results in TABLE V show the differences observed when a matrix of pair-wise gene expression comparisons between two GeneChips was performed using Affymetrix Microarray Suite software. These data show an average of only 12% variance among gene measurements, regardless of whether data from different sites on the same individual or sites from different individuals are compared. Furthermore, comparing the data in quadrant three of TABLE V (A vs. C) to the data in quadrants one (A vs. A) and four (C vs. C) shows that about 15% of this variance is due to either gender difference (A vs. C) or inter-subject variation (A vs. A or C vs. C). Thus, amazingly little variance is contributed by samples obtained from different sites or from different individuals.

To compare these data in a more quantitative manner, the three Affymetrix GeneChips each hybridized with targets from RNA samples obtained from individual A were compared to three GeneChips hybridized with targets from the three RNA samples obtained from individual C. These data were analyzed with a regularized t-test implemented in the Cyber-T statistical program. This three-by-three comparison revealed 21,790 probe sets that exhibited gene expression levels above background for all three sites from each subject. Of these genes 1,117 (5%) were differentially expressed with p-value less than 0.0035, which based on the global false positive and negative levels of this data set corresponds to a posterior probability of differential expression (PPDE) value of 0.95. Thus, 56 of the 1,117 differentially expressed genes that exceed this p-value threshold are expected to be false positives. The source of these inter-subject gene expression differences remains to be determined, however at least one of these differences is gender based. For example, the gene with the smallest p-value and the highest PPDE value is the Y-linked ribosomal protein S4 (PRS4Y). It is likely that differences that are not gender based are a reflection of normal variation of gene expression between individuals. These data are available at www.igb.uci.edu.

DNA Microarray Analysis of Normal Versus Water-Occluded and SLS-Occluded Skin.

In a separate experiment, a total of nine RNA samples ranging from 1-10 nanograms were isolated by tape harvesting from three untreated, three water-occluded, and three SLS-occluded sites of each of three individuals. mRNA from each of the nine samples was amplified, biotin labeled and used for hybridization to each of nine Affymetrix HG-U133A GeneChips as shown in FIG. 1.

Figure 2:
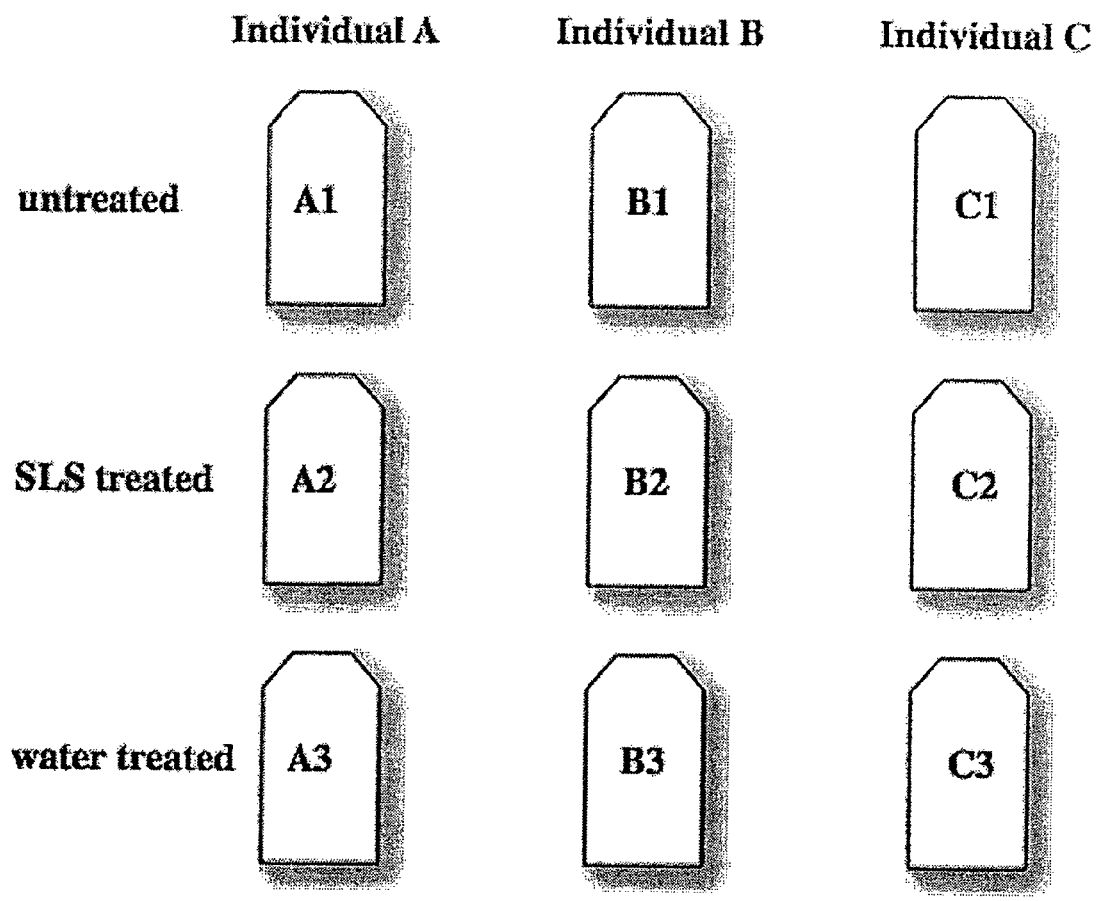
FIGS. 2A to 2C provide p-value distributions for gene expression changes upon induction of irritation by SLS exposure. The p-values, based on a regularized t-test distribution of all genes expressed at value above background in all replicate experiments grouped into 100 bins and plotted against the number of genes in each bin. Panel A, the 21,031 p-values of genes compared between untreated versus SLS occluded samples. Panel B, the 21,307 p-values of genes compared between SLS treated versus water occluded samples. Panel C, 21,164 p-values of genes compared between untreated versus water occluded samples. The dashed lines in Panels A and B indicate the uniform distribution of p-values under conditions of no differential expression.

Untreated vs. SLS treated samples. A comparison of gene expression levels between three untreated (A1, B1, C1) samples and three SLS treated (A2, B2, C2) samples revealed 21,031 genes that exhibited expression levels above background for all samples. To assess the confidence in global changes in gene expression, the p-values for all gene measurements were distributed into 100 bins ranging from 0 to 1.0 and plotted against the number of genes in each bin (FIG. 2A). The β-mixture modeling methods implemented in Cyber-T were used to model these p-value distributions of the uniform (not differentially expressed) and non-uniform (differentially expressed) data sets to determine the posterior probability of differential expression, PPDE, of each gene based on global false positive and negative gene measurement levels as described by Hung et al. (Hung, Baldi et al. 2002) and Baldi and Hatfield (Baldi and Hatfield 2002). When untreated vs. SLS occluded (FIG. 2A) data are compared, the p-values for the differentially expressed genes are low and cluster toward 0. This is consistent with highly statistically significant differences among measurement levels of some genes. In fact 1,771 genes that are differentially expressed with a threshold of p=0.003, which corresponds to a PPDE(p) value equal to or greater than 0.99. These data are available in Table VII provided on the compact disk filed herewith as file 6392999.xls.

SLS vs. water treated samples. A comparison of gene expression levels between three SLS treated (A2, B2, C2) samples and three water treated (A3, B3, C3) samples revealed 21,307 genes that exhibited expression levels above background for all samples. The p-values for all of these gene measurements were also distributed into 100 bins ranging from 0 to 1.0 and plotted against the number of genes in each bin (FIG. 2B). It is evident from an examination of the p-value distribution that, similar to the comparison with untreated cells, about twenty percent of the genes are differentially expressed. Based on a threshold of p=0.003, 1,364 genes are differentially expressed with a PPDE(p) value of 0.99. Of these, 1,063 genes are also differentially expressed with a p-value of 0.003 and a PPDE value of 0.99 when SLS and untreated samples are compared. These data are available at www.igb.uci.edu.

Untreated vs. water treated samples. A comparison of gene expression levels between three untreated (A1, B1, C1) samples and three water treated (A3, B3, C3) samples revealed 21,164 genes that exhibited expression levels above background for all samples. The p-values for all these gene measurements were again distributed into 100 bins ranging from 0 to 1.0 and plotted against the number of genes in each bin (FIG. 2C). The fact that these p-values are uniformly distributed demonstrates that, at the levels of variance inherent in these experiments, there are no statistically significant differences between the gene expression levels of these two data sets. Nevertheless, based on a review of the genes assigned the lowest p-values, many of which are associated with inflammation, we believe that the water treatment does lead to some changes in gene expression compared to untreated control skin. These data are found in Tables VII (provided in the attached Appendix) and VIII (See attached Compact Disk).

For purposes of discussion, only the 100 genes differentially expressed with p-values less than $1.4 \times 10^{-10}$ and PPDE (p) values greater than 0.99 are discussed here and in TABLE VI. An examination of these top 100 genes most significantly altered when the SLS treated skin samples were compared to untreated skin samples revealed that, as expected, most of these genes carry out functions related to tissue inflammation and injury (TABLE VI). These differentially expressed genes are proteinases, protease inhibitors, cytokines, chemokines, complement components, HLA factors, or receptors involved in immune regulation. These associations with inflammation and injury responses for many of these mostly up-regulated genes are documented in the literature (TABLE VI). These results demonstrate that the tape stripping method described here harvests RNA suitable for complete gene expression profiles of the skin that accurately reflect its pathological state.

Discussion

Recent advances in molecular medicine have made the possibility of molecular diagnosis a reality (Aitman 2001; Bertucci, Houlgatte et al. 2001; Galiegue and Casellas 2002; Lacroix, Zammatteo et al. 2002; Whipple and Kuo 2002; Satagopan and Panageas 2003). Through the use of microarrays and RNA profiling it is becoming increasingly clear that simple and complex cell populations can be monitored or "profiled" with the intent of understanding the physiologic state of those cells or tissues. This information is expected to lead to more accurate and possibly predictive diagnoses. This Example illustrates that the use of 4 small tape strips is an effective and non-invasive approach to capturing messenger RNA from the surface of skin and that this technique permits a direct quantitative and qualitative assessment of pathologic and physiologic biomarkers as a function of normal physiology.

The levels of IL-1β and IL-8 mRNA have been assayed semi-quantitatively relative to β-actin in normal, water and SLS-occluded skin sites and shown that RNA from tape and biopsy samples produce qualitatively similar results. In order to account for the possibility that changes in β-actin mRNA were responsible for observed changes in the interleukin/β-actin mRNA ratios, (Suzuki, Higgins et al. 2000; Bustin 2002; Tricarico, Pinzani et al. 2002) the levels of two housekeeping genes relative to each other were quantified. The resulting data (Tables I and II) showed that while the GAPDH/β-actin mRNA ratio is different in differently treated skin samples, the magnitude of this difference is not capable of explaining the observed changes in Il-1β and IL-8 mRNA levels. This fact is most clearly demonstrated by tape-harvest and biopsy data in which IL-1β and IL-8 mRNA are virtually undetectable in control samples but easily detected in SLS-treated samples, an observation that cannot be explained by minor changes in β-actin mRNA levels. In addition, IL-1β and IL-8 mRNAs and proteins have been well characterized in inflammation and are known to become elevated in response to SLS and other treatments (Paludan and Thestrup-Pedersen 1992; Grangsjo, Leijon-Kuligowski et al. 1996; Corsini and Galli 1998; Tomic-Canic, Komine et al. 1998; Freedberg, Tomic-Canic et al. 2001; Perkins, Osterhues et al. 2001; Cumberbatch, Dearman et al. 2002; Coquette, Berna et al. 2003). Thus data provided herein, from both tape and biopsy, are consistent with published observations.

Biopsy and tape harvesting are not equivalent sampling methods and therefore should not be expected to yield identical results. Tape harvest is restricted to the skin surface and therefore may preferentially recover vellus hair follicles and cells lining sebaceous, eccrine and sweat ducts as well as corneocytes (not predicted to contain RNA). Our method of using a single application of 4 individual tapes does not result in glistening of uninvolved skin and thus does not bare the viable epidermis. In contrast, a shave biopsy is expected to include not only cells of the epidermis (primarily keratinocytes and melanocytes and immune cells) but fibroblasts from the upper dermis. The potential enrichment of surface epidermis conveyed by our circular tape compared to a shave biopsy can be appreciated by considering that the surface area of a tape is 284 $mm^2$, while the surface area of a 2×2 mm shave biopsy is 4 $mm^2$. Thus we propose that tape-harvested cells represent an enrichment of a sub-population of cells found in a shave biopsy.

The data presented in Tables I and IV support the hypothesis that tape and biopsy-harvested RNA are derived from different cell populations. Table I shows highly significant p values when comparing $\Delta C_{t,\ GAPDH}$ values between tape and biopsy samples of SLS and uninvolved skin samples. Table IV demonstrates that $\Delta C_{t,\ IL-8}$ is highly significantly different (p<0.005) between tape and biopsy samples derived from normal, water or SLS-treated skin samples. In SLS-treated skin samples, the difference in average $\Delta C_{t,\ IL-8}$ values implies that IL-8/β-actin mRNA ratio is $2^{-(-0.89-4.13)}$ or 32-fold greater in tape versus biopsy-harvested RNA samples. In water-treated samples, the IL-8/β-actin mRNA ratio is on average $2^{-(1.54-9.22)}$ or at least 200-fold greater in tape-harvest RNA samples (data from Table IV). Similar, supportive data was also observed for $\Delta C_{t,\ IL-1\beta}$. This data implies that some differentially expressed biomarkers may be best detected in tape rather than biopsy-harvested epidermal samples.

Identification of biomarkers diagnostic of clinical irritation has been a long sought goal (Muller-Decker, Furstenberger et al. 1994; Boelsma, Gibbs et al. 1998; Muller-Decker, Heinzelmann et al. 1998; van Ruissen, Le et al. 1998; Komine, Rao et al. 2001; Perkins, Osterhues et al. 2001; Boxman, Hensbergen et al. 2002; Perkins, Cardin et al. 2002; Coquette, Berna et al. 2003). Changes in IL-1β and IL-8 mRNA are used herein as indicators of irritation and shown that most but not all irritated sites display increased levels of these normalized mRNA markers (Table III). The data also shows that tape-harvested and biopsy recovered RNA are qualitatively equal in their ability to reveal an irritant skin reaction. With respect to biopsy samples, it is clear that neither marker is 100% efficient at diagnosing irritation, a result observed for every biomarker proposed to be diagnostic of erythema and inflammation (Grangsjo, Leijon-Kuligowski et al. 1996; Muller-Decker, Heinzelmann et al. 1998; Chung, Marshall et al. 2001; Perkins, Osterhues et al. 2001; Boxman, Hensbergen et al. 2002). The current limitation of the tape harvest assay is the inefficiency in detecting certain markers in samples with limiting amounts of RNA, a subject discussed below. However, in comparison with the Sebutape assay (immunoassay of IL-8 protein; (Perkins, Osterhues et al. 2001) for irritation, which has a sensitivity (Hoffrage, Lindsey et al. 2000) of approximately 30%, mRNA biomarkers seem to possess superior potential. The observation that water occlusion produced increases of biomarker ratios in some subjects has been reported by others (Grangsjo, Leijon-Kuligowski et al. 1996; Howie, Aldridge et al. 1996; Perkins, Osterhues et al. 2001).

Results presented herein show that the tape stripping method harvests RNA suitable for DNA microarray experiments, and that these gene expression profiles reflect the pathological state of human skin, it should be possible to identify a subset of genes whose differential expression patterns can be correlated with different pathological states with a high degree of statistical accuracy. The fact that 1,700 differentially expressed genes have been identified with high statistical confidence sets the stage for the creation of small custom DNA arrays designed to identify patterns of gene expression diagnostic of irritant skin reactions, possibly diagnostic of different irritants and predictive of irritant reactions. The next step along this path is to identify the analogous set of genes expressed during an allergic skin response, identify genes unique to the irritant or allergic response and combine them into one DNA array, which could be used to determine if a mild reaction to a substance is irritant or allergic in nature. Such an array could also be used to test a variety of irritants and allergens for unique profiles.

Analysis of the top 100 genes differentially expressed in our SLS-treated samples shows that well over half of these genes have been implicated in injury and inflammation (TABLE VI), with most of these genes being up regulated. Interestingly, many of the down-regulated genes are hair keratins and keratin associated proteins selectively expressed in the hair during the anagen phase of the hair cycle. Either, the occlusive SLS treatment removes hair prior to the tape stripping or the treatment blocks anagen in the hair follicles.

It is shown in this example that RNA can be non-invasively and productively recovered from the surface of the skin using 4 small tape strips. The number of tape strips can be reduced, for example to two tape strippings, in conditions where the surface of the skin has been disrupted, such as SLS occlusion for 24 hours or in hyperproliferative skin conditions such as psoriasis (See Example 2). Furthermore, the limitation of capturing small amounts of RNA from some skin sites can be effectively overcome by obtaining replicate control samples and by the appropriate choice of mRNA biomarker (discussed below). Also presented herein, is data that the $\Delta C_t$ value, which is normally used to calculate a $\Delta\Delta C_t$ value (and thus a calibrated fold-change), is itself potentially useful for characterizing the physiologic state of the epidermis without reference to a calibration site.

The potential utility of $\Delta C_t$ values is illustrated by the $\Delta C_{t, IL-8}$ for subject 4's SLS-treated skin (tape-harvested sample; Table IV). That $\Delta C_t$ is −1.28, however it cannot be used to calculate a $\Delta\Delta C_t$ value (and therefore a fold-change) because insufficient RNA was recovered from the normal and water-occluded control sites. However, comparison of this $\Delta C_t$ value to the remaining subjects' average SLS $\Delta C_{t, IL-8}$ value of −0.89 and average values from tape-harvested water-occluded and uninvolved skin sites (>2.49 for normal or 1.54 for tape) is highly suggestive that the $\Delta C_t$ value of −1.28 is in fact indicative of irritated skin. For example, the value of −1.28 implies that, compared to the average value for the 10 subjects, subject 4's SLS-site IL-8/β-actin mRNA ratio is at least $2^{-(-1.28-2.49)}$ or 13.6-fold higher than the average value for uninvolved skin. A similar calculation using the average $\Delta C_{t, IL-8}$ for water-occluded samples as the calibrator suggests that the IL-8/actin mRNA ratio is $2^{-(-10.28-0.54)}$ or 7.1-fold elevated. These data lead to the hypothesis that establishment of a database of $\Delta C_t$ values for different mRNA biomarkers might be useful to identify a physiologic skin state without reference to an intrasubject control site. This utility of $\Delta C_t$ values is predicated upon the consistency of the PCR reaction conditions and the use of identical probes between samples. Given these prerequisites, our data support the potential for $\Delta C_t$ values being diagnostic indicators.

In this study the quantity of RNA recovered from different individuals and skin sites was variable, with significantly more RNA being recovered from SLS-treated sites than uninvolved skin sites. The large amount of RNA recovered from the SLS-irritated sites is consistent with the known effects of SLS, which effects invasion of inflammatory cells and creates a weakened barrier facilitating the removal of the inflamed epidermis. It has been found that RNA recovery is also a function of anatomical site and similar sites vary between individuals with respect to RNA yield.

While the variability of total RNA recovered does not affect the results of relative gene quantitation, the recovery of very small amounts of RNA did affect our ability to fully analyze some samples. In this respect, the choice of biomarkers may be as important as the amount of RNA recovered from a site. For instance, Table I shows that most tape-harvested samples could be assayed for β-actin and GAPDH mRNAs and thus calibrated GAPDH/actin ratios could be calculated. However, Table III reveals that some of these same samples do not have calibrated IL-1/actin or IL-8/actin mRNA ratios, with the IL-1β assay being the most affected. The reason for this difference between biomarker assays lies in the relative abundance of the specific mRNA. Because GAPDH mRNA is approximately equal in abundance to β-actin mRNA, all samples with detectable actin mRNA were successfully assayed for GAPDH. Likewise, a high success rate was achieved at calibrating IL-8/actin mRNA ratios in water and SLS treated tape-harvested skin samples because IL-8 message is relatively abundant in these samples. Thus the biomarker mRNA that is the most abundant will make the most efficient use of RNA mass. Therefore, candidate biomarker mRNAs should be chosen for best sensitivity, positive predictive value and high relative abundance when RT-PCR is to be used for detection and tape harvesting is to be the sampling method.

The present Example demonstrates the utility of tape-harvested RNA for semi-quantitative RT-PCR and microarray applications for several reasons. Both methods have particular advantages and are appropriate in different circumstances. The use of microarrays is an invaluable tool for the discovery of diagnostic and prognostic biomarker candidates and may be essential for subcategorizing disease states, which may demand simultaneous assay of hundreds of biomarkers. However, the use of microarrays is expensive and technically laborious. Quantitative RT-PCR is less expensive and less technically demanding and is appropriate for studies where a limited number of known markers are being studied.

In summary, the data of this Example show that the tape stripping method collects skin samples from normal and inflamed skin that are suitable for RNA isolation and gene expression profiling experiments. This method can be used to profile expression of a large number of genes in different skin conditions to design custom arrays that allow molecular diagnoses of skin disorders.

TABLE I $\Delta C_{t,GAPDH}$ values in tape and biopsy-harvested RNA samples from treated and untreated skin.

|  | $\Delta C_{t,GAPDH}$[a] | | | | | |
|---|---|---|---|---|---|---|
|  | Tape | | | Biopsy | | |
| Subject | Normal | Water | SLS | Normal | Water | SLS |
| 1 | 3.27 ± 0.36 | 2.04 ± 0.33 | 2.78 ± 0.44 | 0.1 ± 0.0.06 | 0.94 ± 0.09 | 1.61 ± 0.11 |
| 2 | 1.23 ± 0.17 | 1.41 ± 0.12 | 2.56 ± 0.11 | 0.99 ± 0.07 | 1.79 ± 0.12 | 1.95 ± 0.08 |
| 3 | 0.86 ± 0.15 | 1.54 ± 0.18 | 3.02 ± 0.08 | 0.73 ± 0.10 | 1.41 ± 0.11 | 1.44 ± 0.11 |
| 4 | — | — | 2.28 ± 0.10 | 0.46 ± 0.16 | 0.95 ± 0.11 | 1.68 ± 0.09 |
| 5 | — | 2.04 ± 0.23 | 3.15 ± 0.15 | 0.83 ± 0.10 | 1.69 ± 0.10 | 1.78 ± 0.10 |
| 6 | 2.97 ± 0.15 | 2.71 ± 0.23 | 2.87 ± 0.10 | 0.24 ± 0.07 | 1.48 ± 0.06 | 2.33 ± 0.07 |
| 7 | 0.91 ± 0.13 | 1.47 ± 0.10 | 2.68 ± 0.09 | 0.31 ± 0.10 | 1 ± 0.07 | 1.73 ± 0.09 |
| 8 | 1.83 ± 0.13 | 1.04 ± 0.15 | 3 ± 0.11 | 0.04 ± 0.04 | 1.38 ± 0.12 | 1.54 ± 0.10 |
| 9 | 0.7 ± 0.19 | 2.16 ± 0.34 | 2.85 ± 0.15 | 0.35 ± 0.08 | 1.6 ± 0.10 | 3.25 ± 0.08 |
| 10 | 3.47 ± 0.15 | 1.01 ± 0.12 | 2.46 ± 0.08 | 0.87 ± 0.09 | 1.77 ± 0.12 | 1.05 ± 0.07 |
| Average | 1.91 | 1.67 | 2.78 | 0.49 | 1.4 | 1.84 |
| (SD) | (1.35) | (0.35) | (0.04) | (0.34) | (0.33) | (0.6) |
| p value[b] (vs. normal) | — | 0.61 | 0.087 | — | <0.005 | <0.005 |
| p value[c] (vs. water) | 0.61 | — | <0.005 | <0.005 | — | 0.06 |
| p value[d] (biopsy vs. tape) | 0.014 | 0.28 | <0.005 | — | — | — |

$\Delta C_{t,GAPDH}$ is defined as [$C_{t,GAPDH} - C_{t,actin}$]; see Materials and Methods; mean ± SD; tape-harvested samples from uninvolved skin of subjects 4 and 5 and water-occluded skin (subject 4) did not have sufficient RNA for accurate β-actin assay.
The p value (2-sided, paired t-test) for water vs. normal and SLS vs. normal for biopsy and tape-harvested samples.
The p value for water vs. normal and water vs. SLS for biopsy and tape-harvested samples.
The p value for tape-harvested versus biopsy samples for normal, water and SLS-occluded skin.

TABLE II

GAPDH/actin mRNA ratios in EGIR and biopsy samples of normal, water and SLS-occluded skin.

|  | Relative GAPDH/β-actin mRNA change[a] | | | |
|---|---|---|---|---|
|  | EGIR | | Biopsy | |
| Subject | SLS | Water | SLS | Water |
| 1 [1] | 1.41 | 2.35 | 0.35 | 0.56 |
| 2 [3] | 0.4 | 0.88 | 0.51 | 0.58 |
| 3 [3] | 0.22 | 0.62 | 0.61 | 0.62 |
| 4 [2] | — | — | 0.43 | 0.72 |
| 5 [3] | — | — | 0.52 | 0.55 |
| 6 [4] | 1.07 | 1.19 | 0.24 | 0.42 |
| 7 [3] | 0.29 | 0.68 | 0.38 | 0.62 |
| 8 [3] | 0.44 | 1.72 | 0.35 | 0.4 |
| 9 [3] | 0.22 | 0.36 | 0.13 | 0.42 |
| 10 [4] | 2.02 | 5.48 | 0.88 | 0.54 |
| Average | 0.55 | 1.18 | 0.44 | 0.54 |

[a]Fold-increase of GAPDH/β-actin mRNA in the indicated sample relative to uninvolved skin; individual fold-changes calculated from data in Table I and average changes calculated from average values in Table I as described in Materials and Methods.

TABLE III

Summary of fold-changes in IL-1β/β-actin and IL-8/β-actin mRNA ratios relative to uninvolved skin.

|  | IL-1β/β-actin | | | | IL-8/β-actin | | | |
|---|---|---|---|---|---|---|---|---|
|  | Tape[b] | | Biopsy[b] | | Tape[b] | | Biopsy[b] | |
| Subject[a] | Water | SLS | Water | SLS | Water | SLS | Water | SLS |
| 1 [1] | ND | ND | 3.7** | 1 | ND | ND | ND | >1.1 |
| 2 [3] | 4.5** | >7.3**† | >1.4 | >28**† | 0.85 | 6**† | ND | 84**† |
| 3 [3] | ND | 18**† | ND | >15**† | 1.8 | 24**† | ND | >171**† |
| 4 [2] | — | NC | >2.7 | >3.3** | — | NC | ND | >12**† |
| 5 [3] | — | NC | ND | >8**† | >1.1 | >9.3**† | >1.5 | >101**† |
| 6 [4] | ND | >0.44 | >6.7** | >34**† | >6.3** | >6.8** | >10** | >778**† |
| 7 [3] | ND | >8.1**† | >3.1 | >11**† | >24** | >235**† | >1.4 | >42**† |
| 8 [3] | ND | >1.9** | 2.3 | 56**† | >1.4 | >41**† | >1.9 | >594**† |

TABLE III-continued

Summary of fold-changes in IL-1β/β-actin and IL-8/β-actin mRNA ratios relative to uninvolved skin.

|  | IL-1β/β-actin | | | | IL-8/β-actin | | | |
| --- | --- | --- | --- | --- | --- | --- | --- | --- |
|  | Tape[b] | | Biopsy[b] | | Tape[b] | | Biopsy[b] | |
| Subject[a] | Water | SLS | Water | SLS | Water | SLS | Water | SLS |
| 9 [3] | ND | >5** | >2 | >53**† | 22** | 18** | >5.2** | >368**† |
| 10 [4] | ND | >1.4 | 2.2** | 2.2** | 1.3 | >3** | ND | >1.1 |

[b]Subject identification followed by clinical score in brackets, score definitions are discussed in Materials and Methods.
[c]Fold-change is calculated from mean Ct values (IL-1β data not shown and IL-8 data in Table IV) as described in Materials and Methods.
The following abbreviations are used;
"—" indicates insufficient RNA recovered to accurately assay β-actin mRNA;
"ND" indicates IL-1β or IL-8 mRNA was not detected in the indicated sample (water or SLS);
NC indicates that the mRNA could be detected in the indicated sample but a calculation of fold-change could not be made due to low RNA recovery in the uninvolved skin sample;
a "**" signifies that the fold-change is significant at greater than 95% confidence;
a † designates that the fold-change is also significant when calculated relative to the water sample (data not shown);
a > symbol indicates that IL-1β or IL-8 mRNA could not be detected in the control sample, thus a minimum estimate of fold-change was calculated as described in Materials and Methods.

TABLE IV

ΔC$_t$ values for IL-8 mRNA in normal, water-occluded and SLS-occluded skin.

| | ΔC$_{t,IL-8}$[b] | | | | | |
| --- | --- | --- | --- | --- | --- | --- |
| | Normal | | Water | | SLS | |
| Subject[a] | Tape | Biopsy | Tape | Biopsy | Tape | Biopsy |
| 1 [1] | 1.51 ± 0.37 | >9.26 ± 0.06 | >1.28 ± 0.11 | >9.68 ± 0.13 | >1.51 ± 0.17 | 9.15 ± 0.15 |
| 2 [3] | 2.23 ± 0.17 | 8.22 ± 0.22 | 2.46 ± 0.19 | >11.30 ± 0.07 | −0.36 ± 0.05 | 1.82 ± 0.05 |
| 3 [3] | 2.08 ± 0.16 | >9.71 ± 0.06 | 1.26 ± 0.28 | >10.76 ± 0.11 | −2.59 ± 0.07 | 2.29 ± 0.13 |
| 4 [2] | — | >10.16 ± 0.10 | — | >10.53 ± 0.10 | −1.28 ± 0.11 | 6.56 ± 0.10 |
| 5 [3] | — | >9.72 ± 0.05 | 0.03 ± 0.27 | 9.09 ± 0.31 | −3.05 ± 0.15 | 3.06 ± 0.11 |
| 6 [4] | >2.7 ± 0.08 | >10.36 ± 0.09 | 0.05 ± 0.13 | 7.00 ± 0.27 | −0.05 ± 0.11 | 0.76 ± 0.13 |
| 7 [3] | >7.20 ± 0.13 | >10.52 ± 0.06 | 2.62 ± 0.14 | 10.06 ± 0.28 | −0.68 ± 0.08 | 5.11 ± 0.06 |
| 8 [3] | >4.91 ± 0.18 | >10.89 ± 0.08 | 4.46 ± 0.32 | 10.00 ± 0.4 | −0.44 ± 0.06 | 1.67 ± 0.08 |
| 9 [3] | 4.15 ± 0.28 | >9.58 ± 0.09 | −0.30 ± 0.18 | 9.94 ± 0.28 | 0.02 ± 0.17 | 1.06 ± 0.07 |
| 10 [4] | >2.12 ± 0.11 | >10.00 ± 0.07 | 1.70 ± 0.29 | >10.31 ± 0.12 | 0.56 ± 0.07 | 9.81 ± 0.26 |
| Average | 2.49 | >9.84 | 1.54 | 9.22 | −0.89 | 4.13 |
| p value (tape vs. biopsy)[c] | | | — | <0.005 (n = 5) | — | <0.005 (n = 9) |

[d]Subject ID and clinical score of SLS site in brackets; scoring is described in Materials and Methods.
[e]ΔC$_t$ and minimum ΔC$_t$ calculations are described in Materials and Methods; an entry of "—" indicated that insufficient RNA was recovered to provide a meaningful estimate of the indicated ΔC$_t$. A value preceded by ">" indicates that the mRNA for IL-1β or IL-8 was not detected in the sample, therefore the respective C$_t$ was assigned a value of 37 and a minimum ΔC$_t$ is given (i.e. ΔC$_t$ = 37 − C$_{t,actin}$).
[f]Two-way, paired t-test comparing ΔC$_t$ for tape versus biopsy for a given skin treatment.

TABLE V

Percentage of the measurement of gene expression level unchanged for each of all possible pair-wise comparisons among GeneChips (A5, A6, A9, C1, C2, and C3) hybridized with aRNA obtained from three different locations on the upper back of two subjects (A and C).

| | Gene Chip/Subject ID | | | | | |
| --- | --- | --- | --- | --- | --- | --- |
| | A5 | A6 | A9 | C1 | C2 | C3 |
| A5 | 100% | | | | | |
| A6 | 88.90% | 100% | | | | |
| A9 | 90.80% | 86.10% | 100% | | | |
| C1 | 89.80% | 88.20% | 87.40% | 100% | | |
| C2 | 85.00% | 85.30% | 83.10% | 89.60% | 100% | |
| C3 | 88.00% | 88.00% | 87.30% | 88.90% | 83.70% | 100% |

TABLE VI

Functional grouping of top 100 differentially expressed genes between untreated and SLS treated conditions with p-values less than $1.4 \times 10^{-10}$ and PPDE(p) values greater than 0.99.

| Accession Number | Gene Name | Fold | Reference if Known Involvement in Injury/Inflammation |
|---|---|---|---|
| | Structural proteins: | | |
| X99142.1 | Hair keratin, hHb6 | −167.9 | |
| AJ406939.1 | Keratin associated protein 4.7 (KRTAP4.7) | −51.9 | |
| BF740152 | Myosin IE | 26.2 | |
| NM_000381.1 | Midline 1 (OpitzBBB syndrome) (MID1) | −32.9 | |
| NM_030966.1 | Keratin associated protein 1.3 (KRTAP1.3) | −42.6 | |
| Z24727.1 | Tropomyosin 1 (alpha) | −17.8 | |
| NM_002275.1 | Keratin 15 (KRT15) | −26.2 | (Raval, Bharadwaj et al. 2003) |
| NM_030975.1 | Keratin associated protein 9.9 (KRTAP9.9) | −859.3 | |
| | Proteinases and protease inhibitors: | | |
| L10343 | Elafin/skin derived protease inhibitor 3 (SKALP) | 57.8 | (Molhuizen and Schalkwijk 1995) |
| NM_002422.2 | Metalloproteinase 3 (Stromelysin 1) | 109.9 | (Pilcher, Wang et al. 1999; Fray, Dickinson et al. 2003) |
| NM_003254.1 | Tissue inhibitor of metalloproteinase 1 (TIMP1) | 35.1 | (Lobmann, Ambrosch et al. 2002) |
| NM_001109.1 | Disintegrin and metalloproteinase domain 8 (ADAM8) | 97.1 | (Kahari and Saarialho-Kere 1997) |
| NM_000362.2 | Tissue inhibitor of metalloproteinase 3 (TIMP3) | −29.7 | (Lobmann, Ambrosch et al. 2002) |
| U08839.1 | Urokinase-type plasminogen activator receptor | 19.3 | (Chung, Lee et al. 1996) |
| NM_004994.1 | Matrix metalloproteinase 9 (gelatinase B) | 24.2 | (Kahari and Saarialho-Kere 1997; Herouy 2001) |
| NM_001912.1 | Cathepsin L (CTSL) | 18.5 | (Kawada, Hara et al. 1997; Benavides, Starost et al. 2002; Welss, Sun et al. 2003) |
| NM_000129.2 | Coagulation factor XIII, A1 polypeptide (F13A1) | 20.4 | (Chung, Lee et al. 1996; Ichinose 2001) |
| NM_001150.1 | Alanyl (membrane) aminopeptidase (aminopeptidase N/CD13) | 35.3 | (Lendeckel, Arndt et al. 2003) |
| | Cytokines, chemokines and their receptors: | | |
| NM_002984.1 | Small inducible cytokine A4 (SCYA4) | 136.3 | (Asadullah, Sterry et al. 2002; Dong, McDermott et al. 2003) |
| NM_003856.1 | Interleukin 1 receptor-like 1 (IL1RL1) | 89.4 | (Asadullah, Sterry et al. 2002; Dong, McDermott et al. 2003) |
| AI421071 | Chemokine (C—C motif) receptor 1 | 334.7 | (Asadullah, Sterry et al. 2002; Dong, McDermott et al. 2003) |
| NM_002090.1 | GRO3 oncogene | 74.2 | (Asadullah, Sterry et al. 2002; Dong, McDermott et al. 2003) |
| NM_000640.1 | Interleukin 13 receptor, alpha 2 (IL13RA2) | 53.6 | (Asadullah, Sterry et al. 2002; Dong, McDermott et al. 2003) |
| R64130 | Pro-platelet basic protein | 66.6 | (Asadullah, Sterry et al. 2002; Dong, McDermott et al. 2003) |
| NM_001511.1 | GRO1 oncogene (melanoma growth stimulating activity, alpha) | 26.7 | (Asadullah, Sterry et al. 2002; Dong, McDermott et al. 2003) |
| NM_001838.1 | Chemokine (C-C motif) receptor 7 (CCR7) | 25.5 | (Asadullah, Sterry et al. 2002; Dong, McDermott et al. 2003) |
| NM_001558.1 | Interleukin 10 receptor, alpha (IL10RA) | 171.1 | (Asadullah, Sterry et al. 2002; Dong, McDermott et al. 2003) |
| NM_001562.1 | Interleukin 18 | −13.8 | (Asadullah, Sterry et al. 2002; Dong, McDermott et al. 2003) |

TABLE VI-continued

Functional grouping of top 100 differentially expressed genes between untreated and SLS treated conditions with p-values less than $1.4 \times 10^{-10}$ and PPDE(p) values greater than 0.99.

| Accession Number | Gene Name | Fold | Reference if Known Involvement in Injury/Inflammation |
|---|---|---|---|
| NM_006850.1 | Suppression of tumorigenicity 16/Il-24 | 65.7 | (Asadullah, Sterry et al. 2002; Dong, McDermott et al. 2003) |
| NM_000576.1 | Interleukin 1, beta (IL1B) | 17.2 | (Asadullah, Sterry et al. 2002; Dong, McDermott et al. 2003) |
| NM_006273.2 | Small inducible cytokine A7 (SCYA7) | 44 | (Asadullah, Sterry et al. 2002; Dong, McDermott et al. 2003) |
| Complement and complement receptors: | | | |
| NM_012072.2 | Complement component C1q receptor (C1QR) | 78.7 | (Verhoef 1991; Bayon, Alonso et al. 1998) |
| NM_001736.1 | Complement component 5 receptor 1 (C5R1) | 121.5 | (Verhoef 1991; Bayon, Alonso et al. 1998) |
| U62027.1 | Anaphylatoxin C3a receptor | 51.5 | (Verhoef 1991; Bayon, Alonso et al. 1998) |
| Histocompatibility complex: | | | |
| NM_021983.2 | Major histocompatibility complex, class II, DR beta 4 (HLA-DRB4) | 26.7 | (Alberts, Bray et al. 1994) |
| AJ297586.1 | MHC class II antigen (HLA-DRB1 gene) | 37.1 | (Alberts, Bray et al. 1994) |
| X76775 | Major histocompatibility complex, class II, DM alpha (HLA-DMA) | 42 | (Alberts, Bray et al. 1994) |
| M27487.1 | MHC class II DPw3-alpha-1 chain | 32.8 | (Alberts, Bray et al. 1994) |
| M60334.1 | MHC class II HLA-DR-alpha | 23.7 | (Alberts, Bray et al. 1994) |
| NM_002118.1 | Major histocompatibility complex, class II, DM beta (HLA-DMB) | 18.3 | (Alberts, Bray et al. 1994) |
| AA807056 | Major histocompatibility complex, class II, DR beta 3 | 24.4 | (Alberts, Bray et al. 1994) |
| AF005487.1 | MHC class II antigen (DRB6) | 22.4 | (Alberts, Bray et al. 1994) |
| Growth factors: | | | |
| NM_003862.1 | Fibroblast growth factor 18 (FGF18) | −21.8 | |
| NM_013959.1 | Neuregulin 1 (NRG1) | 23.3 | (Vermeer, Einwalter et al. 2003) |
| Receptors and cell surface ligands: | | | |
| NM_013252.1 | C-type lectin, superfamily member 5 (CLECSF5) | 75.4 | (Kilpatrick 2002) |
| NM_000560.1 | CD53 antigen | 94.6 | (Alberts, Bray et al. 1994) |
| Z22969.1 | CD163 antigen/M130 antigen | 63.4 | (Alberts, Bray et al. 1994) |
| NM_018643.1 | Triggering receptor expressed on myeloid cells 1 (TREM1) | 55.2 | (Colonna 2003) |
| Y00062.1 | CD45/T200 leukocyte common antigen | 61.9 | (Alberts, Bray et al. 1994) |
| NM_002438.1 | Mannose receptor, C type 1 (MRC1) | 69.8 | (Baker, Ovigne et al. 2003) |
| NM_004106.1 | Fc fragment of IgE, high affinity I, receptor (FCER1G) | 51 | (Alberts, Bray et al. 1994) |
| NM_005849.1 | Immunoglobulin superfamily, member 6 (IGSF6) | 44.5 | (Alberts, Bray et al. 1994) |
| NM_004951.1 | Epstein-Barr virus induced gene 2 (lymphocyte-specific G protein-coupled receptor) (EBI2) | 34.9 | (Alberts, Bray et al. 1994) |
| BG236280 | CD86 antigen | 23.9 | (Alberts, Bray et al. 1994) |
| AF313468.1 | Dendritic cell-associated C-type lectin-1 | 25.6 | (Kilpatrick 2002) |
| NM_003264.1 | Toll-like receptor 2 (TLR2) | 28.5 | (Alberts, Bray et al. 1994) |
| NM_016184.1 | C-type lectin, superfamily member 6 (CLECSF6) | 19.9 | (Kilpatrick 2002) |
| NM_005211.1 | Colony stimulating factor 1 receptor | 37.4 | (Alberts, Bray et al. 1994) |
| NM_001828.3 | Charcot-Leyden crystal protein/Galectin-10 | 117.2 | (Ackerman, Liu et al. 2002) |
| NM_002003.2 | Ficolin 1 (FCN1) | 17.6 | (Alberts, Bray et al. 1994) |
| M98399.1 | CD36 | 81.7 | (Alberts, Bray et al. 1994) |
| Membrane transport: | | | |
| NM_022003.1 | FXYD domain-containing ion transport regulator 6 (FXYD6) | −42.3 | |

TABLE VI-continued

Functional grouping of top 100 differentially expressed genes between untreated and SLS treated conditions with p-values less than $1.4 \times 10^{-10}$ and PPDE(p) values greater than 0.99.

| Accession Number | Gene Name | Fold | Reference if Known Involvement in Injury/Inflammation |
|---|---|---|---|
| NM_006931.1 | Solute carrier family 2 (facilitated glucose transporter), member 3 (SLC2A3) | 48.3 | |
| *Intracellular signal transduction:* | | | |
| NM_005335.1 | Cell-specific Lyn substrate 1 (HCLS1) | 35.8 | |
| NM_003332.1 | TYRO protein tyrosine kinase binding protein (TYROBP) | 219.3 | (Lucas, Daniel et al. 2002) |
| NM_002463.1 | Myxovirus (influenza) resistance 2 | 30.1 | (Melen, Keskinen et al. 1996) |
| AI123251 | Lymphocyte cytosolic protein 2 | 140.1 | |
| NM_002048.1 | Growth arrest-specific 1 (GAS1) | −76.6 | |
| AF183421.1 | Small GTP-binding protein rab22b | 22.9 | |
| AI356412 | v-yes-1 Yamaguchi sarcoma viral related oncogene homolog | 27.3 | |
| AF039555.1 | Visinin-like protein 1 (VSNL1) | −12.5 | |
| BC002671.1 | Dual specificity phosphatase 4 | 41.8 | |
| NM_014380.1 | p75NTR-associated cell death executor | −8.1 | |
| *Enzymes:* | | | |
| NM_003364.1 | Uridine phosphorylase (UP) | 46.3 | |
| NM_002933.1 | Ribonuclease, RNase A family, 1 (RNASE1) | 86.7 | |
| NM_005746.1 | Pre-B-cell colony-enhancing factor (PBEF) | 35.5 | (Samal, Sun et al. 1994) |
| NM_000382.1 | Aldehyde dehydrogenase 3 family, member A2 (ALDH3A2) | −17.2 | |
| NM_021615.1 | Carbohydrate (N-acetylglucosamine 6-O) sulfotransferase 6 (CHST6) | 68.3 | |
| W46388 | Superoxide dismutase 2, mitochondria | 15.6 | |
| *Extracellular matrix associated proteins:* | | | |
| NM_002727.1 | Proteoglycan 1, secretory granule (PRG1) | 65.3 | |
| NM_004385.1 | Chondroitin sulfate proteoglycan 2 (versican) | 30.8 | (Syrokou, Dobra et al. 2002) |
| X77598.1 | Laminin alpha 3 chain (LAM A3) | 18.7 | |
| BF055462 | Thrombospondin 1 | 55.5 | (Vallejo, Mugge et al. 2000) |
| *Transcription factors:* | | | |
| AU145890 | Forkhead box C1 | −18.8 | |
| BC001283.1 | Nuclear factor IB | −11.5 | |
| *Others:* | | | |
| AF245505.1 | Adlican | −65.4 | |
| U03891.2 | Phorbolin 1 | 52.7 | |
| NM_020987.1 | Ankyrin 3, node of Ranvier (ankyrin G) (ANK3) | −42.3 | |
| NM_006762.1 | Lysosomal-associated multispanning membrane protein-5 (LAPTM5) | 41.2 | |
| U56725.1 | Heat shock 70 kD protein 2 | −26.2 | |
| NM_001442.1 | Fatty acid binding protein 4, adipocyte (FABP4), | 29 | |
| NM_014583.1 | LIM and cysteine-rich domains 1 (LMCD1) | −25.4 | |
| NM_015714.1 | Putative lymphocyte G0G1 switch gene (G0S2) | 52.8 | |
| NM_005410.1 | Selenoprotein P (SEPP1) | −16 | |
| NM_002965.2 | S100 calcium-binding protein A9 (calgranulin B) | 21.8 | (Kerkhoff, Eue et al. 1999; Thorey, Roth et al. 2001) |
| BC006471.1 | ALL1-fused gene from chromosome 1q | −14.8 | |
| NM_006332.1 | Interferon, gamma-inducible protein 30 (IFI30) | 31.4 | (Phan, Lackman et al. 2002) |

TABLE VI-continued

Functional grouping of top 100 differentially expressed genes between untreated and SLS treated conditions with p-values less than $1.4 \times 10^{-10}$ and PPDE(p) values greater than 0.99.

| Accession Number | Gene Name | Fold | Reference if Known Involvement in Injury/ Inflammation |
|---|---|---|---|
| AF063606.1 | Brain my048 protein | −63.1 | |
| NM_006851.1 | Glioma pathogenesis-related protein (RTVP1) | 78.2 | |
| AA149745 | Tripartite motif protein TRIM2 | −15.4 | |

EXAMPLE 3

Non-Invasive Isolation of Epidermal RNA from Psoriatic Patients Using Tape Stripping Method Provided Herein This example illustrates the isolation and detection of nucleic acids from psoriatic lesions and the identification of genes whose expression is associated with psoriatic lesions. This example summarizes the results of tape harvesting lesional and non-lesional skin in 24 psoriatic patients in various treatment stages. The goal of this investigational work was to determine if Derm Tech's Epidermal Genetic Information Retrieval Technology (EGIR), which is a tape disk used with a synthetic rubber-based adhesive (Adhesive Research, Glen Rock, Pa.) on a polyurethane film (Product No. 90068), could successfully recover RNA from the surface of lesional and non-involved skin from psoriatic patients; and to semi-quantitate recovered RNA for specific mRNA molecules known to be elevated in psoriatic lesions. The data generated from these patients demonstrates that RNA can be recovered and that mRNAs for TNFα, IFNγ, CD2, GAPDH, and β-actin can be detected and semi-quantitated in tape harvested epidermal samples. Nanogram quantities of RNA were recovered from 92% of tape harvested psoriatic plaques. Recovery of RNA from non-involved control skin was less successful with a 31% success rate. The recovery of RNA from non-lesional skin was not random because some subjects could be tape harvested with repeated success while others could not. The recovery of RNA from non-lesional psoriatic skin contrasts with the success of tape harvesting normal skin of healthy individuals, which has an 85% success rate. Semi-quantitative RT-PCR analysis demonstrated that at least 6 patients had significantly elevated TNFα mRNA levels in psoriatic plaques, 4 patients had elevated IFNγ mRNA and 3 had increased CD2 message relative to β-actin. 18 patients could not have the relative change of any marker assayed in psoriatic lesions because of insufficient RNA collection from control skin. However, analysis of ΔC$_t$ values in 21 patient's lesions demonstrated a highly significant difference between TNFα and CD2 mRNA levels relative to β-actin in psoriatic versus control skin. These data suggest that TNFα and CD2 mRNA were in fact elevated in most patients and that patients could be categorized into two groups, those with elevated TNFα and CD2 mRNA and those with elevated TNFα, CD2 and IFNγ mRNAs. The data demonstrate that there are distinct relative abundances of the 3 mRNAs with respect to β-actin in psoriatic versus non-lesional skin, differences which are common across subjects. These preliminary results are very encouraging and demand confirmation with additional patients.

Materials and Methods

Clinical: Sample collection was done at the University of Utah in collaboration with Dr. Gerald Krueger. For each body site a total of 4 fresh tapes were sequentially applied once to a single site and removed. Tapes were put into individual eppendorf tubes, frozen at −80 and express mailed on dry ice to DermTech International where all subsequent analysis was performed. The tape used for tape stripping was a synthetic rubber-based adhesive MA70 (Adhesive Research) on a polyurethane film.

Isolation of RNA: Total RNA was isolated using our standard method and the RNeasy fibrous tissue kit (Qiagen). The 4 tapes used to harvest each site were combined in buffer RLT and extracted together according to the manufacturer's guidelines using our standard adaptations.

Quantitation of RNA mass: Samples were quantified by non-competitive semi-quantitative RT-PCR using a fluorescence-based 5'-nuclease assay ("Real-time" PCR) on an ABI 7000 or 7900. Each sample was reverse transcribed in triplicate and each cDNA amplified and quantified in duplicate; the resulting 6 C$_t$ values were converted to RNA masses, which were averaged to yield the data in Table 1. C$_t$ values were converted to RNA masses using the standard curve method. A standard curve was generated with total RNA from human spleen. The accuracy of this method assumes that the relative amount of β-actin in human spleen RNA is identical to that in skin samples recovered by tape stripping. All assays were performed using Predeveloped Assay Reagents purchased from Applied Biosystems. The data from the first 11 subjects (Sample Sets 1 and 2) was gathered using multiplex assays (same tube assay of actin and the mRNA of interest). Thereafter, all analyses have been done in a single tube single analysis format. All ΔC$_t$ and ΔΔC$_t$ calculations are done with C$_t$ values determined during the same experiment (i.e. simultaneous amplification/detection).

Semi-quantitation of mRNA levels: Messenger RNA (mRNA) levels were semi-quantified for GAPDH, TNFα, IFNγ, and CD2 using non-competitive RT-PCR and the comparative (ΔΔC$_t$ method; 5'-nuclease assay). In the ΔΔC$_t$ method individual mRNAs ("mRNA$_x$" i.e. the RNA-of-interest) are semi-quantified by normalization to β-actin mRNA (mRNA$_a$) and this ratio is divided by the similar ratio from an uninvolved skin site, a step referred to as "calibration". The resulting number is an indication of the change of (mRNA$_x$/mRNA$_a$) in lesional versus non-lesional skin.

Background of the ΔΔC$_t$ method (Parts of the following discussion and additional information not discussed here can be found in ABI User Bulletin #2, which can be found at: http://docs.appliedbiosystems.com/pebiodocs/04303859.pdf): During amplification of a sample using fluorescence detection and the 5'-nuclease assay, the net (background corrected) fluorescence of a sample is directly related to the amount of PCR product synthesized, which is related to the initial amount of specific mRNA in the sample. This fluorescence, called ΔR$_n$, is related to the amount of PCR product by the equation:

$$\Delta R_n \propto X_T = X_0 2^C \qquad 1]$$

where X$_T$ is the amount of total PCR product at cycle C and X$_0$ is the initial amount of mRNA$_x$. During the PCR reaction, $\Delta R_n$ rises exponentially (under non-competitive conditions in the early stages of the reaction); when $\Delta R_n$ rises significantly above background, it is said to have reached a threshold value and equation 1] becomes:

$$\Delta R_{N,x} = K_x X_0 2^{C_{t,x}} \qquad 2]$$

where $K_x$ is a spectroscopic constant specific to the fluorescent probe and the reaction conditions and $C_{t,x}$ (the threshold value) is the number of PCR cycles required to reach the threshold fluorescence $\Delta R_n$. A similar equation can be written for the normalization mRNA, which in this case is β-actin:

$$\Delta R_{N,A} = K_A A_0 2^{C_{t,A}} \qquad 3]$$

where $K_A$ is an actin specific constant and $A_o$ is the initial number of actin mRNA molecules. By dividing equation 2 by 3 and rearranging, we obtain an equation relating the fraction of $mRNA_x$ to β-actin mRNA in our unknown or "experimental" sample:

$$\left(\frac{X_0}{A_0} = \frac{\Delta R_{n,X}}{\Delta R_{n,A}} K_{AX} 2^{-\Delta C_{T,Exp}}\right)_{Exp} \qquad 4]$$

where $K_{AX} = K_A/K_X$ and $\Delta C_{t,Exp} = C_{t,X} - C_{t,A}$. This equation relates the initial (unknown) number of mRNA molecules to the experimentally determined threshold cycle number. From the equation, we can see that the ratio of the two mRNAs is not only a function of the experimentally derived $C_t$ values but also a function of the constant $K_{AX}$ (an unknown), and the two $\Delta R_n$ values, which are determined and reported by the instrument. Thus without knowledge of $K_{AX}$, the comparative method does not reveal the absolute ratio of two mRNAs in a single sample. However, by writing a similar equation for a second "calibrator" sample $$\left(\frac{X_o^{Cal}}{A_o^{Cal}} = \frac{\Delta R_{n,X}^{Cal}}{\Delta R_{n,A}^{Cal}} K_{AX} 2^{-\Delta C_T^{Cal}}\right)_{Cal} \qquad 5]$$

and dividing equation 4 by 5 we obtain:

$$\frac{X_0}{A_0} \Big/ \frac{X_0^{Cal}}{A_0^{Cal}} = \left(\frac{\Delta R_{n,X}}{\Delta R_{n,A}}\right) K_{AX} 2^{-\Delta C_{t,Exp}} \Big/ \left(\frac{\Delta R_{n,X}^{Cal}}{\Delta R_{n,A}^{Cal}}\right) K_{AX} 2^{-\Delta C_{t,Cal}} \qquad 6]$$

If the experimental and calibrator samples are analyzed during the same experiment, the threshold values are equal $\Delta R_{n,x} = \Delta R_{n,x}^{Cal}$ and $\Delta R^{n,A} = \Delta R_{n,A}^{Cal}$, and because $K_{AX}$ is identical for both samples, equation 6 simplifies to:

$$\left(\frac{X_0}{A_0}\right)\left(\frac{A_0^{Cal}}{X_0^{Cal}}\right) = 2^{-\Delta \Delta C_t} \qquad 7]$$

where $\Delta \Delta C_t = \Delta C_{t,exp} - \Delta C_{t,cal}$, recalling that $\Delta C_{t,exp}$ is $C_{t,x} - C_{t,actin}$ for the experimental sample and $\Delta C_{t,cal}$ is the analogous difference for the calibrator sample. Thus equation 7 allows us to infer a change of $mRNA_x/mRNA_a$ between the sample of interest (psoriatic tissue) and a calibrator sample (non-lesional skin) directly from C, measurements. Note that if one adds the further assumption that the "housekeeping" gene does not change its expression relative to total RNA then equation 7 simplifies to:

$$\left(\frac{X_0}{X_0^{Cal}}\right) = 2^{-\Delta \Delta C_t} \qquad 8]$$

It should be noted that this final simplification is not necessary to draw significance from $C_t$ values for diagnostic purposes.

Analysis of $\Delta C_t$ values without calibration: The $\Delta \Delta C_t$ method requires the use of a calibrator sample to eliminate unknown constants in Equation 4 and relate the $\Delta C_t$ values directly to mRNA levels in the two samples. It would be advantageous to be able to analyze $\Delta C_t$ values without the necessity of a calibrator sample. Equation 4 seems to offer several means of doing this. Equation 4 relates $X_0/A_0$ to $\Delta C_t$; if one could experimentally change this ratio (for instance by using in vitro transcribed RNA) then a graph of $\Delta C_t$ vs. log $[X_0/A_0]$ should have a slope related to the known $\Delta R_n$'s and the unknown $K_{AX}$, which could be solved for $K_{AX}$, which in turn could be used to directly relate $\Delta C_t$ to $mRNA_x/mRNA_a$ in a sample without calibration.

An alternative strategy is to inspect equation 4 for the variables which contribute to the observed $\Delta C_t$ and assess their contributions to it. By taking the log of equation 4 we obtain:

$$\log\left(\frac{X_0}{A_0}\right) = \log\left(\frac{\Delta R_{n,X}}{\Delta R_{n,A}} K_{AX} 2^{-\Delta C_{T,Exp}}\right) \qquad 9]$$

$$= \log\left(\frac{\Delta R_{n,X}}{\Delta R_{n,A}}\right) + \log K_{AX} + \log 2^{-\Delta C_{T,Exp}}$$

$$= \log\left(\frac{\Delta R_{n,X}}{\Delta R_{n,A}}\right) + \log K_{AX} - \Delta C_{T,Exp} \log 2$$

solving equation 9 for $\Delta C_t$ yields $$\Delta C_{T,Exp} = \frac{-\log\left(\frac{X_0}{A_0}\right) + \log\left(\frac{\Delta R_{n,X}}{\Delta R_{n,A}}\right) + \log K_{AX}}{\log 2} \qquad 10]$$

We can see that $\Delta C_{t,Exp}$ depends on 3 factors; $X_0/A_0$; $\Delta R_{n,x}/\Delta R_{n,A}$; and $K_{AX}$. If we compare two samples analyzed during the same experiment, the $\Delta R_n$ values will be identical and cannot contribute to changes in the $\Delta C_t$. Likewise, since the $K_{AX}$ values are identical we can see that $\Delta C_t$ values will only change if $X_0/A_0$ changes. Therefore, under same plate measurements, it is valid to compare $\Delta C_t$ values without a calibration step. A logical extension is to ask if $\Delta C_t$ measurements from separate experiments can be compared. In such an event it is likely that $\Delta R_n$'s will be different, however equation 10 allows one to calculate an adjusted $\Delta C_t$ that will reflect the effect of differing $\Delta R_n$ values. Rearrangement of equation 10 gives:

$$\Delta C_{T,Exp} - \frac{\log\left(\frac{\Delta R_{n,X}}{\Delta R_{n,A}}\right)}{\log 2} = \frac{-\log\left(\frac{X_0}{A_0}\right) + \log K_{AX}}{\log 2} \qquad 11]$$

The expression to the left of the equality in equation 11 is an "adjusted" $\Delta C_t$ which accounts for differing $\Delta R_n$'s. We can see that the adjusted $\Delta C_t$ only depends on $A_0/X_0$ and $K_{AX}$. In this case $K_{AX}$ will be constant for both samples—given identical reaction conditions and probes—and any differences between adjusted $\Delta C_t$'s will be a consequence of differences in $X_0/A_0$.

Data handling and statistical analysis: For each mRNA assay we have 6 replicate measurements of the $C_t$. The average of these $C_t$ values is used to calculate the $\Delta C_{t,x}$ for the sample and calibrator. It is our experience that as $C_t$ values approach 37 cycles, individual assays can produce undetectable readings or $C_t$ values >37 with high variability. In order to deal with combinations of undetectable and readings greater than 37 with high standard deviations, we have adopted the following data management rules. Rule 1] if there are 4 or more readings (out of 6 replicates) of undetectable, a $C_t$ value of 37 (our limit of detection) is assigned to the sample; Rule 2] if an average $C_t$ is greater than or equal to 37 and the standard deviation is greater than or equal to 1, a value of $C_t=37$ is assigned to the mRNA being measured. This last rule simply states that if an mRNA is at our limit of detection or reliable quantitation, we simply define it as undetectable in order to estimate its maximum value. Calculations performed with $C_t=37$, where that value has been assigned by the above rules, are indicated by enclosing the resulting data in parentheses. Outlier measurements are defined as outside the average of remaining measurements ±3 standard deviations. If a single measurement lies outside this boundary it is eliminated from the calculations. An $mRNA_x/mRNA_a$ ratio is considered statistically different than the control value (at 95% confidence) if the fold-change given by $2^{-\Delta\Delta Ct \pm 2 std\ dev}$ does not overlap the control range given by $2^{\pm 2 std\ dev}$.

Results

RNA Yield

Table 1 shows the yields of total RNA from non-lesional and lesional skin in 24 patients. It is our experience with tape harvesting that yields of less than 200 picograms are not useful for quantitating mRNA levels 8-fold less abundant than β-actin. By applying this standard of at least 200 picograms, we can categorize RNA recovery as successful or not successful. Table 2 summarizes the results of categorizing the mass data by the 200-picogram criterion. We can see that tape harvesting lesional skin was very successful with 91% of samples having sufficient RNA for analysis. However, tape harvesting of non-lesional skin was less successful (31% success).

Because analysis of the second sample set suggested that non-lesional skin might present recovery problems, subsequent sample sets included 2 non-lesional skin sites as controls. A total of 12 patients each had 2 control sites tape harvested. Of these 12 pairs of sites, 9 pairs produced insufficient RNA and 3 pairs produced nanogram quantities of RNA (Table 1). There were no pairs of mixed sites. This data strongly suggests that the recovery of RNA from uninvolved skin is not a random occurrence but that some patients may in fact yield less RNA. A similar observation applies to the skin of subjects with no psoriasis. However, the frequency of successful recovery from healthy subjects' normal skin is 84%. This contrasts quite strongly with the 31% recovery from non-lesional psoriatic skin. We conclude that 1] the uninvolved skin of psoriatic patients is different at the level of ability to recover RNA from the surface of the skin; and 2] that these 12 psoriatic patients can be divided into two categories based on the ability to recover RNA from non-lesional skin. A caveat to this second conclusion is that body location may be an important factor and the particular sites harvested have not yet been reported. It will be of interest to understand the differences between psoriatic patients who either do or do not yield RNA from non-lesional skin using EGIR adhesive films.

Relative Cytokine Levels

Table 3 reveals the relative increases in mRNAs for TNFα, IFNγ, and CD2 in lesional compared to non-lesional skin. Table 3 shows that 6 patients had significantly elevated TNFα/β-actin mRNA ratios compared to non-lesional skin. In 15 patients we were unable to classify the TNF/actin mRNA ratio as elevated or not because of poor RNA recovery from the control site.

The data for IFNγ shows 3 patients having elevated IFNγ/actin mRNA ratios and 18 patients having no conclusion because of inadequate control data. Data for CD2 reveals that 3 patients had elevated CD2/actin mRNA levels, 2 had normal or borderline elevated levels (possible 2.4-fold increases) and 16 samples were indeterminate.

Discussion

In this work we have analyzed the results of tape harvesting psoriatic and non-lesional skin on 24 patients. We have quantified the RNA recovered and shown that when sufficient RNA is recovered, it can be productively analyzed. We have found that RNA can be recovered with high frequency from psoriatic plaques, while RNA is recovered with below average frequency (compared to healthy subjects) from non-lesional skin. While it seems clear that recovery of RNA from non-lesional skin is patient specific, we have not eliminated the possibility that body site plays a major role in RNA recovery. The inability to efficiently collect non-lesional skin data from psoriatic patients would seem to be an obstacle to the analysis of lesions (Table 3). However, the ultimate goal of this work is to devise an assay which requires only a lesion sample and no control skin (discussed below). Because such a goal requires a foundational database of $\Delta C_t$ values from non-lesional skin, or at the very least normal skin, we will continue to pursue ideas to increase the isolation of RNA from non-lesional skin.

Several strategies can possibly be used for increasing the yield of RNA from non-lesional skin sites on psoriatic patients or devising a method of calibrating $\Delta C_t$'s from lesions without using non-lesional controls. These strategies are:

1. Optimization of tape usage: It is probable that different techniques of applying tape to the skin could affect the recovery of RNA. In particular, aggressive application to the skin is necessary. Two physicians have been trained in the method. The consensus was that the training was highly instructive and will make a difference in how efficiently non-lesional skin is sampled.
2. In principle, only one non-lesional (i.e. unaffected) control is needed, since that data could be used to calibrate lesional samples taken at later time points. Thus a non-lesional sample could involve the one time use of up to 10 applications of tape to a single site to insure obtaining a sample.
3. There is anecdotal evidence that body location is a significant factor for RNA recovery. This hypothesis is being tested in healthy individuals. Preliminary data suggests that the upper arm, over the deltoid, the upper back over the scapular spine and the periauricular (mastoid) region may be superior RNA yielding sites.
4. A single shave biopsy could act as a control for all subsequent analysis.
5. It is possible, perhaps desirable to use commercially available RNA as a "universal" calibrator.

It is relatively common in medical diagnostics to analyze tissue samples and draw conclusions—without reference to a control sample—based on population data. For instance, blood is routinely analyzed and conclusions based on whether the value of a given parameter falls within a normal or abnormal range. In this example there is no "control" sample, the patient only has one blood source; the control is based on the range of values found in normal samples. Likewise, we should be able to evaluate psoriatic plaques without reference to a control sample from that individual. While the most obvious candidate for a diagnostic parameter is the $mRNA_x$/reference mRNA ratio, we have seen that without absolute quantification of mRNA, we cannot use $C_t$ values to calculate the absolute ratio of 2 mRNAs. This does not mean that we cannot use uncalibrated $\Delta C_t$'s to compare and classify lesions.

When the $\Delta\Delta C_t$ method is used to semi-quantitate mRNA a calibrator sample is required that allows the cancellation of unknown constants and consequent direct relation of $\Delta\Delta C_t$ to relative $mRNA_x/mRNA_a$ levels in the unknown and calibrator samples (formula 6; Materials and Methods Section). If one were to compare $\Delta C_t$ values amongst samples (i.e. an uncalibrated sample comparison), it would be necessary to account for the variables other than $X_0/A_0$ that contribute to the observed $\Delta C_t$.

Equation 4 relates the $\Delta C_t$ value to the $mRNA_x/mRNA_a$ ratio in the sample. Rearrangement of equation 4 (Materials and Methods) shows that $\Delta C_t$ is a function of 1] the $mRNA_x/mRNA_a$ ratio in the sample; 2] the $\Delta R_n$, values for the message of interest and normalization mRNA; and 3] the spectroscopic constant $K_{AX}$. If the samples to be compared are assayed during the same experiment, then the $\Delta R_n$ values will be identical and will not contribute to any differences in $\Delta C_t$. The use of the same sample volumes, and probes will likewise assure that $K_{AX}$ is the same for all samples. Therefore, it should be possible to compare uncalibrated $\Delta C_t$ values—knowing that they are only a function of $X_0/A_0$—and evaluate the hypothesis that the $mRNA_x/mRNA_a$ ratio is different in psoriatic versus non-psoriatic skin and that this difference extends across individuals in a population.

The data in Table 4 can be used to test this hypothesis. Table 4 contains the $\Delta C_t$ values for all samples. Under each mRNA-of-interest, the $\Delta C_t$ values for lesions are sorted into one of three columns. The first column on the left (signified by ↑) contains AC, values from lesion samples with significant increases in the $mRNA_x/mRNA_a$ ratio compared to control skin (Table 3). The second column contains $\Delta C_t$ values from lesions with no significant change from control skin. The third column contains $\Delta C_t$ values from unclassified lesions. The typical reason for a lesion being unclassified is due to insufficient RNA collection from the control sample (non-lesional skin). A fourth column contains $\Delta C_t$ values from non-lesional skin.

By sorting $\Delta C_t$ values into known and unknown categories, we can use statistical tests to determine if the categories define unique ranges. In Table 4 the average $\Delta C_{t,TNF}$ in samples with increased TNFα mRNA levels is 5.18. In contrast, the average $\Delta C_{t,TNF}$ for control skin samples is 9.53. A t-test shows that the difference between $\Delta C_t$ values for lesional vs. non-lesional skin is highly significant (p=0.0007). A similar analysis done on the unclassified $\Delta C_{t,TNF}$ data show that the unclassified lesion samples have $\Delta C_{t,TNF}$ values significantly different than control values (Table 4; p<0.0005). Thus it appears that the unclassified lesion samples consist largely of samples with elevated TNFα/β-actin mRNA ratios.

The same analysis can be applied to the $\Delta C_{t,CD2}$ data. Table 4 shows that the $\Delta C_{t,CD2}$ values for samples with elevated CD2 mRNA is significantly different than control samples (p=0.001) and that $\Delta C_{t,CD2}$ values for unclassified lesion samples are also different than control values (p<0.005). It therefore appears that our unclassified lesional samples represent mostly samples with increased CD2 mRNA levels.

Similar analysis of IFNγ mRNA reveals that $\Delta C_{t,IFN}$ in lesions with elevated IFNγ/actin mRNA ratios have significantly different $\Delta C_{t,IFN}$ values than control skin (Table 4; p=0.02). When the $\Delta C_{t,IFN}$ values for unclassified lesion samples are compared to control skin, there is not as high a confidence that they are different than non-lesional skin (p=0.12). Our interpretation of this data is that the unclassified category contains a mixture of samples, some of which have elevated IFNγ levels and some of which do not. Indeed, inspection of the unclassified $\Delta C_{t,IFN}$ values shows a range of values from a low of 2.01 (almost certainly abnormally high) to a high of 11.14 (probably normal). From this data we can conclude that most of the samples have elevated TNFα and CD2 mRNA levels and that some proportion of patients have elevated IFNγ mRNA levels. This suggests that we have 2 classes of patients, those with high levels of all 3 markers and those with high levels of TNF and CD2 and normal levels of IFNγ. It is of high interest to define the clinical differences that create these categories.

The above analysis of $\Delta C_t$ values establishes the likelihood that there is a range of values for lesional psoriatic skin and non-lesional skin unique to the skin type (Table 4). The heterogeneity in the unclassified $\Delta C_{t,IFN\gamma}$ data highlights the larger question of how to categorize lesional $\Delta C_t$ data for which we have no control samples. It is clear that in order to classify $\Delta C_t$'s we need a database of calibrated $\Delta C_t$ values from lesional and non-lesional (or normal skin from healthy individuals) skin. At our current rate of success obtaining RNA from non-lesional skin, we will need approximately 100 patients to get 25-30 calibrated $\Delta C_t$'s from which we can define normal and abnormal ranges. The fact that a subset of patients seems to be good RNA yielders raises an interesting question. If in fact these individuals have "different" normal skin then they may not be appropriate controls (for some markers, which by definition would be interesting). In fact, normal healthy people may be the best control group.

TABLE 1

Total RNA yield summary.

| | Skin Type and Yield* | | | |
| --- | --- | --- | --- | --- |
| | Non-lesional | | Lesional | |
| ID | Yield | Std dev | Yield | Std dev |
| 1 (W.S.)[1] | 5.1 | 1.2 | 44 | 8 |
| 2 (J.C.)[1] | 4.6 | 0.8 | 11 | 2.9 |
| 3 (J.S.)[1] | — | | 1.7 | 0.49 |
| 4 (D.C.)[1] | 29 | 9.1 | 18 | 1.8 |
| 5 (J.P.)[1] | 138 | 2.7 | 1.2 | 0.45 |
| 1[2] | 0.031 | 0.011 | 8.6 | 1.4 |
| 2[2] | 0.045 | 0.016 | 12.6 | 1.5 |
| 3[2] | 0.15 | 0.017 | 5.12 | 0.58 |
| 4[2] | 3.94 | 0.63 | 0.053 | 0.006 |
| 5[2] | 0.0063 | | 0.85 | 0.13 |
| 6[2,3] | ND | | ND | |

TABLE 1-continued

Total RNA yield summary.

| | Skin Type and Yield* | | | |
|---|---|---|---|---|
| | Non-lesional | | Lesional | |
| ID | Yield | Std dev | Yield | Std dev |
| 60 (70)[4] | 0.02 | 0.018 | 8.1 | 0.86 |
| 100 (105)[4] | 0.16 | 0.044 | 18 | 1.2 |
| 100 (110)[4] | 0.027 | 0.025 | | |
| 115 (120)[4] | 0.027 | 0.012 | 14 | 1.2 |
| 115 (125)[4] | 0.099 | 0.027 | | |
| 130 (135)[4] | 18 | 1.6 | 40 | 4.9 |
| 130 (140)[4] | 38 | 3.9 | | |
| 150 (160)[4] | 12 | 1.2 | 9.3 | 0.66 |
| 150 (170)[4] | 1.8 | 0.26 | | |
| 180 (190)[5] | 0.053 | 0.018 | 11.6 | 0.7 |
| 180 (200)[5] | ND | | | |
| 210 (220)[5] | ND | | 2.32 | 0.06 |
| 210 (230)[5] | ND | | | |
| 250 (260)[5] | ND | | 0.31 | 0.04 |
| 250 (260)[5] | ND | | | |
| 270 (280)[5] | 0.017 | 0.024 | 1.37 | 0.08 |
| 270 (290)[5] | ND | | | |
| 300 (310)[5] | 0.02 | 0.015 | 1.4 | 0.12 |
| 300 (320)[5] | ND | | | |
| 340 (350)[5] | 0.022 | 0.021 | 5.92 | 0.64 |
| 340 (360)[5] | 0.09 | 0.029 | | |
| 370 (380)[5] | 24.5 | 1.3 | 15.3 | 2.82 |
| 370 (390)[5] | 7.33 | 0.44 | | |
| 400[5,6] | 0.027 | 0.024 | | |
| 410[5,6] | ND | | | |
| 420[5,6] | 0.1 | 0.059 | | |

*Yield reported in nanograms total RNA;
ND = none detected
[1]University of Utah Round 1
[2]University of Utah Round 2
[3]Subject consented to one tape application
[4]University of Utah Round 3; one patient had a single control (sample ID 70) and lesion (ID 60) sampled, the remaining 4 patients had 2 controls and 1 lesion sampled; the control ID is in parenthesis
[5]University of Utah Round 4; 2 controls and 1 lesion sampled; control ID is in parenthesis
[6]These samples have not been assigned sample/lesion designations and may have been transported on ice an undefined amount of time before freezing

TABLE 2

Summary of mass recovery in sample sets 1-4.

| Lesional[1] | Control[1] | Patient Total |
|---|---|---|
| 21/23 (91%) | 11/35 (31%) | 24 |

[1]The fraction of samples with ≧200 picograms RNA; from a total of 23 patients, subject 6 from Round 2 is not included in these data (but is included in the patient total).

TABLE 3

Relative levels of TNFα, IFNγ and CD2 in psoriatic lesions.

| | Relative mRNA/ β-actin mRNA levels[1] | | |
|---|---|---|---|
| Sample# | TNFα | IFNγ | CD2 |
| 1[2] | (3.23) | (0.06) | (0.83) |
| 2[2] | 10** | ND | (1.9) |
| 3[2] | — | — | — |
| 4[2] | 8.9** | ND | 3.9 |
| 5[2] | 42** | (513)** | 20** |
| 1[3] | — | — | — |
| 2[3] | — | — | — |
| 3[3] | — | — | — |
| 4[3] | — | — | — |
| 5[3] | — | — | — |
| 60[4] | — | — | — |
| 100[4] | — | — | — |
| 115[4] | — | — | — |
| 130[4] | 11.3** | (1.7) | 2.38** |
| | 8.3** | (4.3)** | 2.42 |
| 150[4] | (37)** | 558** | 19** |
| | | (11)** | (5.7)** |
| 180[5] | — | — | — |
| 210[5] | — | — | — |
| 250[5] | — | — | — |
| 270[5] | — | — | — |
| 300[5] | — | — | — |
| 340[5] | — | — | — |
| 370[5] | 331** | 38** | 11.1** |
| 400[5,6] | — | — | — |

[1]The fold-induction relative to uninvolved skin is shown; Numbers in parentheses are lower limit estimates calculated by assigning a $C_t = 37$ to the mRNA of interest (TNFα, IFNγ or CD2), this estimate is used because the mRNA of interest was not detectable in the control site; values with ** are considered statistically different than the control site at the 95% confidence interval as described in Materials and Methods; a "—" indicates that insufficient RNA was recovered from the control (typical) or lesional site; ND indicates no mRNA for gene of interest detected in either lesion or control sample (but RNA present); Samples 130 and 150 have 2 different fold-increases corresponding to calibration to two different non-lesional skin sites.
[2]University of Utah Round 1
[3]University of Utah Round 2
[4]University of Utah Round 3; 1 patient had a single control and lesion sampled, the remaining 4 had 2 controls and 1 lesion sampled; the control ID is in parenthesis
[5]University of Utah Round 4; 2 controls and 1 lesion sampled; control ID is in parenthesis
[6]These samples have not been assigned sample/lesion ID and were transported on ice an undefined amount of time before freezing

TABLE 4

Categorization and comparison of ΔC, values.

| | $\Delta Ct \ (C_{t,gene} - C_{t,actin})$[1] | | | | | | | | | |
|---|---|---|---|---|---|---|---|---|---|---|
| | TNFα | | | | IFNγ | | | | CD2 | |
| | Psoriatic | | | | Psoriatic | | | | Psoriatic | |
| ID | ↑ | ↔ | UK | Control | ↑ | ↔ | UK | Control | ↑ | ↔ | UK | Control |
| 1 (W.S.)[2] | | | 6.45 | (8.14) | | | 11.16 | 7.12 | | | 8.17 | (7.89) |
| 2 (J.C.)[2] | 5.28 | | | 8.59 | | | (8.21) | (7.6) | | | 6.91 | (7.84) |
| 3 (J.S.)[2] | | | 5.04 | NRNA | | | 4.25 | NRNA | | | 4.64 | NRNA |
| 4 (D.C.)[2] | 7.84 | | | 10.99 | | | (8.32) | (9.43) | | 7.59 | | 9.54 |
| 5 (J.P.)[2] | 4.41 | | | 9.81 | 2.96 | | (11.96) | | 4.47 | | | 8.81 |
| 1[3] | | | 4.1 | NRNA | | | (8.19) | NRNA | | | 7.8 | NRNA |
| 2[3] | | | 2.84 | NRNA | | | 9.19 | NRNA | | | 5.25 | NRNA |
| 3[3] | | | 4.02 | NRNA | | | 7.96 | NRNA | | | 5.58 | NRNA |
| 4[3] | | | NRNA | 6.79 | | | NRNA | 9.91 | | | NRNA | 6.84 |
| 5[3] | | | 3.07 | NRNA | | | (8.24) | NRNA | | | (5.33) | NRNA |

TABLE 4-continued

Categorization and comparison of $\Delta C_t$ values.

$\Delta Ct\ (C_{t,gene} - C_{t,actin})$[1]

| | TNFα | | | | IFNγ | | | | CD2 | | | |
|---|---|---|---|---|---|---|---|---|---|---|---|---|
| | Psoriatic | | | | Psoriatic | | | | Psoriatic | | | |
| ID | ↑ | ↔ | UK | Control | ↑ | ↔ | UK | Control | ↑ | ↔ | UK | Control |
| 60 (70)[4] | | | 8.29 | NRNA | | | 9.98 | NRNA | | | 7.72 | NRNA |
| 100 (105)[4] | | | 6.22 | NRNA | | | 10.09 | NRNA | | | 7.06 | NRNA |
| 100 (110)[4] | | | | NRNA | | | | NRNA | | | | NRNA |
| 115 (120)[4] | | | 5.07 | NRNA | | | 11.14 | NRNA | | | 8.5 | NRNA |
| 115 (125)[4] | | | | NRNA | | | | NRNA | | | | NRNA |
| 130 (135)[4] | 7.11 | | 10.6 | | | | 10.2 | (10.96) | | 8.67 | | 9.92 |
| 130 (140)[4] | | | 10.16 | | | | (12.3) | | | | | 9.94 |
| 150 (160)[4] | 5.13 | | | (10.35) | 3.49 | | | 12.62 | 4.48 | | | 8.72 |
| 150 (170)[4] | | | | (6.99) | | | | (6.99) | | | | (6.99) |
| 180 (190)[5] | | | 4.03 | NRNA | | | 4.68 | NRNA | | | 4.23 | NRNA |
| 180 (200)[5] | | | | NRNA | | | | NRNA | | | | NRNA |
| 210 (220)[5] | | | 6.86 | NRNA | | | (8.18) | NRNA | | | 7.8 | NRNA |
| 210 (230)[5] | | | | NRNA | | | | NRNA | | | | NRNA |
| 250 (240)[5] | | | 3.91 | NRNA | | | (4.98) | NRNA | | | (4.98) | NRNA |
| 250 (260)[5] | | | | NRNA | | | | NRNA | | | | NRNA |
| 270 (280)[5] | | | 3.7 | NRNA | | | 3.47 | NRNA | | | 5.54 | NRNA |
| 270 (290)[5] | | | | NRNA | | | | NRNA | | | | NRNA |
| 300 (310)[5] | | | 3.23 | NRNA | | | 2.01 | NRNA | | | 4.84 | NRNA |
| 300 (320)[5] | | | | NRNA | | | | NRNA | | | | NRNA |
| 340 (350)[5] | | | 2.65 | NRNA | | | 4.6 | NRNA | | | 5.51 | NRNA |
| 340 (360)[5] | | | | NRNA | | | | NRNA | | | | NRNA |
| 370 (380)[5] | 1.28 | | | 9.66 | 6.67 | | | 11.93 | 6.63 | | | 10.09 |
| 370 (390)[5] | | | | 9.64 | | | | (10.13) | | | | (10.13) |
| 400[5,6] | | | | NRNA | | | | NRNA | | | | NRNA |
| 410[5,6] | | | | NRNA | | | | NRNA | | | | NRNA |
| 420[5,6] | | | | NRNA | | | | NRNA | | | | NRNA |
| Average* | 5.18 | | 4.63 | 9.53 | 4.37 | | 7.39 | 10.40 | 5.19 | 8.13 | 6.4 | 9.12 |
| p-value† | 0.0007 | | <0.0005 | | 0.02 | | 0.12 | | 0.001 | 0.3 | <0.005 | |

[1] The $\Delta C_t$ value is defined as the $C_t$ value for the mRNA of interest minus the $C_t$ value for β-actin ($C_{t,mRNA} - C_{t,actin}$). In some samples the mRNA of interest cannot be detected, in which case the $C_t$ is defined as 37 cycles, our limit of detection; in such cases an estimated $\Delta C_t$ is calculated from the formula $37 - C_{t,actin}$ and is reported in parenthesis. A column headed by a ↑ contains data from lesions with statistically elevated (95% confidence interval) cytokine levels; a column headed with ↔ contains data from lesions showing no significant change; a column headed by UK contains unclassified data (calibrator unavailable); NRNA indicates insufficient RNA recovered.
[2] University of Utah Round 1.
[3] University of Utah Round 2.
[4] University of Utah Round 3; 1 patient had a single control and lesion sampled, the remaining 4 had 2 controls and 1 lesion sampled; the control ID is in parenthesis.
[5] University of Utah Round 4; 2 controls and 1 lesion sampled; control ID is in parenthesis.
[6] These samples have not been assigned sample/lesion ID and may have been transported on ice an undefined amount of time before freezing.
*Averages and standard deviations do not include estimated data (# in parentheses).
†Two tailed t-test compared to non-lesional skin; $\Delta C_t$ values in parentheses are not included in the calculation.

EXAMPLE 4

Relative levels of mRNA as indicated by $\Delta C_t$ values in lesional and non-lesional skin of psoriatic patients This example illustrates the use of the tape stripping method disclosed herein and $\Delta C_t$ values, to characterize genomic expression in the stratum corneum of psoriasis lesional and non-lesional skin. More specifically, this study determines if $\Delta C_t$ values for various mRNAs known to be upregulated in psoriatic lesions could be characterized using RNA recovered by tape stripping.

Methods

The tape stripping procedure and tape are identical to those disclosed in Example 3. One lesion was sampled and 3 independent uninvolved skin (UIS) sites were sampled per patient. The 3 uninvolved skin site samples were combined to produce one "global" control sample. Each site was sampled with 4 individual tapes, each sequentially applied and removed once. mRNA was semi-quantitated using the comparative or $\Delta C_t$ method using β-actin as the normalizing message.

Results and Discussion

In this tape stripping study a total of 72 subjects lesions and 163 normal skin sites were sampled. Some patients with less severe disease were only sampled on uninvolved skin sites. Each sample was semi-quantitated for GAPDH, TNFα, IFNγ, CD2, Krt-16, IL-12B, and IL-23A mRNA which were normalized to β-actin mRNA. The results of these assays are shown in Table 9.

TABLE 9

Population average ΔC, values of select biomarker mRNAs in lesional and uninvolved skin of psoriatic patients

| | Biomarker mRNA and Average $\Delta C_t$[b] | | | | | | | | | | | | | |
|---|---|---|---|---|---|---|---|---|---|---|---|---|---|---|
| | GAPDH | | TNFα | | IFNγ | | Krt-16 | | CD2 | | IL-12B | | IL-23A | |
| Site[a] | $\Delta C_t$ | SEM | $\Delta C_t$ | SEM | $\Delta C_t$ | SEM | $\Delta C_t$ | SEM | $\Delta C_t$ | SEM | $\Delta C_t$ | SEM | $\Delta C_t$ | SEM |
| UIS (N) | 2.07 (163) | 0.06 | 8.32 (97) | 0.16 | 10.5 (9) | 0.72 | −1.33 (137) | 0.12 | 8.43 (34) | 0.3 | 11.5 (3) | 1.8 | 9.03 (10) | 0.63 |
| Lesion (N) | 0.72 (72) | 0.19 | 4.87 (72) | 0.21 | 7.79 (66) | 0.35 | −2.57 (45) | 0.23 | 6.56 (69) | 0.18 | 8.55 (44) | 0.28 | 5.7 (45) | 0.31 |

[a]Tape stripped site, lesional or uninvolved skin (UIS); the number of observations is listed below in parenthesis.
[b]$\Delta C_t$ is defined as $C_{t,mRNAx} - C_{t,actin\ mRNA}$ where $C_t$ is the respective number of PCR cycles required to achieve threshold fluorescence. In some samples the threshold could not be determined (i.e. the mRNA was not detectable) or was not assayed, thus the number of observations is different for each mRNA. SEM is standard error of the mean calculated as standard deviation divided by $N^{1/2}$.

The data in Table 9 clearly demonstrates that there are different relative levels of all the mRNAs listed in lesional and control skin. For TNFα, IFNγ, CD2, IL-12B, Krt-16 and IL-23A the $\Delta C_t$ values all indicate a relative increase in mRNA expression in lesional skin, in agreement with published data. Thus we conclude that RNA recovered from tape stripped skin can accurately reflect the molecular events known to be active in lesional psoriatic skin compared to uninvolved skin.

EXAMPLE 5

A comparison of $\Delta C_t$ values in psoriatic lesions with clinical assessment (NPF Score) over time and treatment This Example illustrates that tape harvested RNA and $-C_t$ values can be used to monitor changes in psoriasis.

Methods

Patients were treated with Enbrel™ (Etanercept) over a period of months. Both before treatment commenced (week 0) and at various time points during treatment, a lesion was tape stripped using the synthetic rubber-based adhesive MA70 (Adhesives Research) on a polyurethane film. Adhesive strips were manufactured as circles of 17 mm diameter. Skin sites were sequentially stripped with 4 individual tapes, with each tape applied and removed once. The RNA isolated from the adherent cells on all 4 tapes (from one site) was pooled into one sample. Total RNA recovered from tapes was semi-quantified for the mRNAs listed in Table 1. Quantitation was by quantitative RT-PCR using the comparative method with β-actin mRNA as the internal normalizing mRNA standard and calibration achieved by using population average values for $\Delta C_t$ in uninvolved skin of psoriatic subjects (Table 1).

Results and Discussion

Table 10 shows the results of assaying GAPDH, TNFα, IFNγ, IL-12B and IL-23A mRNAs relative to β-actin mRNA as well as the clinical assessment of disease as characterized by NPF Score, both before and after 8 weeks of treatment. Rather than calibrate the lesion samples to uninvolved skin of each patient, we have chosen to calibrate to population average values to gain a fold-change relative to non-psoriatic skin. The results of calibrating to each patient's uninvolved skin values were virtually identical (data not shown). Table 10 also shows that the change from baseline to week 8 for almost all $\Delta C_t$ values in lesion samples was positive, while the change in NPF score was negative (indicating improvement in disease) over this same time period. Thus, positive changes in $\Delta C_t$ values of these specific mRNAs are negatively correlated with the change from baseline at week 8 in NPF scores. This negative correlation suggests that decreases in levels of TNFα, IFNγ, IL-12B and IL-23A mRNAs correlate with improvement in clinical symptoms. This is most clearly demonstrated by inspecting the fold-change data in Table 10. In order to assess the significance this observation, the AC, and NPF data in Table 10 was analyzed. The results of this analysis are shown in Table 11.

TABLE 10

$\Delta C_t$ values, fold change and NPF score before treatment and at week 8 of treatment in psoriatic lesions of 6 patients

| | | $\Delta C_t$ (Lesion)[a] Week | | Fold Change (Pop-UIS)[b] Week | | NPF Score[c] Week | |
|---|---|---|---|---|---|---|---|
| mRNA | Patient # | 0 | 8 | 0 | 8 | 0 | 8 |
| GAPDH | P2 | −3.11 | 1.02 | 36.25 | 2.07 | 22 | 12 |
| | P3 | −2.83 | 1.04 | 29.86 | 2.04 | 14.7 | 10.7 |
| | P4 | −0.38 | 1.31 | 5.46 | 1.69 | 10.7 | 10.3 |
| | P5 | −2.58 | 1.4 | 25.11 | 1.59 | 24.7 | 16.7 |
| | P6 | 0.95 | 1.58 | 2.17 | 1.40 | 20 | 18.7 |
| | P7 | 0.84 | 1.25 | 2.35 | 1.77 | 18.3 | 11.7 |
| TNFα | P2 | 0.52 | 4.99 | 222.86 | 10.06 | 22 | 12 |
| | P3 | 1.41 | 4.27 | 120.26 | 16.56 | 14.7 | 10.7 |
| | P4 | 4.86 | 5.82 | 11.00 | 5.66 | 10.7 | 10.3 |
| | P5 | 1.05 | 5.15 | 154.34 | 9.00 | 24.7 | 16.7 |
| | P6 | 6.58 | 4.8 | 3.34 | 11.47 | 20 | 18.7 |
| | P7 | 3.9 | 4.21 | 21.41 | 17.27 | 18.3 | 11.7 |
| INFγ | P2 | 4.19 | 11.27 | 79.34 | 0.59 | 22 | 12 |
| | P3 | 0.95 | 4.91 | 749.61 | 48.17 | 14.7 | 10.7 |
| | P4 | 9.09 | 9.92 | 2.66 | 1.49 | 10.7 | 10.3 |
| | P5 | 2.53 | 7.47 | 250.73 | 8.17 | 24.7 | 16.7 |
| | P6 | 10.83 | 9.13 | 0.80 | 2.58 | 20 | 18.7 |
| | P7 | 7.03 | 8.8 | 11.08 | 3.25 | 18.3 | 11.7 |
| IL-12B | P2 | 7.19 | 12.48 | 19.84 | 0.51 | 22 | 12 |
| | P3 | 4.65 | 7.35 | 79.34 | 9.45 | 14.7 | 10.7 |
| | P4 | >9.3 | 9.09 | 4.59 | 5.31 | 10.7 | 10.3 |
| | P5 | 6.24 | >8.01 | 38.32 | 11.24 | 24.7 | 16.7 |
| | P6 | 11.26 | 6.7 | 1.18 | 27.86 | 20 | 18.7 |
| | P7 | 4.23 | 4.78 | 154.34 | 105.42 | 18.3 | 11.7 |
| IL-23A | P2 | 2.81 | 6.59 | 74.54 | 5.43 | 22 | 12 |
| | P3 | 0.77 | 4.85 | 212.31 | 24.25 | 14.7 | 10.7 |
| | P4 | 8.24 | 6.52 | 1.73 | 5.70 | 10.7 | 10.3 |
| | P5 | 2.69 | 5.71 | 81.01 | 9.99 | 24.7 | 16.7 |
| | P6 | 5.17 | 4.94 | 14.52 | 17.03 | 20 | 18.7 |
| | P7 | 4.32 | 4.81 | 26.17 | 18.64 | 18.3 | 11.7 |

[a]$\Delta C_t$ for a sample is calculated as the $C_{t,mRNAx} - C_{t,mRNA\ actin}$ where $C_{t,mRNAx}$ is the number of PCR cycles required to achieve threshold fluorescence for gene "X" and $C_{t,mRNA\ actin}$ is the analogous value for β-actin. Threshold values for the mRNA of interest and β-actin for a given sample were assayed simultaneously (i.e. during the same experiment).
[b]The fold-change of the mRNA/β-actin mRNA ratio relative to the population average value $\Delta C_t$ for uninvolved skin. The fold-change is calculated as $2^{-(\Delta\Delta C_t)}$ where $\Delta\Delta C_t$ (comparative method) is equal to $\Delta C_{t,lesion} - \Delta C_{t,population\ ave}$.
[c]National Psoriasis Foundation (NPF) Score at week 0 and week 8.

The data in Table 11 shows the correlation coefficient and p-value for a one sided t-test as well as the exact p-value for a permutation test for a comparison of change in NPF score and $\Delta C_t$ value between week 0 and week 8 of treatment. The data show a significant correlation between $\Delta C_t$ values for TNFα, IFNγ, IL-12B and NPF Score, with the negative correlation confirming that an improvement (decrease) in NPF Score corresponds with a decrease (increase in $\Delta C_t$) in mRNA levels. The table also shows that the correlation for IL-23B nears significance while the correlation of the housekeeping gene GAPDH is not significant. We suspect that with higher numbers of patients in the study the data would be even more significant. Similar data for CD2 and Krt-16 was not significant but trended towards significance (data not shown). We conclude that RNA recovered by the non-invasive tape stripping of psoriatic lesions can accurately portray clinical improvement. This data suggests that if molecular profiles exist that precede clinical improvement (i.e. predict outcome), that RNA recovered by tape stripping can reveal these profiles.

TABLE 11

Summary of correlation coefficients between change from week 0 and week 8 in NPF Score and $\Delta C_t$ value for various mRNAs in psoriatic lesions

| mRNA in lesion | Observations | Correlation Coefficient: R | $T_{(N-2)}$[a] | One sided t test | Exact P value: Permutation Test[b] |
|---|---|---|---|---|---|
| GAPDH | 6 | −0.56 | −1.35 | P > 0.10 | 0.097 |
| TNFα | 6 | −0.74 | −2.18 | 0.025 < P < 0.05 | 0.047 |
| IFNγ | 6 | −0.85 | −3.23 | 0.01 < P < 0.025 | 0.018 |
| IL-12B | 6 | −0.76 | −2.32 | 0.025 < P < 0.05 | 0.044 |
| IL23-A | 6 | −0.73 | −2.14 | 0.025 < P < 0.05 | 0.057 |

[a] A t-statistic with 4 degrees of freedom has been calculated to test the significance of the observed correlation coefficient using the formula; $T_{(N-2)} = R * (N-2)^{0.5}/(1-R^2)^{0.5}$
[b] Since the number of observations used in the calculation of the correlation coefficient is only 6, calculation of T statistic, based on asymptotic normality may not be appropriate. Therefore we have used permutation test and exact probabilities of observing a correlation coefficient <= observed value have been calculated using bootstrap sampling. The software used for calculatingthese p values was "RESAMPLING STATS" in EXCEL.

The uninvolved skin data in Table 9 can be used to classify the lesional skin of patients in Table 2 by $\Delta C_t$ value. That is, the $\Delta C_t$ value for different mRNAs in a lesion at time 0 can be classified as "normal" or "abnormal" by comparison with the population average $\Delta C_t$'s for uninvolved skin. We have chosen as normal any value that falls within 3 SEMs of the average $\Delta C_t$ for uninvolved skin using the data in Table 9. The result of classifying lesions before treatment is shown in Table 12.

TABLE 12

Characterization of psoriatic lesions by comparison to population average values for uninvolved skin.

| Patient # | Molecular Phenotype of Lesion Before Treatment[a] | | | | | | |
|---|---|---|---|---|---|---|---|
|  | GAPDH | TNFα | IFNγ | IL-12B | IL-23A | Krt-16 | CD2 |
| 2 | − | − | − | + | − | − | − |
| 3 | − | − | − | − | − | − | − |
| 4 | − | − | + | + | + | − | − |
| 5 | − | − | − | + | − | − | − |
| 6 | − | − | + | + | − | + | + |
| 7 | − | − | − | − | − | − | − |

[a] classification of normal is indicated by "+", while abnormal is indicated by "−". The designation of normal is given if the lesion $\Delta C_t$ value (Table 10) approaches within 3 standard errors of the mean (SEM) of the population average value for uninvolved skin (Table 1). This criteria means that to be classified as normal, the $\Delta C_t$ values in the lesion must be greater than or equal to: 1.89 (GAPDH); 7.84 (TNFα); 8.34 (IFNγ); 6.1 (IL-12B); 7.14 (IL-23A); −1.69 (Krt-16); 7.53 (CD2). $\Delta C_t$ data is taken from Tables 1 and 3 with the exception of Krt-16 and CD2 patient data, which is not shown.

Table 12 shows that even this limited set of patients with similar clinical disease can be categorized into several subgroups depending on the normal/abnormal profile of mRNA in the lesion. The most striking categories are patients 3 and 7 who have high levels of all mRNA in lesional skin and patients 4 and 6 who have normal levels of IFN and IL-12B in the lesion. The observation of very low IFNγ mRNA is surprising given the current dogma that IFNγ protein is elevated in all lesions. While the low mRNA level of IFNγ does not preclude high proteins levels, the fact that some lesions are low in IFNγ mRNA while others are high is surprising. While the significance of these differing lesional profiles has yet to be determined, we have confirmed that such profiling can be done using tape stripped mRNA. It is likely that with the addition of more patients in such studies and the use of DNA arrays to analyze RNA, significant multi-gene profiles will emerge that will be clinically useful.

EXAMPLE 6

An Analysis of Keratin Gene Expression in SLS-Irritated and Control Skin

This Example provides expression data of keratin 10, 16 and 17 in samples of SLS-irritated and control skin as recovered by tape harvesting and biopsy. The keratins are a family of cytoskeletal proteins found prominently in keratinocytes. The basal layer of the epidermis expresses Krt-5 and Krt-14, while the differentiating suprabasal layer expresses Krt-1 and Krt-10. When keratinocytes become inflammatory they are activated and express Krt-6, 16 and 17, while down-regulating transcription of Krt-10 (Komine, Freedberg et al. 1996; Freedberg, Tomic-Canic et al. 2001). Thus skin that has become inflamed by SLS would be predicted to express K16 and K17 and repress transcription of K10. In a continuing effort to define the ability of tape strip recovered RNA to reliably reveal quantitative changes in gene expression the expression of genes known to be induced by inflammation in tape stripped and biopsy samples of inflamed and control skin, were compared.

The samples analyzed in this study are those described in the protocol performed by Wong et al. (Wong, Tran et al. 2004). Briefly, 10 subjects were occlusively patched (2 duplicate patches) with 1% SLS (aqueous) and water on the midback for 24 hours. Patches were removed and equivalent skin sites were biopsied and tape stripped as described in the Examples above. As an additional control, normal skin was also biopsied and tape stripped. Samples were processed for total RNA and assayed for keratin-10, keratin-16, keratin-17 and β-actin mRNA. The keratin mRNAs were normalized to β-actin mRNA in each sample. The semi-quantitative RT-PCR assay has been previously described (Wong, Tran et al. 2004).

Tables 13, 14 and 15 show the $\Delta C_t$ for Krt-10, Krt-16, and Krt-17 mRNA relative to β-actin mRNA. In addition, the tables also show the calculated fold-change of the mRNA/actin ratio in SLS and water treated skin relative to untreated skin. The tape and biopsy data for average K10 expression is virtually identical and reveals an approximate 20-fold average decrease in expression with SLS treatment, while water treatment has little effect (Table 13). Thus, for K10 expression, tape and biopsy data agree.

Table 14 shows biopsy data and tape data for K16 expression in SLS and water treated skin. As expected, K16 mRNA expression is increased in biopsy samples of SLS-treated skin. The table reveals an average 39-fold-increase with SLS treatment. Surprisingly, tape samples reveal an average 9-fold decrease in K16 expression in SLS treated samples. In order to confirm this difference between biopsy and tape data, we assayed the expression of K17, which is known to be induced with K16 during inflammation.

Table 15 shows the K17 data for tape and biopsy samples of SLS and water treated samples. The average fold-increase of K17 in biopsy samples of SLS-treated skin is 42-fold, virtually identical to the K16 data. Again, in contrast to biopsy samples, tape samples revealed the K17/actin mRNA ratio being 8-fold decreased in tape harvested samples of SLS-treated skin. Thus K16 and K17/actin mRNA ratios are consistently elevated in biopsy samples, as predicted, and decreased in tape harvested samples. This leads to the surprising conclusion that when irritated skin is sampled with tape, a decrease in K16 or K17 expression is diagnostic of inflammation.

The significance of the $\Delta C_t$ data in Tables 13, 14, and 15 was tested by a 2-way full, repeated measures ANOVA. The results showed significant overall effects for all the keratins (p<0.0001). Table 16 reveals some of the significant pair-wise comparisons. Table 16 reveals that not only are the fold-changes due to SLS-treatment highly significantly different, as expected, but that the $\Delta C_t$ values are also highly significantly different between tape and biopsy methods. This difference in $\Delta C_t$ values within a treatment and the fact that tape shows a decrease in Krt-16 and Krt-17 expression while biopsy shows an increase confirms previous data suggesting that tape harvesting and biopsy recover distinctly different cell populations.

Literature Cited in this Example

Freedberg, I. M., M. Tomic-Canic, et al. (2001). "Keratins and the keratinocyte activation cycle." *J Invest Dermatol* 116(5): 633-40.

Komine, M., I. M. Freedberg, et al. (1996). "Regulation of epidermal expression of keratin K17 in inflammatory skin diseases." *J Invest Dermatol* 107(4): 569-75.

Wong, R., V. Tran, et al. (2004). "The use of RT-PCR and DNA microarrays to characterize RNA recovered by non-invasive tape-harvesting of normal and inflamed skin." *Journal of Investigative Dermatology* In Press.

TABLE 13

Changes in $\Delta C_{t,\, Krt\text{-}10}$ in SLS treated, water-treated and untreated skin and resulting fold-change in Krt-10/β-actin mRNA ratio relative to untreated skin in RNA samples recovered by tape stripping and biopsy.

| | $\Delta C_{t, Krt\text{-}10}$[a] | | | | | | Fold Increase Krt-10/β-actin mRNA vs. normal[b] | | | |
|---|---|---|---|---|---|---|---|---|---|---|
| | Tape | | | Biopsy | | | Tape | | Biopsy | |
| ID | Normal Skin | Water | SLS | Normal Skin | Water | SLS | Water | SLS | Water | SLS |
| 1 | -2.13 | -1.41 | -2.76 | -6.99 | -7.06 | -4.28 | 0.61 | 1.55 | 1.05 | 0.15 |
| 2 | -1.45 | -1.01 | 3.68 | -7.22 | -6.69 | -0.24 | 0.74 | 0.03 | 0.69 | 0.01 |
| 3 | -2.28 | -3.09 | 8.19 | -7.10 | -7.26 | -3.09 | 1.74 | <0.001 | 1.11 | 0.06 |
| 4 | — | — | -0.3 | -6.98 | -7.31 | -6.35 | — | — | 1.26 | 0.65 |
| 5 | — | -1.56 | 0.93 | -7.38 | -7.23 | -4 | — | — | 0.9 | 0.1 |
| 6 | -2.08 | 0.97 | 5.1 | -6.47 | -6.45 | 0.4 | 0.12 | 0.01 | 0.99 | 0.01 |
| 7 | -0.67 | -0.87 | 1.03 | -7.01 | -7.17 | -2 | 1.15 | 0.31 | 1.12 | 0.03 |
| 8 | -2.29 | -1.92 | 4.17 | -6.65 | -6.17 | -2.7 | 0.77 | 0.01 | 0.72 | 0.06 |
| 9 | -2.99 | 1.38 | 3.81 | -6.51 | -6.32 | 1.91 | 0.05 | 0.01 | 0.88 | <0.001 |
| 10 | -0.53 | -4.09 | -0.81 | -6.8 | -6.03 | -5.97 | 11.91 | 1.22 | 0.59 | 0.57 |
| Average | -1.80 | -1.29 | 2.30 | -6.91 | -6.77 | -2.63 | 0.70 | 0.06 | 0.91 | 0.05 |

[a] $\Delta C_{t, Krt\text{-}10}$ is defined as $C_{t,Krt\text{-}10} - C_{t,actin}$ where $C_{t,Krt\text{-}10}$ is the number of PCR cycles required to reach threshold fluorescence for Krt-10 detection and $C_{t,actin}$ is the analogous number for β-actin detection in the same sample.
[b] Fold-increase is calculated as $2^{-(\Delta\Delta C_t)}$ where $\Delta\Delta C_t$ is equal to $\Delta C_{t,condition} - \Delta C_{t,normal}$; $\Delta C_{t,condition}$ is defined above where "condition" refers to either water or SLS treatment; $\Delta C_{t,normal}$ is the $\Delta C_t$ value in the normal (untreated skin) sample. Fold-increases were calculated using the data in the columns to the left. The method is described in detail in Wong et al (Wong, Tran et al. 2004).

TABLE 14

Changes in $\Delta C_{t,Krt\text{-}16}$ in SLS treated, water-treated and untreated skin and resulting fold-change in Krt-16/β-actin mRNA ratio relative to untreated skin in RNA samples recovered by tape stripping and biopsy.

| | $\Delta C_{t, Krt\text{-}16}$[a] | | | | | | Fold Increase Krt-16/actin mRNA ratio vs. normal[a] | | | |
|---|---|---|---|---|---|---|---|---|---|---|
| | Tape | | | Biopsy | | | Tape | | Biopsy | |
| ID | Normal Skin | Water | SLS | Normal Skin | Water | SLS | Water | SLS | Water | SLS |
| 1 | -4.18 | -3.55 | -4.51 | 4.85 | 5.33 | 0.97 | 0.64 | 1.25 | 0.72 | 14.73 |
| 2 | -0.15 | 0.75 | 3.04 | 3.83 | 3.98 | -2.43 | 0.54 | 0.11 | 0.90 | 76.61 |
| 3 | -1.05 | -2.42 | 3.96 | 3.57 | 3.14 | -2.21 | 2.59 | 0.03 | 1.35 | 55.14 |
| 4 | — | — | -2.87 | 5.61 | 3.62 | 1.41 | — | — | 3.97 | 18.4 |
| 5 | — | -3.11 | 0.53 | 3.83 | 5 | -1.12 | — | — | 0.44 | 30.85 |
| 6 | -3.57 | -0.09 | 3.1 | 5.08 | 3.08 | -1.75 | 0.09 | 0.01 | 4 | 113.69 |
| 7 | -1.8 | -1.29 | 0.53 | 4.76 | 4.81 | -2.01 | 0.7 | 0.2 | 0.96 | 108.78 |
| 8 | -1.48 | -1.01 | 4.32 | 4.59 | 0.88 | -1.79 | 0.72 | 0.02 | 13.04 | 82.98 |
| 9 | -1.8 | -2.13 | 2.87 | 3.84 | 3.88 | 0.74 | 1.26 | 0.04 | 0.97 | 8.57 |

TABLE 14-continued

Changes in $\Delta C_{t,Krt-16}$ in SLS treated, water-treated and untreated skin and resulting fold-change in Krt-16/β-actin mRNA ratio relative to untreated skin in RNA samples recovered by tape stripping and biopsy.

| | $\Delta C_{t,Krt-16}{}^a$ | | | | | | Fold Increase Krt-16/actin mRNA ratio vs. normal$^a$ | | | |
|---|---|---|---|---|---|---|---|---|---|---|
| | Tape | | | Biopsy | | | | | | |
| | Normal | | | Normal | | | Tape | | Biopsy | |
| ID | Skin | Water | SLS | Skin | Water | SLS | Water | SLS | Water | SLS |
| 10 | −3.54 | −1.69 | −0.97 | 4.31 | 3.74 | −0.32 | 0.28 | 0.17 | 1.48 | 24.78 |
| Average | −2.20 | −1.62 | 1.00 | 4.43 | 3.75 | −0.85 | 0.67 | 0.11 | 1.60 | 38.80 |

$^a$See footnotes to Table 13 for a description of calculations.

TABLE 15

Changes in $\Delta C_{t,Krt-17}$ in SLS treated, water-treated and untreated skin and resulting fold-change in Krt-17/β-actin mRNA ratio relative to untreated skin in RNA samples recovered by tape stripping and biopsy.

| | $\Delta C_{t,Krt-17}{}^a$ | | | | | | Fold Increase Krt-17/βactin mRNA ratio vs. normal$^a$ | | | |
|---|---|---|---|---|---|---|---|---|---|---|
| | Tape | | | Biopsy | | | | | | |
| | Normal | | | Normal | | | Tape | | Biopsy | |
| ID | Skin | Water | SLS | Skin | Water | SLS | Water | SLS | Water | SLS |
| 1 | −4.38 | −5.04 | −5.12 | 4.45 | 3.4 | 0.71 | 1.58 | 1.67 | 2.06 | 13.31 |
| 2 | −4.01 | −3.63 | 1.64 | 4.27 | 2.89 | −2.29 | 0.77 | 0.02 | 2.61 | 94.54 |
| 3 | −3.84 | −4.55 | 1.5 | 2.99 | 3.27 | −2.5 | 1.63 | 0.02 | 0.82 | 44.95 |
| 4 | — | — | −4.87 | 3.31 | 2.4 | 1.13 | — | — | 1.87 | 4.51 |
| 5 | — | −5.1 | −1.79 | 2.8 | 1.37 | −1.97 | — | — | 2.69 | 27.19 |
| 6 | −5.26 | −2.47 | 1.11 | 2.32 | 2.39 | −1.63 | 0.14 | 0.01 | 0.95 | 15.44 |
| 7 | −4.4 | −4.62 | −1.84 | 5.93 | 7.26 | −2.91 | 1.16 | 0.17 | 0.4 | 459.45 |
| 8 | −2.99 | −3.53 | 1.38 | 5.86 | 1.96 | −1.75 | 1.46 | 0.05 | 14.76 | 195.94 |
| 9 | −4.35 | −3.3 | 0.21 | 3.74 | 3.11 | −1.86 | 0.48 | 0.04 | 1.55 | 48.35 |
| 10 | −3.1 | −4.01 | −2.12 | 5.25 | 3.97 | −0.11 | 1.87 | 0.5 | 2.43 | 41.13 |
| Average | −4.04 | −4.03 | −0.99 | 4.09 | 3.20 | −1.32 | 0.99 | 0.12 | 1.85 | 42.52 | d. See footnotes to Table 13 for a description of calculations.

TABLE 16

Significant pair-wise comparisons of $\Delta C_t$ values between sampling method and treatment.

| | | p-value by treatment$^b$ | | |
|---|---|---|---|---|
| mRNA | Sampling method$^a$ | Untreated | Water-treated | SLS-treated |
| Krt-10 | Biopsy | — | 0.87 | <0.0001 |
| | Tape | — | 0.58 | <0.0001 |
| | Tape vs. biopsy | <0.0001 | <0.0001 | 0.0001 |
| Krt-16 | Biopsy | — | 0.37 | <0.0001 |
| | Tape | — | 0.68 | 0.0002 |
| | Tape vs. biopsy | <0.0001 | <0.0001 | 0.017 |
| Krt-17 | Biopsy | — | 0.21 | <0.0001 |
| | Tape | — | 0.8 | 0.0003 |
| | Tape vs. biopsy | <0.0001 | <0.0001 | 0.64 |

$^a$When a single method is shown, the comparison is between that sampling method on normal skin versus the same sampling method on water or SLS treated skin.
$^b$Resulting p-values from pair-wise comparison of a 2-way full measures ANOVA. $\Delta C_t$ values are compared within a sampling method for normal versus SLS or water treated skin (i.e. biopsy of SLS-treated skin vs. biopsy of normal skin) and between methods for a given treatment (i.e. biopsy vs. tape for SLS treated skin).

EXAMPLE 7

Differentiation of Irritant and Allergic Reactions by mRNA Profiling

This Example provides experiments to identify of RNA profiles that can differentiate irritant contact dermatitis (ICD) from allergic contact dermatitis (ACD). Current obstacles to differentiating irritant from allergic skin reactions are the clinical similarity of these different dermatitides. Molecular and histological analysis have shown that these reactions share many similar features but are known to have distinct identifying histologically features. To date there has been no demonstration of an RNA assay that can reliably differentiate between these two classes of dermatitides for broad classes of substances.

Method: A clinical trial is conducted with up to 20 subjects. Each subject is patched occlusively with Finn chambers containing different irritants and allergens. Irritants such as: Triton X100, sodium lauryl sulfate, 8% formaldehyde, Tween 80, benzalkonium chloride, benzoic acid, CTAB, resorcinol, or phenol are applied at concentrations known to produce irritant skin reactions for up to 24 hours with the appropriate vehicle, with vehicle controls. Allergens such as poison ivy (rhus), 1% formaldehyde, nickel sulphate, coumarin, neomycin, Balsam of Peru, Kathon CG, epoxy resin, Carbamix, methyldibromoglutaronitril, imidazolidinyl urea or sequiterpene lactone mix are used at the appropriate concentrations in the standard vehicles. After up to 24 hours of exposure, chambers are removed and skin reactions scored. The sites are then tape harvested with up to 4 tapes sequentially applied and removed, using skin harvesting tape (Product No. 90068)

(Adhesives Research, Glen Rock, Pa.). RNA is extracted from the tapes, amplified by the standard T7 linear method and amplified RNA hybridized to DNA arrays. From this data, distinct RNA differential expression profiles are identified; these profiles are confirmed in a second experiment.

A second protocol is performed to confirm that the profiles identified above can be used to reproducibly differentiate ACD from ICD. This second study is similar in design to the first, with the exception that at least one half the subjects will be different than the first study.

A core group of differentially regulated RNAs are expected to be identified that are unique, or expressed at different levels, in an irritant skin reaction compared to an allergic skin reaction. These RNAs will constitute a profile to be used to differentiate allergic from irritant skin reactions.

EXAMPLE 8

Prediction of Irritant Skin Reactions Prior to Clinical Symptoms or with Slight Clinical Presentation This Example provides experiments to identify RNA expression profiles that predict the onset of clinical irritation or toxic or corrosive skin reactions. In order to demonstrate an irritant or toxic/corrosive skin reaction it is necessary to apply the compound to the skin and leave it until a reaction becomes clinically apparent or a suitable amount of time has passed without any reaction (typically 2-3 weeks). The introduction of an assay that could reliably predict the probability that a substance would create a irritant or toxic/corrosive skin reaction after 1-3 hours of application to the skin represents a significant advancement.

Method: A clinical protocol with up to 20 subjects is performed. Occlusive patches are applied to the skin for 1-3 hours. The patches contain strong irritants or known corrosive/toxic materials at concentrations known in advance not to cause more than a slight irritant skin reaction (defined as patchy light pink erythema) under the conditions of the trial. Vehicle controls such as dilutions of the test materials or water are applied. Examples of such strong irritants are: 20% sodium lauryl sulfate; 100% octanol; 10% acetic acid; 100% decanol. After 1-3 hours of exposure, patches (or Finn chambers) are removed and skin clinically scored. The sites are then tape harvested with up to 4 tapes sequentially applied and removed. RNA is extracted from the tapes, amplified by the standard T7 linear method and amplified RNA hybridized to DNA arrays. From this data, distinct RNA differential expression profiles are identified; these profiles will be confirmed in a second experiment with the same chemicals and different subjects.

It is likely that 1 to 3 hours of occlusive exposure to a diluted irritant or toxic/corrosive chemical is sufficient to induce transcriptional changes predictive of a strong irritant or toxic potential without actually inducing severe clinical irritation or toxicity. Thus, using the RNA profile it will be possible to deduce a substance's potential to create a strong irritant or toxic/corrosive skin reaction without actually effecting that reaction.

EXAMPLE 9

Analysis of Psoriatic Lesions and Uninvolved Skin Before Treatment to Identify RNA Profiles Correlated with Specific Treatment Outcome This Example provides experiments to identify, by microarray analysis, specific RNA profiles of psoriatic lesions—using RNA captured by tape stripping—that are predictive of success using a particular treatment(s). As illustrated in the Examples above, tape harvested RNA samples are reflective of pathological and/or normal skin physiology. Furthermore, as illustrated herein, psoriatic lesions can be sorted into different groups depending on the RNA profile revealed in tape strip samples. Thus, with different treatments, higher numbers of patients and the use of nucleic acid arrays to sift through large numbers of genes (human genome scan), it is expected that unique profiles will be identified that predict the effectiveness of a particular therapy.

Method: In this study, psoriatic patients are tape stripped between 1 and 10 times using adhesive tape Prod. No. 90068 from Adhesive Research (Glen Rock, Pa.) on lesional and non-lesional skin before they undergo treatment. Patients that have received treatment previously undergo a standard "washout" period before being tape stripped and initiating treatment. During treatment, patients are tape stripped at weeks 1, 2, 4, 8, 12 and 24; NPF scores are generated at those visits. RNA is isolated, amplified, and hybridized to nucleic acid arrays as previously described. Statistical is performed to correlate RNA profile with NPF score at different weeks.

It is expected that RNA profiles of either lesions and/or uninvolved skin—previous to treatment—exist that correlate with lowering of NPF score (i.e. successful clinical outcome) after treatment with a particular therapy. This will allow the predetermination of the most efficacious therapy for a particular patient.

EXAMPLE 10

Prediction of Treatment Efficacy Before Clinical Indication by Analysis of RNA Early in the Treatment Process This example provides experiments aimed at identifying RNA profiles that are predictive of ultimate treatment efficacy early in the treatment program. It is illustrated herein that tape sampling of psoriatic lesions can be used to monitor the progress of treatment by RNA profiling. Preliminary data have also shown that some mRNA levels do not restore to normal levels and that some patients with this profile fail to ultimately respond to treatment. It is hypothesized that additional RNAs will be identified and that through multivariate analysis RNA expression profiles will be identified that correlate highly with response to treatment early in the treatment process.

Method: Patients are tape stripped on lesional and non-lesional skin before and during therapy. Tape strip samples and NPF scores are generated at times 0, 1 week, 2 week, 3 week, 4 week and 6 weeks. RNA is isolated, amplified and hybridized to DNA arrays as previously disclosed herein. Data is analyzed and RNA profiles correlated with NPF scores.

It is anticipated that RNA profiles generated early in the treatment regime (weeks 1 through 6) that are highly correlated with a reduction of ultimate NPF score (at week 16 or greater), will be generated. Identification of such profiles will allow the identification of patients ultimately destined not to respond to treatment, thus allowing a change in treatment early in the process. Such screening will allow greater cost and time efficiency, and probably speed time to recovery.

BIBLIOGRAPHY

Ackerman, S. J., L. Liu, et al. (2002). "Charcot-Leyden crystal protein (galectin-10) is not a dual function galectin with lysophospholipase activity but binds a lysophospholipase inhibitor in a novel structural fashion." J Biol Chem 277 (17): 14859-68.

Aitman, T. J. (2001). "DNA microarrays in medical practice." Bmj 323(7313): 611-5.

Alberts, B., D. Bray, et al. (1994). The immune system. Molecular Biology of The Cell. New York, N.Y., Garland Publishing, Inc.: 1229-1235.

Allison, D. B., G. L. Gadbury, et al. (2002). "A mixture model approach for the analysis of microarray gene expression data." Computational Statistics and Data Analysis 39: 1-20.

Applied Biosystems (2001). User Bulletin #2: Relative quantitation of gene expression.

Asadullah, K., W. Sterry, et al. (2002). "Cytokines: interleukin and interferon therapy in dermatology." Clin Exp Dermatol 27(7): 578-84.

Baker, B. S., J. M. Ovigne, et al. (2003). "Normal keratinocytes express Toll-like receptors (TLRs) 1, 2 and 5: modulation of TLR expression in chronic plaque psoriasis." Br J Dermatol 148(4): 670-9.

Baldi, P. and G. W. Hatfield (2002). DNA microarrays and gene expression: From experiments to data analysis and modeling. Cambridge, UK, Cambridge University Press.

Baldi, P. and A. D. Long (2001). "A Bayesian framework for the analysis of microarray expression data: regularized t-test and statistical inferences of gene changes." Bioinformatics 17(6): 509-519.

Bayon, Y., A. Alonso, et al. (1998). "Mechanisms of cell signaling in immune-mediated inflammation." Cytokines Cell Mol Ther 4(4): 275-86.

Benavides, F., M. F. Starost, et al. (2002). "Impaired hair follicle morphogenesis and cycling with abnormal epidermal differentiation in nackt mice, a cathepsin L-deficient mutation." Am J Pathol 161(2): 693-703.

Bertucci, F., R. Houlgatte, et al. (2001). "Gene expression profiling of cancer by use of DNA arrays: how far from the clinic?" Lancet Oncol 2(11): 674-82.

Boelsma, E., S. Gibbs, et al. (1998). "Expression of skin-derived antileukoproteinase (SKALP) in reconstructed human epidermis and its value as a marker for skin irritation." Acta Derm Venereol 78(2): 107-13.

Boxman, I. L., P. J. Hensbergen, et al. (2002). "Proteomic analysis of skin irritation reveals the induction of HSP27 by sodium lauryl sulphate in human skin." Br J Dermatol 146(5): 777-85.

Bustin, S. A. (2002). "Quantification of mRNA using real-time reverse transcription PCR (RT-PCR): trends and problems." J Mol Endocrinol 29(1): 23-39.

Chung, N. M., C. M. Marshall, et al. (2001). "Sodium dodecyl sulfate induces plasminogen activator inhibitor type 2 expression in epidermal keratinocytes in vivo and in vitro." J Invest Dermatol 117(3): 647-53.

Chung, S. I., S. Y. Lee, et al. (1996). "Factors that control extravascular fibrinolysis." Semin Thromb Hemost 22(6): 479-88.

Colonna, M. (2003). "TREMs in the immune system and beyond." Nat Rev Immunol 3(6): 445-53.

Coquette, A., N. Berna, et al. (2003). "Analysis of interleukin-1alpha (IL-1alpha) and interleukin-8 (IL-8) expression and release in in vitro reconstructed human epidermis for the prediction of in vivo skin irritation and/or sensitization." Toxicol In Vitro 17(3): 311-21.

Corsini, E. and C. L. Galli (1998). "Cytokines and irritant contact dermatitis." Toxicol Lett 102-103: 277-82.

Cumberbatch, M., R. J. Dearman, et al. (2002). "Differential regulation of epidermal langerhans cell migration by interleukins (IL)-1 alpha and IL-1 beta during irritant- and allergen-induced cutaneous immune responses." Toxicol Appl Pharmacol 182(2): 126-35.

Dong, V. M., D. H. McDermott, et al. (2003). "Chemokines and diseases." Eur J Dermatol 13(3): 224-30.

Feghali, C. A. and T. M. Wright (1997). "Cytokines in acute and chronic inflammation." Front Biosci 2: d12-26.

Flier, J., D. M. Boorsma, et al. (1999). "The CXCR3 activating chemokines IP-10, Mig, and IP-9 are expressed in allergic but not in irritant patch test reactions." J Invest Dermatol 113(4): 574-8.

Fray, M. J., R. P. Dickinson, et al. (2003). "A potent, selective inhibitor of matrix metalloproteinase-3 for the topical treatment of chronic dermal ulcers." J Med Chem 46(16): 3514-25.

Freedberg, I. M., M. Tomic-Canic, et al. (2001). "Keratins and the keratinocyte activation cycle." J Invest Dermatol 116(5): 633-40.

Galiegue, S. and P. Casellas (2002). "[Exploitation of expression profiles: examples in oncology]." J Soc Biol 196(4): 313-5.

Gibson, U. E., C. A. Heid, et al. (1996). "A novel method for real time quantitative RT-PCR." Genome Res 6(10): 995-1001.

Grangsjo, A., A. Leijon-Kuligowski, et al. (1996). "Different pathways in irritant contact eczema? Early differences in the epidermal elemental content and expression of cytokines after application of 2 different irritants." Contact Dermatitis 35(6): 355-60.

Hatfield, G. W., S. P. Hung, et al. (2003). "Differential analysis of DNA microarray gene expression data." Mol. Microbiol. 47(4): 871-877.

Heid, C. A., J. Stevens, et al. (1996). "Real time quantitative PCR." Genome Res 6(10): 986-94.

Herouy, Y. (2001). "Matrix metalloproteinases in skin pathology (Review)." Int J Mol Med 7(1): 3-12.

Hoefakker, S., M. Caubo, et al. (1995). "In vivo cytokine profiles in allergic and irritant contact dermatitis." Contact Dermatitis 33(4): 258-66.

Hoffrage, U., S. Lindsey, et al. (2000). "Communicating Statistical Information." Science 290(5500): 2261-2262.

Howie, S. E., R. D. Aldridge, et al. (1996). "Epidermal keratinocyte production of interferon-gamma immunoreactive protein and mRNA is an early event in allergic contact dermatitis." J Invest Dermatol 106(6): 1218-23.

Hung, S.-P., P. Baldi, et al. (2002). "Global gene expression profiling in *Escherichia coli* K12: The effects of leucine-responsive regulatory protein." J. Biol. Chem. 277(43): 40309-40323.

Ichinose, A. (2001). "Physiopathology and regulation of factor XIII." Thromb Haemost 86(1): 57-65.

Kahari, V. M. and U. Saarialho-Kere (1997). "Matrix metalloproteinases in skin." Exp Dermatol 6(5): 199-213.

Kawada, A., K. Hara, et al. (1997). "Processing of cathepsins L, B and D in psoriatic epidermis." Arch Dermatol Res 289(2): 87-93.

Kerkhoff, C., I. Eue, et al. (1999). "The regulatory role of MRP8 (S100A8) and MRP14 (S100A9) in the transendothelial migration of human leukocytes." Pathobiology 67(5-6): 230-2.

Kilpatrick, D.C. (2002). "Animal lectins: a historical introduction and overview." Biochim Biophys Acta 1572(2-3): 187-97.

Komine, M., L. S. Rao, et al. (2001). "Interleukin-1 induces transcription of keratin K6 in human epidermal keratinocytes." J Invest Dermatol 116(2): 330-8.

Lacroix, M., N. Zammatteo, et al. (2002). "A low-density DNA microarray for analysis of markers in breast cancer." Int J Biol Markers 17(1): 5-23.

Lendeckel, U., M. Arndt, et al. (2003). "Synergistic action of DPIV and APN in the regulation of T cell function." Adv Exp Med Biol 524: 123-31.

Li, C. and W. H. Wong (2001). "Model-based analysis of oligonucleotide arrays: expression index computation and outlier detection." Proc. Natl. Acad. Sci. U.S.A. 98(1): 31-36.

Lobmann, R., A. Ambrosch, et al. (2002). "Expression of matrix-metalloproteinases and their inhibitors in the wounds of diabetic and non-diabetic patients." Diabetologia 45(7): 1011-6.

Long, A. D., H. J. Mangalam, et al. (2001). "Improved statistical inference from DNA microarray data using analysis of variance and a Bayesian statistical framework. Analysis of global gene expression in Escherichia coli K12." J. Biol. Chem. 276(23): 19937-19944.

Lucas, M., L. Daniel, et al. (2002). "Massive inflammatory syndrome and lymphocytic immunodeficiency in KARAP/DAP12-transgenic mice." Eur J Immunol 32(9): 2653-63.

Melen, K., P. Keskinen, et al. (1996). "Human MxB protein, an interferon-alpha-inducible GTPase, contains a nuclear targeting signal and is localized in the heterochromatin region beneath the nuclear envelope." J Biol Chem 271 (38): 23478-86.

Molhuizen, H. O. and J. Schalkwijk (1995). "Structural, biochemical, and cell biological aspects of the serine proteinase inhibitor SKALP/elafin/ESI." Biol Chem Hoppe Seyler 376(1): 1-7.

Morhenn, V. B., E. Y. Chang, et al. (1999). "A noninvasive method for quantifying and distinguishing inflammatory skin reactions." J Am Acad Dermatol 41(5 Pt 1): 687-92.

Muller-Decker, K., G. Furstenberger, et al. (1994). "Keratinocyte-derived proinflammatory key mediators and cell viability as in vitro parameters of irritancy: a possible alternative to the Draize skin irritation test." Toxicol Appl Pharmacol 127(1): 99-108.

Muller-Decker, K., T. Heinzelmann, et al. (1998). "Arachidonic acid metabolism in primary irritant dermatitis produced by patch testing of human skin with surfactants." Toxicol Appl Pharmacol 153(1): 59-67.

Paludan, K. and K. Thestrup-Pedersen (1992). "Use of the polyerase chain reaction in quantification of interleukin 8 mRNA in minute epidermal samples." J Invest Dermatol 99(6): 830-5.

Perkins, M. A., C. W. Cardin, et al. (2002). "A non-invasive tape absorption method for recovery of inflammatory mediators to differentiate normal from compromised scalp conditions." Skin Res Technol 8(3): 187-93.

Perkins, M. A., M. A. Osterhues, et al. (2001). "A noninvasive method to assess skin irritation and compromised skin conditions using simple tape adsorption of molecular markers of inflammation." Skin Res Technol 7(4): 227-37.

Phan, U. T., R. L. Lackman, et al. (2002). "Role of the C-terminal propeptide in the activity and maturation of gamma-interferon-inducible lysosomal thiol reductase (GILT)." Proc Natl Acad Sci USA 99(19): 12298-303.

Pilcher, B. K., M. Wang, et al. (1999). "Role of matrix metalloproteinases and their inhibition in cutaneous wound healing and allergic contact hypersensitivity." Ann N Y Acad Sci 878: 12-24.

Raval, G. N., S. Bharadwaj, et al. (2003). "Loss of expression of tropomyosin-1, a novel class II tumor suppressor that induces anoikis, in primary breast tumors." Oncogene 22(40): 6194-203.

Ryan, C. A. and G. F. Gerberick (1999). "Cytokine mRNA expression in human epidermis after patch treatment with rhus and sodium lauryl sulfate." Am J Contact Dermat 10(3): 127-35.

Samal, B., Y. Sun, et al. (1994). "Cloning and characterization of the cDNA encoding a novel human pre-B-cell colony-enhancing factor." Mol Cell Biol 14(2): 1431-7.

Satagopan, J. M. and K. S. Panageas (2003). "A statistical perspective on gene expression data analysis." Stat Med 22(3): 481-99.

Suzuki, T., P. J. Higgins, et al. (2000). "Control selection for RNA quantitation." Biotechniques 29(2): 332-7.

Syrokou, A., K. Dobra, et al. (2002). "Synthesis and expression of mRNA encoding for different versican splice variants is related to the aggregation of human epithelial mesothelioma cells." Anticancer Res 22(6C): 4157-62.

Thorey, I. S., J. Roth, et al. (2001). "The $Ca^{2+}$-binding proteins S100A8 and S100A9 are encoded by novel injury-regulated genes." J Biol Chem 276(38): 35818-25.

Tomic-Canic, M., M. Komine, et al. (1998). "Epidermal signal transduction and transcription factor activation in activated keratinocytes." J Dermatol Sci 17(3): 167-81.

Tricarico, C., P. Pinzani, et al. (2002). "Quantitative real-time reverse transcription polyerase chain reaction: normalization to rRNA or single housekeeping genes is inappropriate for human tissue biopsies." Anal Biochem 309(2): 293-300.

Ulfgren, A. K., L. Klareskog, et al. (2000). "An immunohistochemical analysis of cytokine expression in allergic and irritant contact dermatitis." Acta Derm Venereol 80(3): 167-70.

Vallejo, A. N., L. O. Mugge, et al. (2000). "Central role of thrombospondin-1 in the activation and clonal expansion of inflammatory T cells." J Immunol 164(6): 2947-54.

van Ruissen, F., M. Le, et al. (1998). "Differential effects of detergents on keratinocyte gene expression." J Invest Dermatol 110(4): 358-63.

Verhoef, J. (1991). "The phagocytic process and the role of complement in host defense." J Chemother 3 Suppl 1: 93-7.

Vermeer, P. D., L. A. Einwalter, et al. (2003). "Segregation of receptor and ligand regulates activation of epithelial growth factor receptor." Nature 422(6929): 322-6.

Welss, T., J. Sun, et al. (2003). "Hurpin is a selective inhibitor of lysosomal cathepsin L and protects keratinocytes from ultraviolet-induced apoptosis." Biochemistry 42(24): 7381-9.

Whipple, M. E. and W. P. Kuo (2002). "DNA microarrays in otolaryngology-head and neck surgery." Otolaryngol Head Neck Surg 127(3): 196-204.

Although the invention has been described with reference to the above example, it will be understood that modifications and variations are encompassed within the spirit and scope of the invention. Accordingly, the invention is limited only by the following claims.

What is claimed is:

1. A non-invasive method for isolating or detecting a protein from an epidermal sample of a human subject, comprising:
   a) applying an adhesive tape to a target area of the skin of the subject in a manner sufficient to isolate an epidermal sample adhering to the adhesive tape, wherein the epidermal sample comprises cells from the stratum corneum of the subject, and wherein the tape comprises a rubber adhesive;
   b) lysing the cells to extract at least one protein selected from the group consisting of MGSA, TNFα, IFNγ, CD2, IL-12B, Krt-16, Krt-17, IL-23A, and an expression product of a gene listed in Table VI; and c) isolating or detecting a protein in the epidermal sample.

2. The method of claim 1, wherein the tape comprises a rubber adhesive on a polyurethane film.

3. The method of claim 1, wherein about one to ten adhesive tapes are applied and removed from the skin.

4. The method of claim 1, wherein about one to eight adhesive tapes are applied and removed from the skin.

5. The method of claim 1, wherein about one to five adhesive tapes are applied and removed from the skin.

* * * * *